(12) United States Patent
Allen et al.

(10) Patent No.: US 7,288,695 B2
(45) Date of Patent: Oct. 30, 2007

(54) PLANT GENES ENCODING DR1 AND DRAP1, A GLOBAL REPRESSOR COMPLEX OF TRANSCRIPTION

(75) Inventors: Stephen M Allen, Wilmington, DE (US); Qun Zhu, West Chester, DE (US)

(73) Assignee: E.I. DuPont de Nemours and Company, Wilmington, DE (US)

(*) Notice: Subject to any disclaimer, the term of this patent is extended or adjusted under 35 U.S.C. 154(b) by 314 days.

(21) Appl. No.: 10/628,969

(22) Filed: Jul. 28, 2003

(65) Prior Publication Data

US 2004/0181828 A1   Sep. 16, 2004

Related U.S. Application Data

(63) Continuation of application No. 09/789,054, filed on Feb. 20, 2001, now abandoned, which is a continuation-in-part of application No. 09/485,558, filed as application No. PCT/US98/16688 on Aug. 12, 1998, now abandoned.

(60) Provisional application No. 60/055,865, filed on Aug. 15, 1997.

(51) Int. Cl.
    A01H 5/00    (2006.01)
    A01H 5/10    (2006.01)
    C12N 15/29   (2006.01)
    C01N 15/82   (2006.01)

(52) U.S. Cl. .................. 800/298; 435/468; 435/320.1; 536/23.6; 800/278

(58) Field of Classification Search .................... None
    See application file for complete search history.

(56) References Cited

U.S. PATENT DOCUMENTS 5,968,793 A   10/1999   Liu et al.

FOREIGN PATENT DOCUMENTS

WO    WO99/09175    2/1999

OTHER PUBLICATIONS

Baxevanis et al 1998, Nucleic Acids Research 26(1): 372-375.*
Maldonado et al 1999, Cell 99: 455-458.*
Kim et al 2000, Molecular and Cellular Biology 20(7): 2455-2465.*
Ronald C. Conaway et al., Annu. Rev. Biochem., vol. 62:161-190, 1993, General Initiation Factors for RNA Polymerase II.
Leigh Zawel et al., Annu. Rev. Biochem., vol. 64:533-561, 1995, Common Themes In Assembly and Function of Eukaryotic Transcription Complexes.
Wendy Hanna-Rose et al., Trends in Genetics, vol. 12(6):229-234, Active Repression Mechanisms of Eukaryotic Transcription Repressors.
Yang Shi et al., Cell, vol. 67:377-388, Oct. 18, 1991, Transcriptional Repression by YY1, a Human GL1-Kruppel-Related Protein, and Relief of Repression by Adenovirus E1A Protein.

Robert Benezra et al., Cell, vol. 61:49-59, Apr. 6, 1990, The Protein Id: A Negative Regulator of Helix-Loop-Helix DNA Binding Proteins.
Patrick A. Baeuerle et al., Science, vol. 242:540-545, IkB: A Specific Inhibitor of the NF-kB Transcription Factor.
Donald E. Ayer et al., Cell, vol. 80:767-776, Mar. 10, 1995, Mad-Max Transcriptional Repression is Mediated by Ternary Complex Formation with Mammalian Homologs of Yeast Repressor Sin3.
Juan A. Inostroza et al., Cell, vol. 70:477-489, Aug. 7, 1992, Dr1, a TATA-Binding Protein-Associated Phosphoprotein and Inhibitor of Class II Gene Transcription.
Sungjoon Kim et al., PNAS, vol. 94:820-825, Feb. 1997, The Dr1/DRAP1 Heterodimer is a Global Repressor of Transcription in vivo.
Takahashi Kuromori et al., Nucleic Acids Res., vol. 22(24):5296-5301, Cloning of cDNAs from *Arabidopsis thaliana* that encode putative protein phosphatase 2C and a human Dr1-like protein by transformation of a fission yeast mutant.
Fred Mermelstein et al., Genes & Dev., vol. 10:1033-1048, 1996, Requirement of a corepressor for Dr1-mediated repression of transcription.
Robert J. White et al., Science, vol. 266:448-450, 1994, Differential Regulation of RNA Polymerases I, II, and III by the TBP-Binding Repressor Dr1.
Tae Kook Kim et al., Journ. of Biol. Chem., vol. 270(18):10976-10981, 1995, TATA-binding Protein Residues Implicated in a Functional Interplay between Negative Cofactor NC2(DR1) and General Factors TFIIA and TFIIB.
Jaesang Kim et al., Journ. of Biol. Chem., vol. 271(31:18405-18412, 1996, A Negative Cofactor Containing Dr1/p19 Modulates Transcription with TFIIA in a Promoter-specific Fashion.
Sungjoon Kim et al., Mol. & Cell. Biol., vol. 20(7):2455-2465, Apr. 2000, Genetic Analysis of the Ydr1-Bur6 Repressor Complex Reveals an Intricate Balance among Transcriptional Regulatory Proteins in Yeast.
Andreas Goppelt et al., EMBO J., vol. 15(12):3105-3116, 1996, A mechanism for repression of class II gene transcription through specific binding of NC2 to TBP-promoter complexes via heterodimeric histone fold domains.
Ellen L. Gadbois et al., PNAS, vol. 94:3145-3150, Apr. 1997, Functional antagonism between RNA polymerase II holoenzyme and global negative regulator NC2 in vivo.
Gregory Prelich, Mol. & Cell. Biol., vol. 17(4):2057-2065, Apr. 1997, *Saccharomyces cerevisiae* BUR6 Encodes a DRAP1/NC2alpha Homolog that has both Positive and Negative Roles in Transcription in Vivo.
Kam Yeung et al., Mol. & Cell. Biol., vol. 17(1):36-45, Jan. 1997, Functional Dissection of a Human Dr1-DRAP1 Repressor Complex.
Yong Cang et al., EMBO J., vol. 18(23):6662-6671, 1999, A new regulatory domain on the TATA-binding protein.

(Continued)

*Primary Examiner*—David H Kruse

(57) ABSTRACT

This invention relates to an isolated nucleic acid fragment encoding a protein involved in regulation of gene expression. The invention also relates to the construction of a chimeric gene encoding all or a portion of the protein involved in regulation of gene expression, in sense or antisense orientation, wherein expression of the chimeric gene results in production of altered levels of the protein involved in regulation of gene expression in a transformed host cell.

13 Claims, 15 Drawing Sheets

OTHER PUBLICATIONS

Figures 3A, 3B:
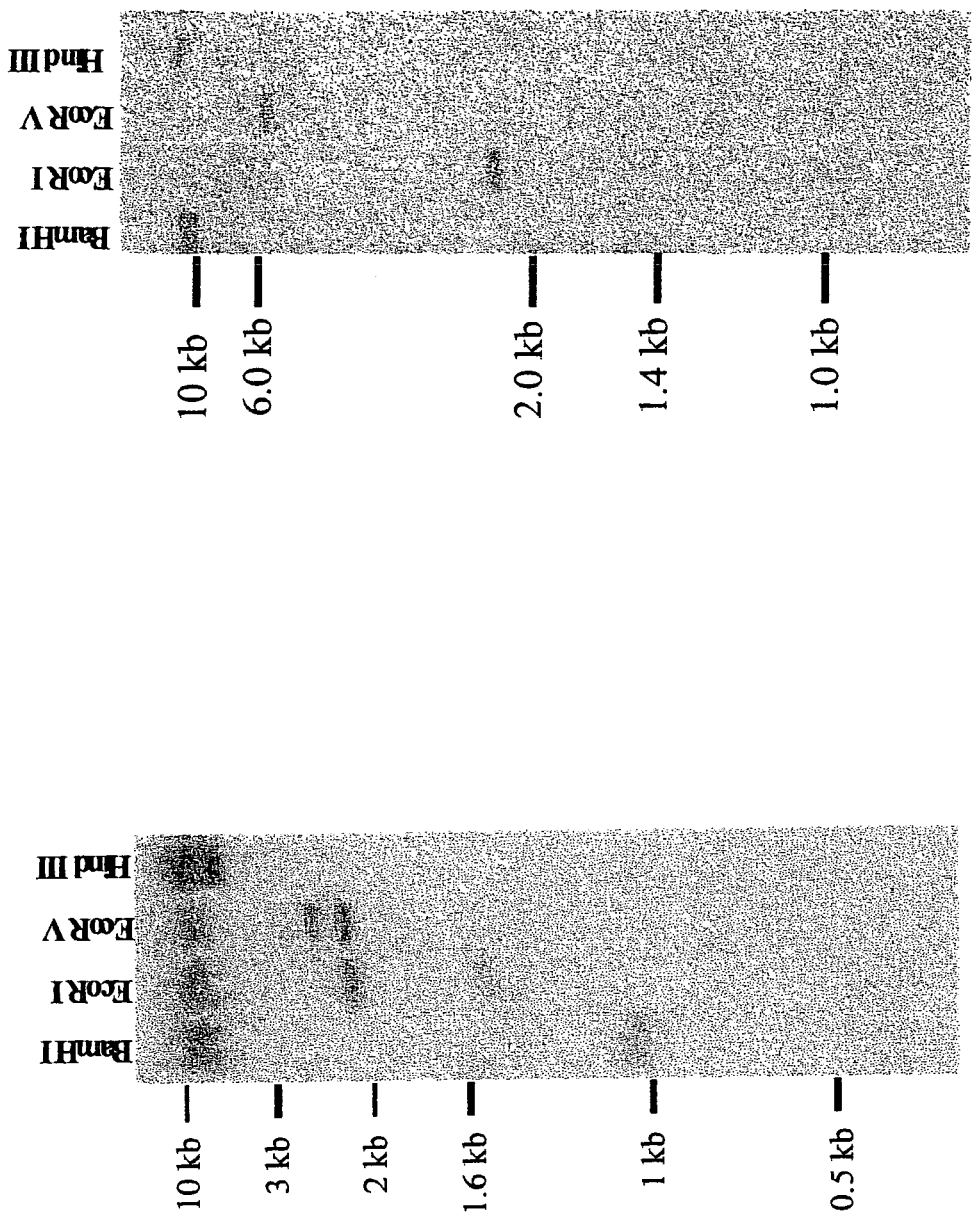

Jun Xie et al., EMBO J., vol. 19(4):672-682, 2000, A single point mutation in TFIIA suppresses NC2 requirement in vivo.

National Center for Biotechnology Information General Identifier No. 11279032, Jul. 28, 2000, Bevan, M. et al.

National Center for Biotechnology Information General Identifier No. 8346556, Jun. 8, 2000, Bevan, M. et al.

National Center for Biotechnology Information General Identifier No. 1352318, Feb. 1, 1996, Kuromori, T. et al., Cloning of cDNAs from *Arabidopsis thaliana* that encode putative protein phosphatase 2C and a human Dr1-like protein by transformation of a fission yeast mutant.

Andreas D. Baxevanis et al., Nucleic Acids Res., vol. 26(1):372-375, 1998, Histone Sequence Database: new histone fold family members.

National Center for Biotechnology Information General Identifier No. 7513394, Nov. 5, 1999, Goppelt, A. et al., A mechanism for repression of class II gene transcription through specific binding of NC2 to TBP-promoter complexes via heterodimeric histone fold domains.

National Center for Biotechnology Information General Identifier No. 1491710, Mar. 3, 1999, Goppelt, A. et al., A mechanism for repression of class II gene transcription through specific binding of NC2 to TBP-promoter complexes via heterodimeric histone fold domains.

Cheng-Ting Chien et al., PNAS, vol. 88:9578-9582, Nov. 1991, The two-hybrid system: A method to identify and clone genes for proteins that interact with a protein of interest.

Randolph Eible, Biotechniques, vol. 13:18-20, 1992, A simple and Efficient Procedure for Transformation of Yeasts.

George C. Allen et al., The Plant Cell, vol. 5:603-613, Jun. 1993, Scaffold Attachment Regions Increase Reporter Gene Expression in Stably Transformed Plant Cells.

Zhan-Bin Liu et al., Plant Cell, vol. 6:645-657, May 1994, Soybean GH3 Promoter Contains Multiple Auxin-Inducible Elements.

A. G. Von Arnim et al., Gene, vol. 221:35-43, 1998, Cloning vectors for the expression of green fluorescent protein fusion proteins in transgenic plants.

Frank Gindullis et al., Plant Cell, vol. 11:1755-1767, Sep. 1999, MAF1, a Novel Plant Protein Interacting with Matrix Attachment Region Binding Protein MFP1, is Located at the Nuclear Envelope.

Dirk Gorlich et al., Science, vol. 271:1513-1518, Mar. 1996, Nucleocytoplasmic Transport.

Robert J. Grebenok et al., Plant J., vol. 12(3):685-696, 1997, Characterization of the targeted nuclear accumulation of GFP within the cells of transgenic plants.

Qun Zhu et al., Plant Mol. Biol., vol. 29:535-550, 1995, Cloning and properties of a rice gene encoding phenylalanine ammonia-lyase.

Nobuko Iwataki et al., Plant Mol. Biol., vol. 34:69-79, 1997, Restoration of TATA-dependent transcription in a heat-inactivated extract of tobaaco nuclei by recombinant TATA-binding protein (TBP) from tobacco.

Qun Zhu et al., Plant J., vol. 7(6):1021-1030, 1995, Accurate in vitro transcription from circularized plasmid templates by plant whole cell extracts.

F. Sanger et al., PNAS, vol. 74(12):5463-5467, Dec. 1977, DNA sequencing with chain-terminating inhibitors.

Qun Zhu et al., Plant Cell, vol. 7:1681-1689, Oct. 1995, TATA Box and Initiator Functions in the Accurate Transcription of a Plant Minimal Promoter in Vitro.

Richard A. Jefferson, Plant Mol. Biol. Rep., vol. 5(4):387-405, 1987, Assaying Chimeric Genes in Plants: The GUS Gene Fusion System.

Song, Wen et al., "Functional Dissection of a Rice Dr1/DrAp1 Transcriptional Repression Complex", The Plant Cell (Jan. 2002) vol. 14, pp. 181-195.

Baxevanis, Andreas D. et al, "Histone Sequence Database:new histone fold family members", Nucleic Acids Research (1998) vol. 26, No. 1, pp. 372-375.

* cited by examiner

```
SEQ ID NO:04  L-LDST-L--------RETNS---LPNSLAES--TCYLAPAFRRADSVPCVEMDPMD
SEQ ID NO:06  T-RPIP-LC-------PSKPNC---RPNSLAGS--TCYLAPAFCRADSLLRLEMDPMD
SEQ ID NO:10  -------------------------------------------------MDPMD
SEQ ID NO:14  ICVSAT-TC-------SPPPPCSSHHPHHLLQSVDSSFL-PLFFR--------MEPMD
SEQ ID NO:20  ESPPATRSCLRAHRRRPSPPSPSSGPPVPGGTRRRRPQAQAPSRFR-----RRGMDPMD
SEQ ID NO:22  -------------------------------------------------MDPMD
SEQ ID NO:41  -------------------------------------------------MDPMD
              1                                                       60

SEQ ID NO:04  IVGKSKEDVSLPKSTMVKIIKEMLPPDVRVARDAQDLLVECCVEFINLLSSESNEVCSRE
SEQ ID NO:06  IVGKSKEDVSLPKSTMFKIIKEMLPPDVRVARDAQDLLVECCVEFINLLSSESNEVCSRE
SEQ ID NO:10  IVGKSKEDVSLPKSTMFKIIKEMLPPDVRVARDAQDLLVECCVEFINLLSSESNEVCSRE
SEQ ID NO:14  IVGKAKEDASLPKATMTKIIKEMLPPDVRVARDAQDLLIECCVEFINLVSSESNEVCNKE
SEQ ID NO:20  IVGKSKEDVSLPKSTMTKIIKEMLPPDVRVARDTQDLLVECCVEFINLLSSESNDVCSRD
SEQ ID NO:22  IVGKSKEDVSLPKSTMTKIIKEMLPPDVRVARDTQDLLVECCVEFINLLSSESNDVCSRD
SEQ ID NO:41  IVGKSKEDASLPKATMTKIIKEMLPPDVRVARDAQDLLIECCVEFINLVSSESNDVCNKE
              61                                                      120

SEQ ID NO:04  EKKTIAPEHVIKALSDLGFREYIEEVYAAYEQHKLETL-DSPKAGKFT-RIEMTEEEAVA
SEQ ID NO:06  EKKTIAPEHVIKALSDLGFREYIEEVYAAYEQHKLDTL-DSPKAGKFT-GIEMTEEEAVA
SEQ ID NO:10  DKKTIAPEHVLRALQDLGFREYIEEVQAAYEHHKHDTL-DSPKASKFT-GVEMTEEQAVA
SEQ ID NO:14  ERRTIAPEHVLKALGVLGFGEYIEEVYAAYEQHKLETMQDSLKGAKWSNRAEMTEEEALA
SEQ ID NO:20  DKKTIAPEHVIRALQDLGFKEYVEEVYAAYEQHKLETL-DSPKATKFT-GIEMTEEEAVA
SEQ ID NO:22  DKKTIAPEHVIRALQDLGFKEYVEEVYAAYEQHKLETL-DSPKATKFT-GIEMTEEEAVA
SEQ ID NO:41  DKRTIAPEHVLKALQVLGFGEYIEEVYAAYEQHKYETMQDTQRSVKWNPGAQMTEEAAAA
              121                                                     180
```

FIG. 1A

```
SEQ ID NO:04   EQQRMFAEARARMNNGAPKPKEPEQEPPQLPQAQPQ--LQLHTEPQQPMQSQVLHSQTQ
SEQ ID NO:06   EQQRMFAEARARMNNGAPKPKETEQEPPQQPQAQPQ--LQLHTEPQQPVQSQVLHSPTQ
SEQ ID NO:10   EQQRMFAEARARMNNGAAKPKEPEPEAQQQTQQPPQ--PQLHPQPQQPLQPQLHPQPQ
SEQ ID NO:14   EQQRMFAEARARMNNGAI--QSKEPEADQ-S------------------------
SEQ ID NO:20   EQQRMFAEARARMNNGAAKPKEPALEPQNQPQQPPQHLQLHPQAQQPPQPPQPQLHHPQS
SEQ ID NO:22   EQQRMFAEARARMNNGAAKPKEPALEPQNQPQQPPQHLQLHPQAQQPPQPPQPQLHYPQS
SEQ ID NO:41   EQQRMFAEARARMNNGGVSVPQEHPETDQRS-------------------------
               181                                                      240

SEQ ID NO:04   HY---LQPQLQLHHQPQQLPQVQLHSQPQL------QPQVHLHPQPQLPPQLQVHQQLQQ
SEQ ID NO:06   HS---LQPQVQLHPQPQQLPQVQVHSQTQLHPQ-PQQPQVQVHPQLQQLPQLQAHSQPPQ
SEQ ID NO:10   QQPSQLHPQQLLHPQSQQTPQ----PQPQVHPQ-PQQPP-QLQPQPQLLQQPQLPQQLQ-
SEQ ID NO:14   ----------------------------------------------------------
SEQ ID NO:20   QQPLHPQLQPLQPYTQAPPQQPLHPQLQPYTQAPPQQPLQPPLQLYPQAQPEQPLQPQSSGST
SEQ ID NO:22   QQPL----QPFTQAPPQQPLHPQLQQYTQAPPQQPLQPPLQLYPQAQPEQPLQPQSSGST
SEQ ID NO:41   ----------------------------------------------------------
               241                                                      300

SEQ ID NO:04   PPQVQVHQQPEVQPQEAQLQSSAQQTSQPQPQAQ-------L-QSQGHSQAQLQAGLLGQ
SEQ ID NO:06   P-QVQIHPQPQ-QPPQVQLQSSVQQTSQPQPQVH-------LYNHRGGSQAQLQPQLPGQ
SEQ ID NO:10   --PQSQLPPQPQ-QPPQLQLQSQLHPQPQQPPQLQ-------P-QPQLHQQPQPQAELQSQ
SEQ ID NO:14   ----------------------------------------------------------
SEQ ID NO:20   TGTCVISTAAPSATGTTAAATSAPAIPA--------------ISTAAPSATPADASAAAAA
SEQ ID NO:22   TGTCVISAAAPSATGTLLLQPPPQQSPQSQLHQQPQPTLVPPQPQPLELQQPQPL
SEQ ID NO:41   ----------------------------------------------------------
               301                                                      360
```

FIG. 1B

```
SEQ ID NO:04   LQTQAQTGPDMDS
SEQ ID NO:06   LQTQGQTGPGIDS
SEQ ID NO:10   SQPQTEHGLD-SS
SEQ ID NO:14   --------LES
SEQ ID NO:20   AATSTP----AT
SEQ ID NO:22   TQLQAEHGLDWDS
SEQ ID NO:41   ---------PQS
               361          373
```

FIG. 1C

```
SEQ ID NO:28   ---MRKKLGTRFPAARIKKIMQADEDVGKIALAVPVLVSRALELFLQDLIDRTYEITLQS
SEQ ID NO:32   ---MRKKLGTRFPAARIKKIMQADEDVGKIALAVPVLVSRALELFLQDLIDRTYEITLQS
SEQ ID NO:34   ---MRKKLDTRFPAARIKKIMQADEDVGKIALAVPVLVSKALELFLQDLCDRTYEITLQR
SEQ ID NO:40   ---TRRKKLGTRFPAARIKKIMQADEDVGKIALAVPVLVSRALELFLQDLIDHSYKITLQS
SEQ ID NO:42   MPSKKKKYNARFPPARIKKIMQTDEEIGKVAAAVPVIISRALELFLESLLKKACQVTQSR
               1                                                           60

SEQ ID NO:28   GAKTLNSFHLKQCVKRYSSFDFLTEVVSSKVPDL----GGADSCGDERVLPRRRKS--NGS
SEQ ID NO:32   GAKTLNSFHLKQCVRRYSSFDFLTEVVNKVPDL----GGADSCGDDRALPRRRKALPNGS
SEQ ID NO:34   GAKTMNSLHLKHCVQSYNVFDFLRDVVSRVPDYSHGHGHAEAGPDDRAIAKRRKAVGDDG
SEQ ID NO:40   GAKTLNSFHLKQCVKRYSSFDFLTEIVNKVPDL----GGGESCGDERGLPRRRK-FSNGS
SEQ ID NO:42   NAKTMTTSHLKQCIELEQQFDFLKDLVASVPDM-QGDGEDNHMDGDKGARRGRKPGSGGR
               61                                                         120

SEQ ID NO:28   DPENDESRSSKM--AIRNANTSPRGRGRGRPPTKRKEVGYVQFEDESSMFAEQ
SEQ ID NO:32   DPENEESRSSKM--AVRSANISPRGRGRGRGRGRPPTKRKEVGYVQFEDESSMFADQ
SEQ ID NO:34   NDSDEEAKRSKMHELGHTGSTGRGRGRGRGRGRGRGRPPLNR-EIYHQDAESEPCTSVQP
SEQ ID NO:40   DPENEEPRSSKM--PIRSLNTSPRGRGRGRPPTKRKEIGYVQFEDESSMFAEQ
SEQ ID NO:42   KNGGMGTKSK-------------------------DKKLSGTD
               121                                                        180

SEQ ID NO:28   GET----------LPGEGTVPEINSGNEITPQ-------STQPPLTAPAQA
SEQ ID NO:32   GEA----------LPGEETVPETIHGTESVPP-------STHPPAEAPSAA
SEQ ID NO:34   SNPQNTNTSVAMDSGSESKEIPKEQNIAVPVESTDSLRNIDLNAITNENDDKKASAAADA
SEQ ID NO:40   SEP----------LPGDEIVPETNRGNESIPQ-------SSHPLVEAPSAM
SEQ ID NO:42   SEQEDESEDTDTDGEEETSQPPPQASHPSAHFQSPPTPFLPFA----STLPLPPAPPGP
               181                                                        240
```

FIG. 2A

```
           *    *        *          **             *  **           *    ******     *
SEQ ID NO:28  T----NSKVEEA-STDHQ---SDWPMPDATGNIGVGPSGFGHLTVQVDEDE-DYDNED-
SEQ ID NO:32  EIPAPNPKVEEAAKNDDHQ---PDWPMPDAIGNIGVGPSGFGHLTVQVDEDE-DYDNED-
SEQ ID NO:34  SVPEPDASVPEPPTESKHEEIPGWSLSD-VDKMAIDSLQLAQLGRPLEEDEEDYDEEEG
SEQ ID NO:40  T-PAVISKVEEA-STNHQ---PDWPMPDAIGGIGVGPSSFGHLTVQVDEVE-DYDNED-
SEQ ID NO:42  SAPD------------------------------------------EEDEEDYDS---
              241                                                     299
```

FIG. 2B pBDGal4::rDRAP1     
pADGal4::rDr1       
FIG. 4A
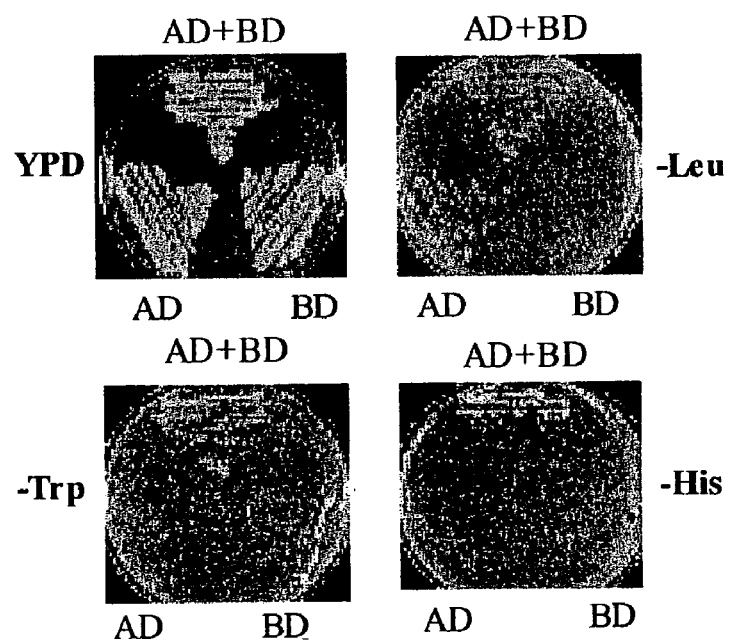
FIG. 4B

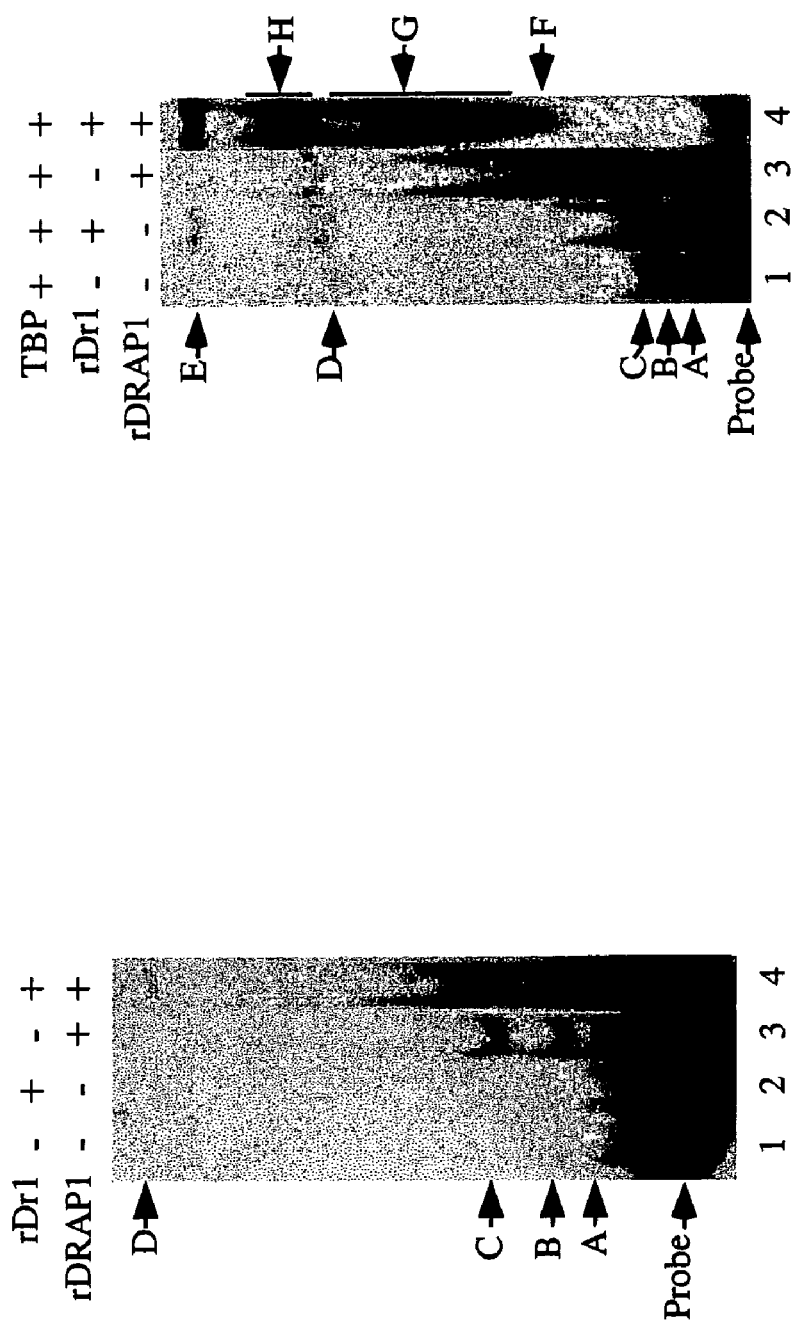

PLANT GENES ENCODING DR1 AND DRAP1, A GLOBAL REPRESSOR COMPLEX OF TRANSCRIPTION

This application is a continuation of U.S. application Ser. No. 09/789,054, filed Feb. 20, 2001, now abandoned, which is a continuation-in-part of U.S. application Ser. No. 09/485,558 filed Feb. 11, 2000, now abandoned, which was the national filing of International Application No. PCT/US98/16688 filed Aug. 12, 1998, expired, which claims the benefit of U.S. Provisional Application No. 60/055,865, filed Aug. 15, 1997, now abandoned.

FIELD OF THE INVENTION

This invention is in the field of plant molecular biology. More specifically, this invention pertains to nucleic acid fragments encoding proteins involved in regulation of gene expression in plants and seeds.

BACKGROUND OF THE INVENTION

Like many biological processes, transcription is controlled by both stimulatory and inhibitory proteins whose interplay regulates the overall activity of RNA polymerase II. The majority of regulatory proteins target specific genes through interaction with defined DNA elements in the proximity of or at a distance from the start site of transcription. In many instances, activators influence the activity of RNA polymerase II through direct or indirect interactions with the general transcription factors (Conaway and Conaway, (1993) *Annu. Rev. Biochem.* 62: 161-190; Zawel and Reinberg, (1995) *Annu. Rev. Biochem.* 64: 533-561). In cells, transcription is also negatively regulated by another family of factors. These factors repress transcription by different modes. Some are sequence-specific DNA binding proteins, which upon binding to specific promoters, render the gene silent (Hanna-Rose and Hansen, (1996) *Trends Genet.* 12: 229-234; Shi et al., (1991) *Cell* 67: 377-388). Other gene-specific repressors inhibit transcription by sequestering activators and preventing their translocation to the nucleus and/or preventing their association with promoter sequences (Benezra et al., (1990) *Cell* 61: 49-59; Baeuerle and Batimore (1988) *Science* 242: 540-545). Another growing family of repressors includes molecules that are tethered to promoters by interacting with sequence-specific DNA binding proteins and/or components of the basal transcription machinery (Ayer et al., (1995) *Cell* 80: 767-776; Inostroza et al., (1992) *Cell* 70: 477-489). One member of this last category is the Dr1/DRAP1 repressor complex.

Dr1 is a TATA-binding protein (TBP)-associated phosphoprotein and functions as an inhibitor of gene transcription (Inostroza et al., (1992) *Cell* 70: 477-489). Dr1 genes have been isolated from human, yeast, and *Arabidopsis* (Inostroza et al., (1992) *Cell* 70: 477-489; Kim et al., (1997) *Proc. Natl. Acad. Sci. USA* 94: 820-825; Kuromori et al., (1994) *Nucleic Acids Research* 22: 5296-5301). Effective repression by Dr1 requires a Dr1-associated polypeptide (DRAP1), a corepressor of transcription. Association of DRAP1 with Dr1 results in higher stability of the Dr1-TBP-TATA motif complex and precludes the entry of TFIIA and/or TFIIB to preinitiation complexes (Mermelstein et al., (1996) *Genes & Development* 10: 1033-1048). In eukaryotic systems, Dr1 and DRAP1 appear to form a heterodimer complex to repress gene transcription at the initiation complex formation (Inostroza et al., (1992) *Cell* 70: 477-489; White et al., (1994) *Science* 266: 448-450; Kim et al., (1995) *J. Biol. Chem.* 270: 10976-10981, (1996) *J. Biol. Chem.* 271: 18405-18412, (1997) *Natl. Acad. sci. USA* 94: 820-825, (2000) *Mol. Cell. Biol* 20:2455-2465; Goppelt et al., (1996) *EMBO J.* 15: 3105-3116; Gadbois et al., (1997) *Proc Natl Acad Sci USA.* 94:3145-50; Prelish (1997) *Mol. Cell. Biol.* 17: 2057-2065; Yeung et al., (1997) *Mol. Cell. Biol.* 17: 36-45; Cang et al., (1999) *EMBO J.* 18: 6662-6671; Xie et al., (2000) *EMBO J* 19: 672-682). DRAP1 genes have only been isolated from human and yeast (Mermelstein et al., (1996) *Genes & Development* 10: 1033-1048; Kim et al., (1997) *Proc. Natl. Acad. Sci. USA* 94: 820-825) and no plant DRAP1 proteins have been reported.

Accordingly, the availability of nucleic acid sequences encoding all or a portion of a Dr1 or DRAP1 transcriptional control protein would facilitate engineering, methods to alter gene expression in plants, and facilitate studies to better understand transcriptional regulation mechanisms in plants. Dr1 and DRAP1 proteins may also provide targets to facilitate design and/or identification of inhibitors of Dr1 and DRAP1 proteins that may be useful as herbicides.

SUMMARY OF THE INVENTION

The present invention concerns an isolated polynucleotide comprising: (a) a first nucleotide sequence encoding a first polypeptide comprising at least 100 amino acids, wherein the amino acid sequence of the first polypeptide and the amino acid sequence of SEQ ID NO:2 have at least 85%, 90%, or 95% identity based on the Clustal alignment method, (b) a second nucleotide sequence encoding a second polypeptide comprising at least 150 amino acids, wherein the amino acid sequence of the second polypeptide and the amino acid sequence of SEQ ID NO:34 have at least 70%, 80%, 85%, 90%, or 95% identity based on the Clustal alignment method, (c) a third nucleotide sequence encoding a third polypeptide comprising at least 180 amino acids, wherein the amino acid sequence of the third polypeptide and the amino acid sequence of SEQ ID NO: 14 have at least 70%, 80%, 85%, 90%, or 95% identity based on the Clustal alignment method, (d) a fourth nucleotide sequence encoding a fourth polypeptide comprising at least 200 amino acids, wherein the amino acid sequence of the fourth polypeptide and the amino acid sequence of SEQ ID NO:4, SEQ ID NO:6, SEQ ID NO:10, SEQ ID NO:20, or SEQ ID NO:22 have at least 70%, 80%, 85%, 90%, or 95% identity based on the Clustal alignment method, (e) a fifth nucleotide sequence encoding a fifth polypeptide comprising at least 200 amino acids, wherein the amino acid sequence of the fifth polypeptide and the amino acid sequence of SEQ ID NO:32 have at least 85%, 90%, or 95% identity based on the Clustal alignment method, (f) a sixth nucleotide sequence encoding a sixth polypeptide comprising at least 210 amino acids, wherein the amino acid sequence of the sixth polypeptide and the amino acid sequence of SEQ ID NO:28 or SEQ ID NO:40 have at least 70%, 80%, 85%, 90%, or 95% identity based on the Clustal alignment method, or (g) the complement of the first, second, third, fourth, fifth, or sixth nucleotide sequence, wherein the complement and the first, second, third, fourth, fifth, or sixth nucleotide sequence contain the same number of nucleotides and are 100% complementary. The first polypeptide preferably comprises the amino acid sequence of SEQ ID NO:2, the second polypeptide preferably comprises the amino acid sequence of SEQ ID NO:34, the third polypeptide preferably comprises the amino acid sequence of SEQ ID NO:14, the fourth polypeptide preferably comprises the amino acid sequence of SEQ ID NO:4, SEQ ID NO:6, SEQ ID NO:10, SEQ ID NO:20, or SEQ ID NO:22, the fifth polypeptide preferably comprises the amino acid sequence of SEQ ID NO:32, and the sixth polypeptide preferably comprises the amino acid sequence of SEQ ID NO:28 or SEQ ID NO:40. The first nucleotide sequence preferably comprises the nucleotide sequence of SEQ ID NO: 1, the second nucleotide sequence preferably comprises the nucleotide sequence of SEQ ID NO:33, the third nucleotide sequence preferably comprises the nucleotide sequence of SEQ ID NO:13, the fourth nucleotide sequence preferably comprises the nucleotide sequence of SEQ ID NO:3, SEQ ID NO:5, SEQ ID NO:9, SEQ ID NO: 19, or SEQ ID NO:21, the fifth nucleotide sequence preferably comprises the nucleotide sequence of SEQ ID NO:31, and the sixth nucleotide sequence preferably comprises the nucleotide sequence of SEQ ID NO:27 or SEQ ID NO:39. The first, second, third, fourth, fifth, and sixth polypeptides preferably are Dr1 or DRAP1 proteins.

In a second embodiment, the present invention relates to a chimeric gene comprising any of the isolated polynucleotides of the present invention operably linked to a regulatory sequence, and a cell, a plant, and a seed comprising the chimeric gene.

In a third embodiment, the present invention relates to a vector comprising any of the isolated polynucleotides of the present invention.

In a fourth embodiment, the present invention relates to an isolated polynucleotide fragment comprising a nucleotide sequence comprised by any of the polynucleotides of the present invention, wherein the nucleotide sequence contains at least 30, 40, or 60 nucleotides.

In a fifth embodiment, the present invention concerns an isolated polypeptide comprising: (a) a first amino acid sequence comprising at least 100 amino acids, wherein the first amino acid sequence and the amino acid sequence of SEQ ID NO:2 have at least 85%, 90%, or 95% identity based on the Clustal alignment method, (b) a second amino acid sequence comprising at least 150 amino acids, wherein the second amino acid sequence and the amino acid sequence of SEQ ID NO:34 have at least 70%, 80%, 85%, 90%, or 95% identity based on the Clustal alignment method, (c) a third amino acid sequence comprising at least 180 amino acids, wherein the third amino acid sequence and the amino acid sequence of SEQ ID NO:14 have at least 70%, 80%, 85%, 90%, or 95% identity based on the Clustal alignment method, (d) a fourth amino acid sequence comprising at least 200 amino acids, wherein the fourth amino acid sequence and the amino acid sequence of SEQ ID NO:4, SEQ ID NO:6, SEQ ID NO:10, SEQ ID NO:20, or SEQ ID NO:22 have at least 70%, 80%, 85%, 90%, or 95% identity based on the Clustal alignment method, (e) a fifth amino acid sequence comprising at least 200 amino acids, wherein the fifth amino acid sequence and the amino acid sequence of SEQ ID NO:32 have at least 85%, 90%, or 95% identity based on the Clustal alignment method, or (f) a sixth amino acid sequence comprising at least 210 amino acids, wherein the sixth amino acid sequence and the amino acid sequence of SEQ ID NO:28 or SEQ ID NO:40 have at least 70%, 80%, 85%, 90%, or 95% identity based on the Clustal alignment method. The first amino acid sequence preferably comprises the amino acid sequence of SEQ ID NO:2, the second amino acid sequence preferably comprises the amino acid sequence of SEQ ID NO:34, the third amino acid sequence preferably comprises the amino acid sequence of SEQ ID NO:14, the fourth amino acid sequence preferably comprises the amino acid sequence of SEQ ID NO:4, SEQ ID NO:6, SEQ ID NO:10, SEQ ID NO:20, or SEQ ID NO:22, the fifth amino acid sequence preferably comprises the amino acid sequence of SEQ ID NO:32, and the sixth amino acid sequence preferably comprises the amino acid sequence of SEQ ID NO:28 or SEQ ID NO:40. The polypeptide preferably is a Dr1 or DRAP1 protein.

In a sixth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a seventh embodiment, the present invention relates to a method for producing a transgenic plant comprising transforming a plant cell with any of the isolated polynucleotides of the present invention and regenerating a plant from the transformed plant cell, the transgenic plant produced by this method, and the seed obtained from this transgenic plant.

In an eighth embodiment, the present invention relates to a virus, preferably a baculovirus, comprising any of the isolated polynucleotides of the present invention or any of the chimeric genes of the present invention.

In a ninth embodiment, the invention relates to a method of selecting an isolated polynucleotide that affects the level of expression of a Dr1 or DRAP1 protein or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the Dr1 or DRAP1 protein or enzyme activity in the host cell containing the isolated polynucleotide; and (d) comparing the level of the Dr1 or DRAP1 protein or enzyme activity in the host cell containing the isolated polynucleotide with the level of the Dr1 or DRAP1 protein or enzyme activity in the host cell that does not contain the isolated polynucleotide.

In a tenth embodiment, the invention concerns a method of obtaining a nucleic acid fragment encoding a substantial portion of a Dr1 or DRAP1 protein, preferably a plant Dr1 or DRAP1 protein, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 9, 13, 19, 21, 27, 31, 33, and 39, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a Dr1 or DRAP1 protein amino acid sequence.

In an eleventh embodiment, this invention relates to a method of obtaining a nucleic acid fragment encoding all or a substantial portion of the amino acid sequence encoding a Dr1 or DRAP1 protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the Dr1 or DRAP1 protein polynucleotide in an amount sufficient to complement a null mutant to provide a positive selection means.

In a thirteenth embodiment, this invention relates to a method of altering the level of expression of a Dr1 or DRAP1 protein in a host cell comprising: (a) transforming a host cell with a chimeric gene of the present invention; and (b) growing the transformed host cell under conditions that are suitable for expression of the chimeric gene wherein expression of the chimeric gene results in production of altered levels of the Dr1 or DRAP1 protein in the transformed host cell.

In a fourteenth embodiment, this invention relates to a method for evaluating at least one compound for its ability to inhibit the activity of a protein involved in regulation of gene expression, the method comprising the steps of: (a) transforming a host cell with a chimeric gene comprising a nucleic acid fragment encoding a protein involved in regulation of gene expression, operably linked to suitable regulatory sequences; (b) growing the transformed host cell under conditions that are suitable for expression of the chimeric gene wherein expression of the chimeric gene results in production of the protein involved in regulation of gene expression in the transformed host cell; (c) optionally purifying the protein involved in regulation of gene expression expressed by the transformed host cell; (d) treating the protein involved in regulation of gene expression with a compound to be tested; and (e) comparing the activity of the protein involved in regulation of gene expression that has been treated with a test compound to the activity of an untreated protein involved in regulation of gene expression, and selecting compounds with potential for inhibitory activity.

BRIEF DESCRIPTION OF THE DRAWINGS AND SEQUENCE LISTINGS

The invention can be more fully understood from the following detailed description and the accompanying drawings and Sequence Listing which form a part of this application.

FIGS. 1A, 1B and 1C depict the amino acid sequence alignment between the Dr1 proteins encoded by the nucleotide sequences derived from corn clone p0117.chclp58r (SEQ ID NO:4), corn clone p0127.cntam51r (SEQ ID NO:6), contig assembled using sequences derived from rice clone rl0n.pk0076.g1 and PCR-generated fragment (SEQ ID NO:10), soybean clone ses2w.pk0043.b3 (SEQ ID NO:14), wheat clone w1e1n.pk0106.g11 (SEQ ID NO:20), and wheat clone wre1n.pk0037.b4 (SEQ ID NO:22), and an *Arabidopsis thaliana* Dr1protein (NCBI GenBank Identifier (GI) No. 1352316; SEQ ID NO:41). Amino acids which are conserved among all and at least two sequences with an amino acid at that position are indicated with an asterisk (*). Dashes are used by the program to maximize alignment of the sequences.

FIGS. 2A and 2B depict the amino acid sequence alignment between the DRAP1 proteins encoded by the nucleotide sequences derived from corn clone cbn2.pk0039.h8 (SEQ ID NO:28), rice clone rls12.pk0015.e12 (SEQ ID NO:32), soybean clone sdp4c.pk031.p18 (SEQ ID NO:34), and wheat clone wlm1.pk0016.f3 (SEQ ID NO:40), and the Homo sapiens DRAP1 protein (NCBI GI No. 7513394; SEQ ID NO:42). Amino acids which are conserved among all and at least two sequences with an amino acid at that position are indicated with an asterisk (*). Dashes are used by the program to maximize alignment of the sequences.

FIG. 3 shows the results of the rice genomic DNA blot analyses done to determine the number of Dr1 and DRAP1 genes in the rice genome. Total rice genomic DNA samples were digested with the indicated restriction enzymes, separated on an 1% agarose gel, blotted onto a membrane and hybridized with $^{32}$P-labeled DNA containing the coding region of rice Dr1 (panel A) or rice DRAP1 (panel B) genes. Numbers on the left of each panel indicate the position of the indicated DNA size markers.

Figure 4C:
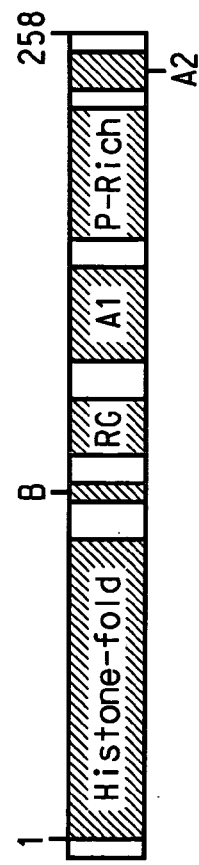

FIG. 4 shows different aspects of the yeast two-hybrid experiment designed to analyze the interaction between rice Dr1 (rDr1) and rice DRAP1 (rDRAP1) in yeast. FIG. 4A is a schematic representation of the pBDGal4::rDRAP1 and pADGal4::rDr1 constructs. Gal4BD and Gal4AD indicate Gal4 DNA binding domain and Gal4 activation domain, respectively. The coding regions of rice DRAP1 and rice Dr1 were fused inframe with the coding regions for Gal4 binding domain in pBD-Gal4 Cam (Strategene, San Diego, Calif.) and Gal4 activation domain in pAD-Gal4-2.1 (Strategene, San Diego, Calif.), respectively, to produce pBDGal4::rDRAP1 and pADGal4::rDr1, respectively. The EcoR I and Sma I fragment containing the coding region of rice Dr1 was cloned into pAD-Gal4 EcoR I and Sma I sites to generate pADGal4::rDr1. The Mfe I and Pst I fragment containing the coding region of rice DRAP1 was cloned into pBD-Gal4 EcoR I and Pst I sites to generate pBDGal4::rDRAP1. FIG. 4B indicates the growth of yeast transformed with different constructs in different growth media. Yeast cells were transformed with pBDGal4::rDrAp1, pADGal4::rDr1, or pBD-Gal4::rDrAp1 plus pADGal4: :rDr1 (marked as BD, AD, and BD+AD, respectively). The yeast cells were grown on selection media as indicated. FIG. 4C summarizes the interaction of different versions of rice DRAP1 with rice Dr1. The left side is a schematic representation of the rice DRAP1 deletion mutants in pBDGal4::rDRAP1 constructs. The right side indicates the interaction of these mutants with rice Dr1. "Histone-fold" refers to histone-fold-like domain, "B" refers to basic amino acid-rich motif, "RG" stands for arginine and glycine repeat, "A1" stands for acidic amino acid-rich domain 1, "P-rich" stands for proline-rich domain, and "A2" stands for acidic amino acid-rich domain 2. "1" and "258" indicate the amino acid residue in the encoded protein.

Figure 5A:
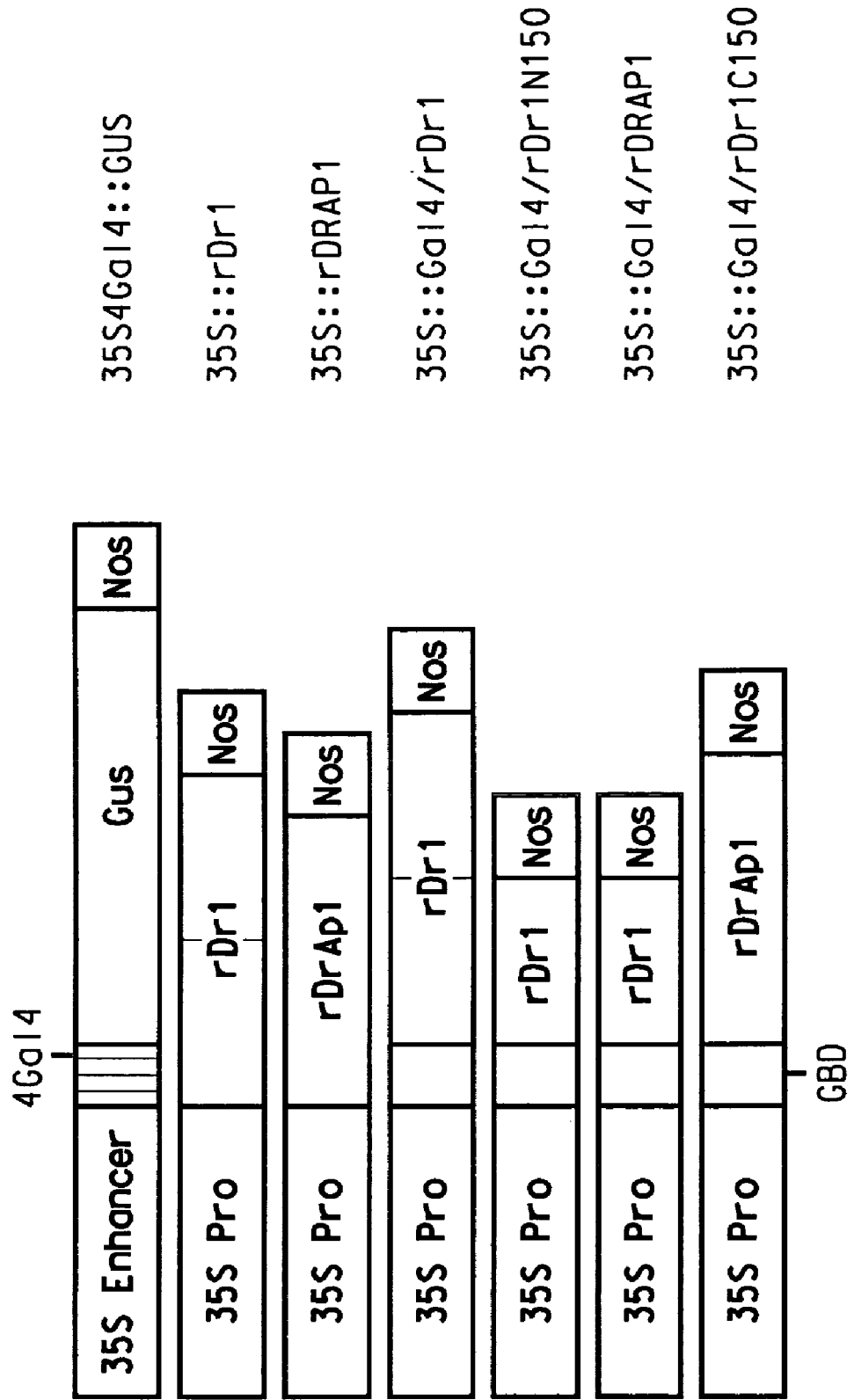
Figure 5B:
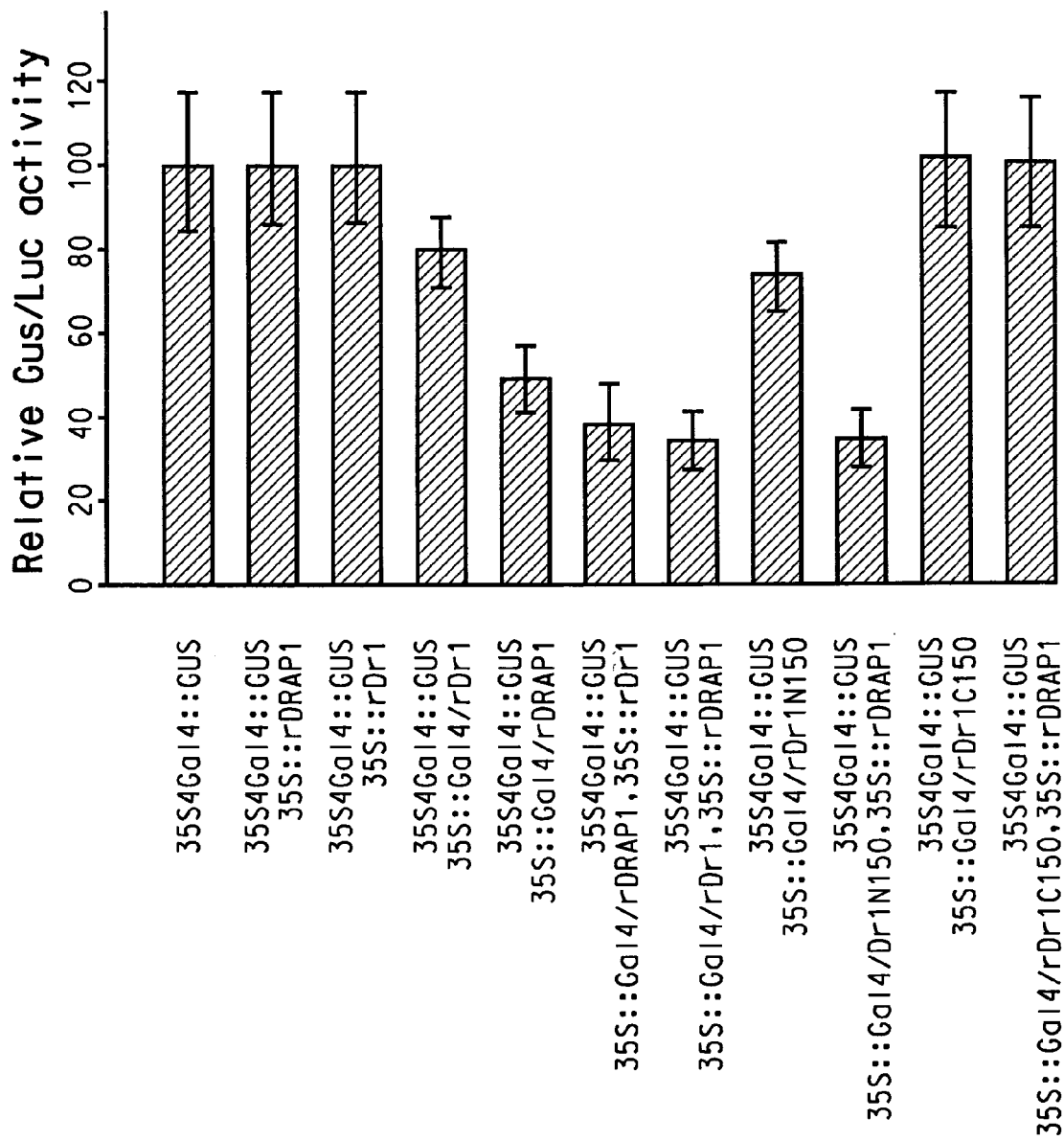

FIG. 5 indicates the results of the tobacco protoplast transfection assays designed to elucidate regions important for rice Dr1 and rice DRAP1 function in vivo. These results also indicate that rice Dr1 and rice DRAP1 function as repressors in vivo in plant cells. FIG. 5A is a schematic representation of the reporter and the effectors used for protoplast transfection. In the figure, 35S enhancer refers to −832 to −50 region of CaMV35S promoter, 35S Pro stands for CaMV35S promoter, 4Gal4 stands for four Gal4 binding sites, Nos stands for the nos 3' sequence that serves as terminator, GBD stands for Gal4 DNA-binding domain, GUS stands for GUS coding region, rDRAP1 stands for rice DRAP1 coding region, and rDr1 stands for rice Dr1 coding region. FIG. 5B indicates the relative GUS/Luciferase activity ratios in protoplasts transfected with the different plasmid combinations as indicated. 100% is the GUS/Luciferase activity ratio obtained with p35S4Gal4::GUS. Indicated are the means and the standard deviations (horizontal bars) for each plasmid combination calculated from nine independent samples. p35S::Luc was co-transfected with all the plasmid combinations indicated. Luciferase activity (derived from p35S::Luc) was used as internal control for the transfection experiments to take into account variability in transfection efficiency.

Figure 6A:
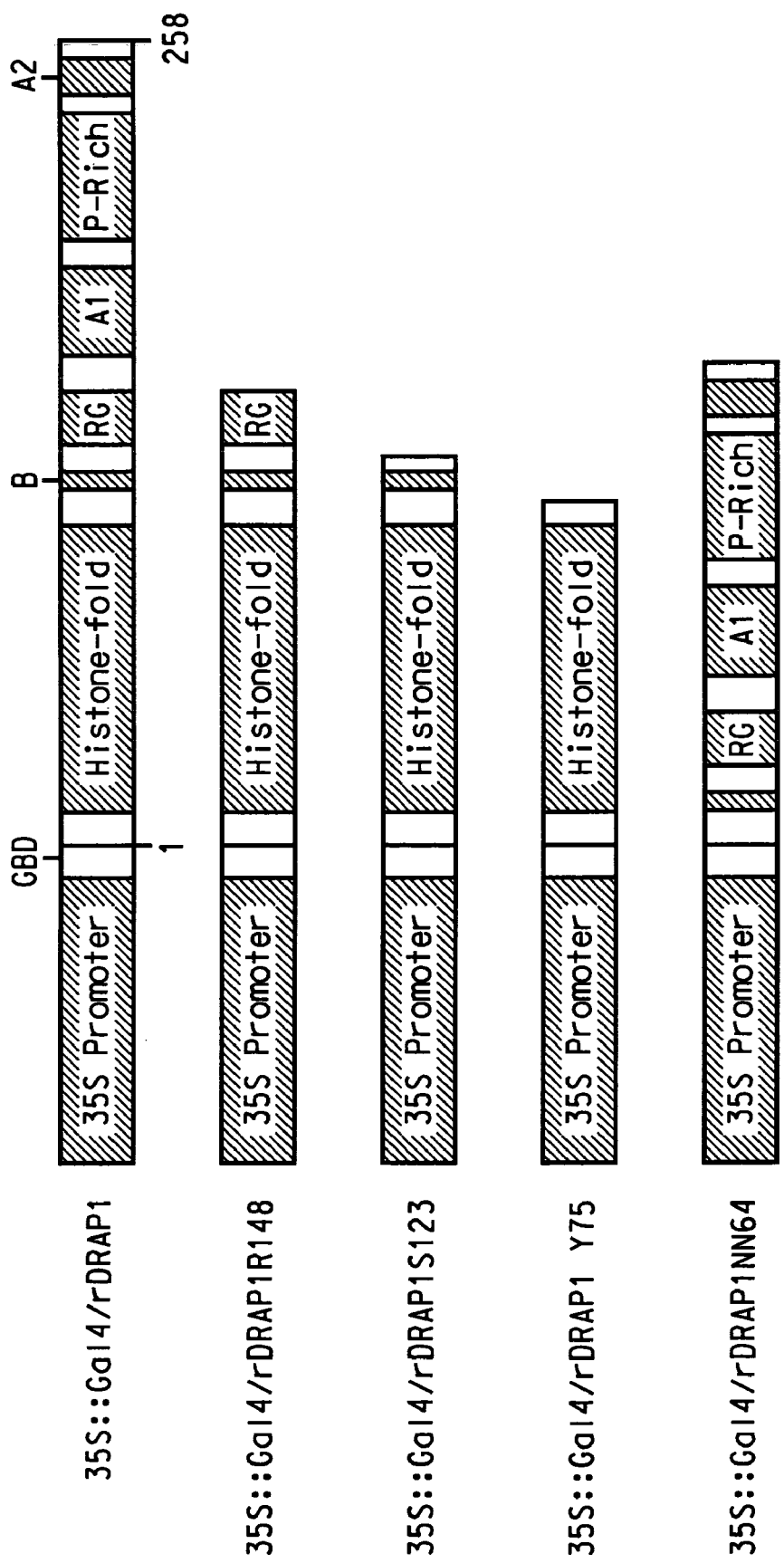
Figure 6B:
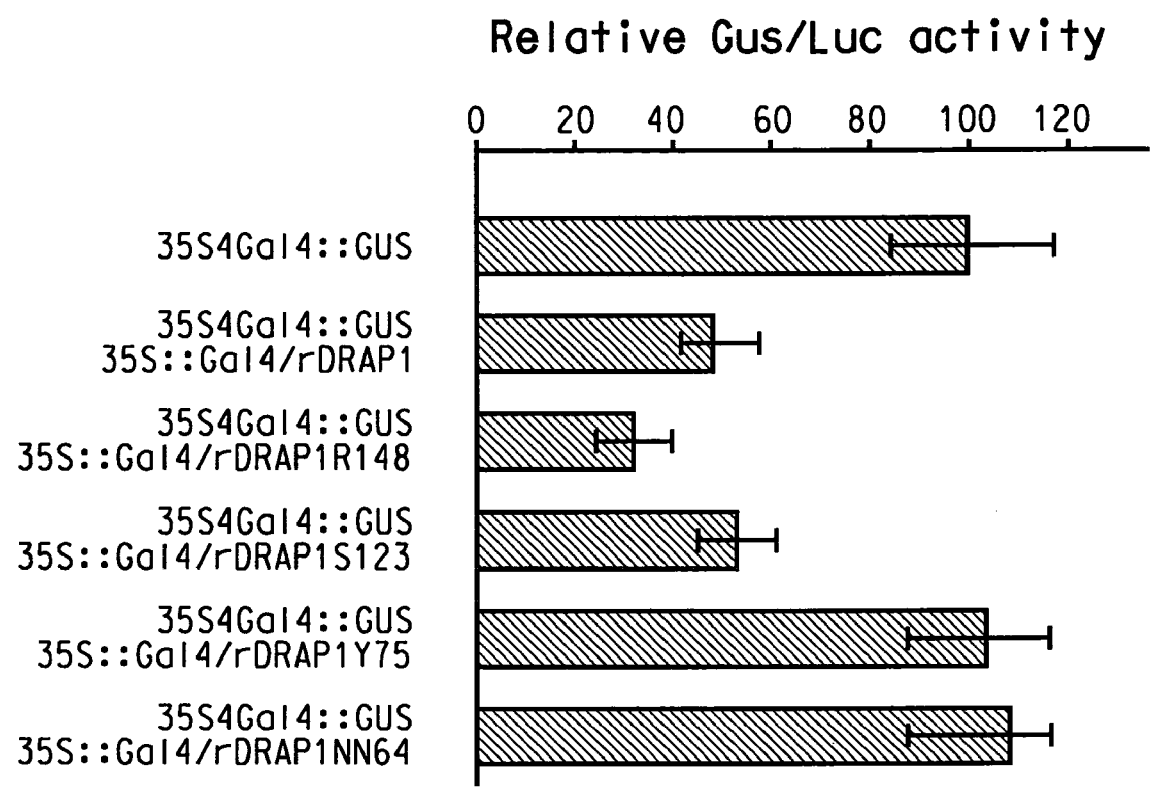

FIG. 6 indicates the results of the tobacco protoplast transfection assays designed to elucidate regions important for rice DRAP1 function in vivo. FIG. 6A is a schematic representation of the rice DRAP1 deletion mutants encoded by the constructs thus indicated. The different regions in the constructs are labeled in the same manner as the constructs in FIG. 4C. GBD as in FIG. 5A stands for Gal4 DNA-binding domain. FIG. 6B indicates the relative Gus/Luc activity ratios in protoplasts transfected with the different plasmids as indicated. 100% is the GUS/Luciferase activity ratio obtained with p35S4Gal4::GUS. Indicated are the means and the standard deviations (horizontal bars) for each plasmid combination calculated from nine independent samples. p35S::Luc was co-transfected with all the plasmid combinations indicated. Luciferase activity (derived from p35S::Luc) was used as internal control for the transfection experiments to take into account variability in transfection efficiency.

Figure 7A:
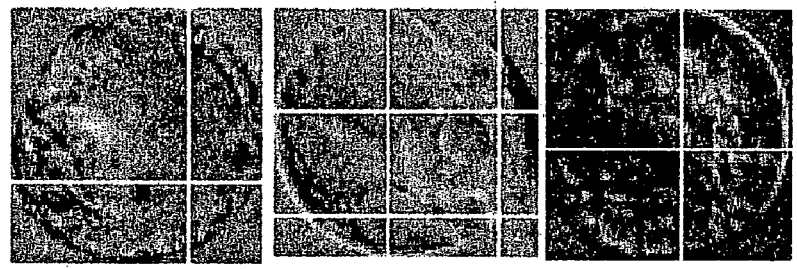
Figure 7B:
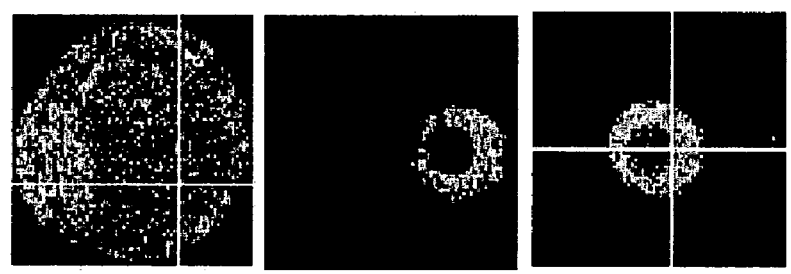

FIG. 7 indicates where rDr1/mGFP and rDRAP1/mGFP are localized in tobacco NT-1 cells. FIG. 7A is a schematic representation of the proteins encoded by the constructs in pRTL2-mGFP, p35S::rDr1/mGFP and p35S::rDRAP1/mGFP which were used for transfection of tobacco NT-1 cells. FIG. 7B indicates the subcellular localization of mGFP, rDr1/mGFP, and rDRAP1/mGFP in tobacco NT-1 cells. DIC is the differential interference contrast image whereas GFP is the mGFP fluorescence image of the same cell transfected with the indicated construct. Light spots in the GFP image indicate where the GFP protein is localized.

FIG. 8 shows the results of gel shift assays which demonstrate interaction of recombinant rDr1 and rDRAP1 with rTBP-DNA complex. DNA-protein interaction products were separated on 5% native polyacrylmide gels. rDRAP1 (100 ng), rDr1 (250 ng) and rTBP (100 ng) were present (+) or absent (−) in the reactions as indicated. FIG. 8A shows that recombinant rDRAP1 binds to DNA, whereas FIG. 8B shows that recombinant rDr1 and rDRAP1 interact with rTBP-DNA complex. The figure is discussed at length in Example 11.

Figure 9:
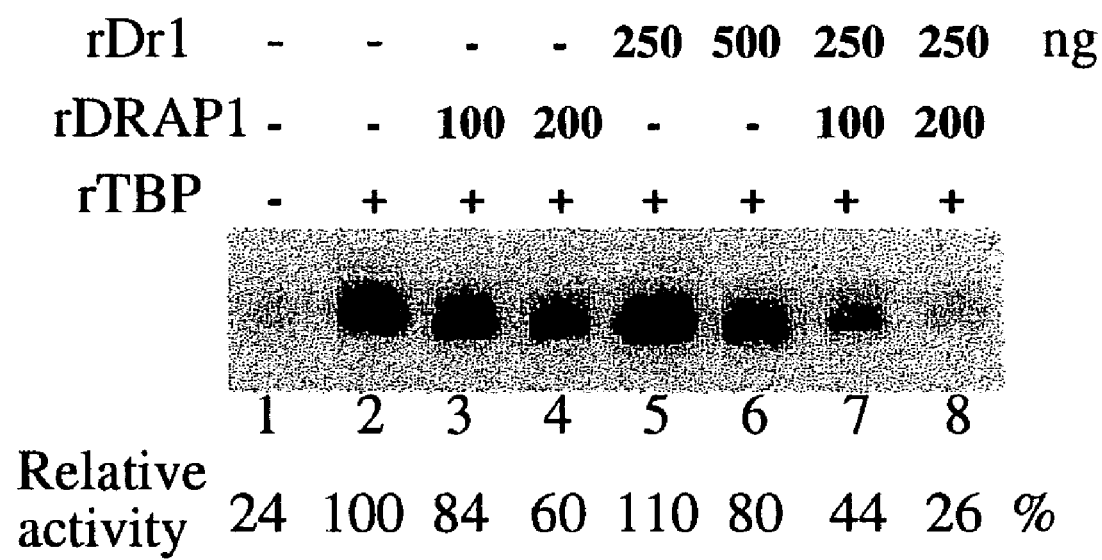

FIG. 9 demonstrates the transcriptional repression activities of rDr1 and rDRAP1 in vitro. Recombinant rTBP (50 ng), rDr1 (as indicated, in nanograms) and rDRAP1 (as indicated, in nanograms) were added into the in vitro transcription mixture containing buffer and rice PAL promoter/Gus gene fusion as template (Zhu et al.(1995) *Plant J* 5:1021-1030) 10 min prior to the addition of rice whole cell extracts (Zhu et al.(1995) *Plant J* 5:1021-1030). The transcript level of each reaction was measured by primer extension analysis, and expressed as percent of transcript level obtained with TBP added but no rDr1 and rDRAP1 (relative activity). The products of primer extension reactions were separated on an 8% polyacrylamide denature gel.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs or PCR fragment sequence ("Contig*"), or sequences encoding the entire protein derived from an FIS, a contig, or an FIS and PCR fragment sequence ("CGS"). SEQ ID NOs:7, 8, 11, 12, 15, 16, 17, 18, 23, 24, 25, 26, 29, 30, 35, 36, 37, and 38 presented herein correspond to SEQ ID NOs:5, 6, 7, 8, 18, 19, 9, 10, 16, 17, 1, 2, 3, 4, 20, 21, 11, and 12, respectively, presented in U.S. application Ser. No. 09/485,558 filed Feb. 11, 2000. The sequence descriptions and Sequence Listing attached hereto comply with the rules governing nucleotide and/or amino acid sequence disclosures in patent applications as set forth in 37 C.F.R. §1.821-1.825.

TABLE 1

Proteins Involved in Regulation of Gene Expression

| Protein (Plant Source) | Clone Designation | Status | SEQ ID NO: (Nucleotide) | SEQ ID NO: (Amino Acid) |
|---|---|---|---|---|
| Dr1 (Corn) | p0002.cgeuz33r | EST | 1 | 2 |
| Dr1 (Corn) | p0117.chclp58r (FIS) | CGS | 3 | 4 |
| Dr1 (Corn) | p0127.cntam51r (FIS) | CGS | 5 | 6 |
| Dr1 (Rice) | rl0n.pk0076.g1 | EST | 7 | 8 |
| Dr1 (Rice) | Contig of rl0n.pk0076.g1 (FIS) PCR fragment sequence | CGS | 9 | 10 |
| Dr1 (Soybean) | ses2w.pk0043.b3 | EST | 11 | 12 |
| Dr1 (Soybean) | ses2w.pk0043.b3 (FIS) | CGS | 13 | 14 |
| Dr1 (Soybean) | se3.o8b05 (FIS) | CGS | 15 | 16 |
| Dr1 (Wheat) | wle1n.pk0106.g11 | EST | 17 | 18 |
| Dr1 (Wheat) | wle1n.pk0106.g11 (FIS) | CGS | 19 | 20 |
| Dr1 (Wheat) | wre1n.pk0037.b4 (FIS) | CGS | 21 | 22 |
| DRAP1 (Corn) | cs1.pk0049.a1 (FIS) | CGS | 23 | 24 |
| DRAP1 (Corn) | cbn2.pk0039.h8 | EST | 25 | 26 |
| DRAP1 (Corn) | cbn2.pk0039.h8 (FIS) | CGS | 27 | 28 |
| DRAP1 (Rice) | rls12.pk0015.e12 | EST | 29 | 30 |
| DRAP1 (Rice) | rls12.pk0015.e12 (FIS) | CGS | 31 | 32 |
| DRAP1 (Soybean) | sdp4c.pk031.p18 (FIS) | CGS | 33 | 34 |
| DRAP1 (Wheat) | wl1.pk0012.f3 | EST | 35 | 36 |
| DRAP1 (Wheat) | wlm1.pk0016.f3 | EST | 37 | 38 |
| DRAP1 (Wheat) | wlm1.pk0016.f3 | FIS | 39 | 40 |

Sequence analysis showed that the insert in clone wlm1.pk0016.f3 encodes an entire protein except for the start methionine the coding sequence for which can easily be introduced by site-directed mutagenesis, PCR, or cloning into an expression vector using methods well-known in the art.

SEQ ID NO:43 is a rice Dr1 gene-specific oligonucleotide used for first strand cDNA synthesis.

SEQ ID NOs:44-46 are PCR primers used to isolate the 5' end of rice Dr1 cDNA.

SEQ ID NO:47 is a rice Dr1 gene-specific oligonucleotide used for first strand cDNA synthesis.

SEQ ID NOs:48-50 are PCR primers used to isolate full-length rice Dr1 cDNA.

SEQ ID NOs:51-52 are PCR primers used to amplify the enhancer fragment (−832 to −50) of CaMV35S promoter.

SEQ ID NOs:53-54 are oligonucleotide primers used to introduce NcoI and XhoI sites, respectively, into rice DRAP1 cDNA.

SEQ ID NOs:55-56 are PCR primers used to amplify the coding region of rice DRAP1 cDNA.

SEQ ID NO:57 is an oligonucleotide primer used to introduce a MscI site at the codon encoding residue 150 of rice Dr1.

SEQ ID NOs:58-59 are PCR primers used to amplify the coding region of luciferase gene.

SEQ ID NO:60 is an oligonucleotide primer used to introduce a MfeI site into p35S::Gal4/rDRAP1.

SEQ ID NOs:61-63 are oligonucleotide primers used to introduce EcoRV sites into p35S::Gal4/rDRAP1.

SEQ ID NOs:64-65 are PCR primers used to amplify the coding region of rice DRAP1.

SEQ ID NO:66 is the nucleotide sequence of a cDNA encoding a rice TATA-binding protein (TBP).

SEQ ID NO:67 is the amino acid sequence of the protein encoded by the nucleotide sequence set forth in SEQ ID NO:66.

SEQ ID NOs:68-69 are oligonucleotide primers used to introduce NcoI and XhoI sites, respectively, in rice TBP cDNA.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides derived from SEQ ID NOs:1, 3, 5, 9, 13, 19, 21, 27, 31, 33, or 39, or the complement of such sequences.

The term "isolated" polynucleotide refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-á-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic acid fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 9, 13, 19, 21, 27, 31, 33, and 39, and the complement of such nucleotide sequences may be used in methods of selecting an isolated polynucleotide that affects the expression of a Dr1 or DRAP1 protein in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, RL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 or 180 amino acids, still more preferably at least 200 or 210 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al, (1993) *J. Mol. Biol.* 215:403-410 . In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3'non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis") and in Ausubel et al. *Current Protocols in Molecular Biology*; Wiley, New York, 1987.

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising: (a) a first nucleotide sequence encoding a first polypeptide comprising at least 100 amino acids, wherein the amino acid sequence of the first polypeptide and the amino acid sequence of SEQ ID NO:2 have at least 85%, 90%, or 95% identity based on the Clustal alignment method, (b) a second nucleotide sequence encoding a second polypeptide comprising at least 150 amino acids, wherein the amino acid sequence of the second polypeptide and the amino acid sequence of SEQ ID NO:34 have at least 70%, 80%, 85%, 90%, or 95% identity based on the Clustal alignment method, (c) a third nucleotide sequence encoding a third polypeptide comprising at least 180 amino acids, wherein the amino acid sequence of the third polypeptide and the amino acid sequence of SEQ ID NO:14 have at least 70%, 80%, 85%, 90%, or 95% identity based on the Clustal alignment method, (d) a fourth nucleotide sequence encoding a fourth polypeptide comprising at least 200 amino acids, wherein the amino acid sequence of the fourth polypeptide and the amino acid sequence of SEQ ID NO:4, SEQ ID NO:6, SEQ ID NO:10, SEQ ID NO:20, or SEQ ID NO:22 have at least 70%, 80%, 85%, 90%, or 95% identity based on the Clustal alignment method, (e) a fifth nucleotide sequence encoding a fifth polypeptide comprising at least 200 amino acids, wherein the amino acid sequence of the fifth polypeptide and the amino acid sequence of SEQ ID NO:32 have at least 85%, 90%, or 95% identity based on the Clustal alignment method, (f) a sixth nucleotide sequence encoding a sixth polypeptide comprising at least 210 amino acids, wherein the amino acid sequence of the sixth polypeptide and the amino acid sequence of SEQ ID NO:28 or SEQ ID NO:40 have at least 70%, 80%, 85%, 90%, or 95% identity based on the Clustal alignment method, or (g) the complement of the first, second, third, fourth, fifth, or sixth nucleotide sequence, wherein the complement and the first, second, third, fourth, fifth, or sixth nucleotide sequence contain the same number of nucleotides and are 100% complementary. The first polypeptide preferably comprises the amino acid sequence of SEQ ID NO:2, the second polypeptide preferably comprises the amino acid sequence of SEQ ID NO:34, the third polypeptide preferably comprises the amino acid sequence of SEQ ID NO: 14, the fourth polypeptide preferably comprises the amino acid sequence of SEQ ID NO:4, SEQ ID NO:6, SEQ ID NO:10, SEQ ID NO:20, or SEQ ID NO:22, the fifth polypeptide preferably comprises the amino acid sequence of SEQ ID NO:32, and the sixth polypeptide preferably comprises the amino acid sequence of SEQ ID NO:28 or SEQ ID NO:40. The first nucleotide sequence preferably comprises the nucleotide sequence of SEQ ID NO:1, the second nucleotide sequence preferably comprises the nucleotide sequence of SEQ ID NO:33, the third nucleotide sequence preferably comprises the nucleotide sequence of SEQ ID NO:13, the fourth nucleotide sequence preferably comprises the nucleotide sequence of SEQ ID NO:3, SEQ ID NO:5, SEQ ID NO:9, SEQ ID NO:19, or SEQ ID NO:21, the fifth nucleotide sequence preferably comprises the nucleotide sequence of SEQ ID NO:31, and the sixth nucleotide sequence preferably comprises the nucleotide sequence of SEQ ID NO:27 or SEQ ID NO:39. The first, second, third, fourth, fifth, and sixth polypeptides preferably are Dr1 or DRAP1 proteins.

Nucleic acid fragments encoding at least a portion of several proteins involved in regulation of gene expression have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other Dr1 or DRAP1 proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 9, 13, 19, 21, 27, 31, 33, and 39, and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a Dr1 or DRAP1 polypeptide, preferably a substantial portion of a plant Dr1 or DRAP1 polypeptide, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 9, 13, 19, 21, 27, 31, 33, and 39, and the complement of such nucleotide sequences; and amplifying a nucleic acid fragment (preferably a cDNA inserted in a cloning vector) using the oligonucleotide primer. The amplified nucleic acid fragment preferably will encode a portion of a Dr1 or DRAP1 polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of gene transcription in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.*100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective.

In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns an isolated polypeptide comprising: (a) a first amino acid sequence comprising at least 100 amino acids, wherein the first amino acid sequence and the amino acid sequence of SEQ ID NO:2 have at least 85%, 90%, or 95% identity based on the Clustal alignment method, (b) a second amino acid sequence comprising at least 150 amino acids, wherein the second amino acid sequence and the amino acid sequence of SEQ ID NO:34 have at least 70%, 80%, 85%, 90%, or 95% identity based on the Clustal alignment method, (c) a third amino acid sequence comprising at least 180 amino acids, wherein the third amino acid sequence and the amino acid sequence of SEQ ID NO: 14 have at least 70%, 80%, 85%, 90%, or 95% identity based on the Clustal alignment method, (d) a fourth amino acid sequence comprising at least 200 amino acids, wherein the fourth amino acid sequence and the amino acid sequence of SEQ ID NO:4, SEQ ID NO:6, SEQ ID NO:10, SEQ ID NO:20, or SEQ ID NO:22 have at least 70%, 80%, 85%, 90%, or 95% identity based on the Clustal alignment method, (e) a fifth amino acid sequence comprising at least 200 amino acids, wherein the fifth amino acid sequence and the amino acid sequence of SEQ ID NO:32 have at least 85%, 90%, or 95% identity based on the Clustal alignment method, or (f) a sixth amino acid sequence comprising at least 210 amino acids, wherein the sixth amino acid sequence and the amino acid sequence of SEQ ID NO:28 or SEQ ID NO:40 have at least 70%, 80%, 85%, 90%, or 95% identity based on the Clustal alignment method. The first amino acid sequence preferably comprises the amino acid sequence of SEQ ID NO:2, the second amino acid sequence preferably comprises the amino acid sequence of SEQ ID NO:34, the third amino acid sequence preferably comprises the amino acid sequence of SEQ ID NO:14, the fourth amino acid sequence preferably comprises the amino acid sequence of SEQ ID NO:4, SEQ ID NO:6, SEQ ID NO:10, SEQ ID NO:20, or SEQ ID NO:22, the fifth amino acid sequence preferably comprises the amino acid sequence of SEQ ID NO:32, and the sixth amino acid sequence preferably comprises the amino acid sequence of SEQ ID NO:28 or SEQ ID NO:40. The polypeptide preferably is a Dr1 or DRAP1 protein.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded protein involved in regulation of gene expression. An example of a vector for high level expression of the instant polypeptides in a bacterial host is provided (Example 9).

Additionally, the instant polypeptides can be used as a target to facilitate design and/or identification of inhibitors of those enzymes that may be useful as herbicides. This is desirable because the polypeptides described herein are involved in regulation of gene expression. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Examples 1

Composition of cDNA Libraries, Isolation and Sequencing of cDNA Clones cDNA libraries representing mRNAs from various corn (*Zea mays*), rice (*Oryza saliva*), soybean (Glycine max), and wheat (*Triticum aestivum*) tissues were prepared. The characteristics of the libraries are described below. Corn developmental stages are explained in the publication "How a corn plant develops" from the Iowa State University Coop. Ext. Service Special Report No. 48 reprinted June 1993.

sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a

TABLE 2 cDNA Libraries from Corn, Rice, Soybean, and Wheat

| Library | Tissue | Clone |
| --- | --- | --- |
| cbn2 | Corn Developing Kernel Two Days After Pollination | cbn2.pk0039.h8 |
| cs1 | Corn Leaf Sheath From 5 Week Old Plant | cs1.pk0049.a1 |
| p0002 | Corn Tassel: Premeiotic Cells to Early Uninucleate Stage | p0002.cgeuz33r |
| p0117 | Corn Expanding Internode: Plants Sampled at the V10 Stage; Internodes 5–9 (Upper 4–5 Expanding Internodes)* | p0117.chc1p58r |
| p0127 | Corn Nucellus Tissue, 5 Days After Silking* | p0127.cntam51r |
| rl0n | Rice 15 Day Old Leaf* | rl0n.pk0076.g1 |
| rls12 | Susceptible Rice Leaf 15 Days After Germination, 12 hours After Infection of Strain *Magnaporthe grisea* 4360-R-67 (AVR2-YAMO) | rls12.pk0015.e12 |
| sdp4c | Soybean Developing Pod (10–12 mm) | sdp4c.pk031.p18 |
| se3 | Soybean Embryo, 17 Days After Flowering | se3.o8b05 |
| ses2w | Soybean Embryogenic Suspension 2 Weeks After Subculture | ses2w.pk0043.b3 |
| wl1 | Wheat Leaf From 7 Day Old Light Grown Seedling | wl1.pk0012.f3 |
| wle1n | Wheat Leaf From 7 Day Old Etiolated Seedling* | wle1n.pk0106.g11 |
| wlm1 | Wheat Seedling 1 Hour After Inoculation With *Erysiphe graminis f. sp tritici* | wlm1.pk0016.f3 |
| wre1n | Wheat Root From 7 Day Old Etiolated Seedling* | wre1n.pk0037.b4 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding proteins involved in regulation of gene expression were identified by conducting BLAST (Basic Local Alignment Search Tool; Altschul et al. (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet. 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389-3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Dr1 Proteins

The insert in clones r10n.pk0076.g1, ses2w.pk0043.b3, se3.o8b05, and w1e1n.pk0106.g11 had been previously determined to encode Dr1 protein (WO 99/09175). The sequence of the entire cDNA insert in clones r10n.pk0076.g1, ses2w.pk0043.b3, and w1e1n.pk0106.g11 was determined. Further sequencing and searching of the DuPont proprietary database allowed the identification of other corn and wheat clones encoding Dr1 protein. The BLASTX search using the EST sequences from clones listed in Table 3 revealed similarity of the polypeptides encoded by the cDNAs to Dr1 proteins from *Arabidopsis thaliana* (NCBI GenBank Identifier (GI) Nos. 11279032, 8346556, and 1352316). Shown in Table 4 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences encoding the entire protein derived from an FIS, a contig, or an FIS and PCR fragment sequence ("CGS"):

TABLE 3

BLAST Results for Sequences Encoding Polypeptides Homologous to Dr1 Protein

| | | BLAST Results | |
|---|---|---|---|
| Clone | Status | NCBI GI No. | pLog Score |
| p0002.cgeuz33r | EST | 1352316 | 48.20 |
| p0117.chclp58r (FIS) | CGS | 11279032 | 60.22 |
| p0127.cntam51r (FIS) | CGS | 8346556 | 61.30 |
| Contig of r10n.pk0076.g1 (FIS) PCR fragment sequence | CGS | 1352316 | 59.40 |
| ses2w.pk0043.b3 (FIS) | CGS | 1352316 | 67.70 |
| w1e1n.pk0106.g11 (FIS) | CGS | 1352316 | 59.30 |
| wre1n.pk0037.b4 (FIS) | CGS | 1352316 | 59.30 |

The insert in clone r10n.pk0076.g1 was found to encode a truncated rice Dr1 protein, and to contain two unspliced introns (1082 bp and 84 bp). Using 5'-RACE and RT-PCR techniques which are well-known in the art, the corresponding full-length cDNA was isolated (SEQ ID NO:9). The 5' end of rice Dr1 cDNA was amplified according to the instruction of 5' RACE system (Gibco BRL, Rockville, Md.). In brief, total RNA was extracted using RNA purification kit (Qiagen, Valencia, Calif.) according to the instructions of the manufacturer (Qiagen, Valencia, Calif.). First strand cDNA was synthesized using 3.5 µg total RNA isolated from rice suspension cells and rice Dr1 gene-specific oligonucleotide Q142 (SEQ ID NO:43) as primer.

```
Q142:
5'-GTTGCTCAGCTACAGCTTGTTCC-3'    (SEQ ID NO: 43)
```

The product of the first strand cDNA synthesis reaction was used as template for PCR reactions using rice Dr1 gene specific-oligonucleotide Q143 (SEQ ID NO:44) and Abridged anchor primer (SEQ ID NO:45) (Gibco BRL, Rockville, Md.) as primers.

```
Q143:
5'-TTGGAGAATCCAGGGTATCATGC-3'    (SEQ ID NO: 44)

Abridged anchor primer:
5'-GGCCACGCGTCGACTAGTACGGGIIG    (SEQ ID NO: 45)
GGIIGGGIIG-3'
```

In SEQ ID NO:45 above, T stands for inosine.

The PCR reaction was electrophoresed through an agarose gel and a 350-bp PCR product that was the right size was detected. The 350 bp DNA fragment was isolated from the agarose gel and used as template for second round PCR amplification using rice Dr1 gene-specific oligonucleotide Q144 (SEQ ID NO:46) and Abridged anchor primer (SEQ ID NO:45) as primers.

Q144: 5'-CAAGTCGACGGCCGCTTGAACCTCTTC-3' (SEQ ID NO:46)

The 350 bp DNA fragment from second round PCR was cloned into pre-cut blunt-end pGEM-T vector (Promega). DNA sequence confirmed that the 350 bp DNA fragment encodes the 5' end of rice Dr1 cDNA.

To isolate full-length rice Dr1 cDNA, 3.5 µg of total RNA was used for first strand cDNA synthesis using rice Dr1 gene-specific oligonucleotide Q148 (SEQ ID NO:47) as primer.

Q148: 5'-CTTATACTGAGGCTACACAAC-3' (SEQ ID NO:47)

The product of first strand cDNA synthesis reaction was used for PCR reaction using oligonucleotides Q149 (SmaI site-containing Dr1 gene-specific oligonucleotide) (SEQ ID NO:48) and Q151 (SEQ ID NO:49) as primers.

```
Q149:
5'-ATACCCGGGTGAACTGTCCAAGCC    (SEQ ID NO: 48)
ATGTTC-3'

Q151:
5'-GTTAGGTGTCGCGCCTGGAGA-3'    (SEQ ID NO: 49)
```

The PCR products were then used for second round PCR using Q149 (SEQ ID NO:48) and Q150 (EcoRI site-containing Dr1 gene-specific oligonucleotide) (SEQ ID NO:50) as primers.

Q150: 5'-TAAGAATTCATGGATCCGATGGATATCGTG-3' (SEQ ID NO:50)

The oligonucleotides Q150 and Q149 were designed to cover the translation initiation codon and translation stop codon respectively. The 900 bp PCR product was cloned into pre-cut blunt-end pGEM-T giving rise to pGEM-rDr1. DNA sequence confirmed that the insert encodes a full length cDNA of rice Dr1.

The coding region in the cDNA is 891 bp in length and encodes a polypeptide of 296 amino acids (SEQ ID NO:10) with a calculated molecular weight of 33.7 kDa. The Dr1 protein encoded by the insert in wheat clone wre1n.pk0037.b4 is similar in length, with 312 amino acids (SEQ ID NO:22) and a calculated molecular weight of 35 kDa. Both the rice and wheat Dr1 proteins have an extra glutamine and proline-rich domain located from residue 253 to 288. The glutamine and proline-rich domain of transcription factors are usually involved in protein-protein interactions. Like the Dr1 protein from all other systems (Inostroza et al. (1992) Cell 70:477-489; Kim et al. (1997) Proc Natl Acad Sci USA 94:820-825), the N-terminal region of the rice Dr1 protein has a histone fold-like structure located from residue 12 to 96 (Baxevanis and Landsman (1998) Nucl Acids Res 26:372-375), which may be involved in interaction with DRAP1 protein (Goppelt et al. (1996) EMBO J. 15:3105-3116; Mermelstein et al. (1996) Genes Dev 10:1033-1048; Yeung et al. (1997) Mol Cell Biol 17:36-45).

FIGS. 1A-1C present an alignment of the amino acid sequences set forth in SEQ ID NOs:4, 6, 10, 14, 20, and 22, and the *Arabidopsis thaliana* sequence (NCBI GI No. 1352316; SEQ ID NO:41). The data in Table 4 represents a calculation of the percent identity of the amino acid sequences set forth in SEQ ID NOs:4, 6, 10, 14, 20, and 22, and the *Arabidopsis thaliana* sequence (NCBI GI No. 1352316; SEQ ID NO:41).

TABLE 4

Percent Identity of Amino Acid Sequences Deduced From the Nucleotide Sequences of cDNA Clones Encoding Polypeptides Homologous to Dr1 Protein

| SEQ ID NO. | Percent Identity to NCBI GI No. 1352316; SEQ ID NO: 41 |
|---|---|
| 4 | 68.6 |
| 6 | 68.6 |
| 10 | 69.8 |
| 14 | 79.2 |
| 20 | 69.8 |
| 22 | 69.8 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a Dr1 protein. These sequences represent the first corn, rice, soybean, and wheat sequences encoding Dr1 proteins known to Applicant.

Example 4

Characterization of cDNA Clones Encoding DRAP1 Proteins

The insert in clones cs1.pk0049.al, cbn2.pk0039.h8, rls 12.pk0015.e 12, wl1.pk0012.f3, and w1m1.pk0016.f3 had been previously determined to encode DRAP1 protein (WO 99/09175). The sequence of the entire cDNA insert in clones cbn2.pk0039.h8, rls12.pk0015.e12, and w1m1.pk0016.f3 was determined. Further sequencing and searching of the DuPont proprietary database allowed the identification of a soybean clone encoding DRAP1 protein. The BLASTX search using the EST sequences from clones listed in Table 5 revealed similarity of the polypeptides encoded by the cDNAs to DRAP1 protein from *Homo sapiens* (NCBI GI Nos. 7513394 and 1491710). Shown in Table 5 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences encoding the entire protein derived from an FIS, a contig, or an FIS and PCR ("CGS"):

TABLE 5

BLAST Results for Sequences Encoding Polypeptides
Homologous to DRAP1 Protein

| Clone | Status | BLAST pLog Score NCBI GI No. 7513394 |
|---|---|---|
| cbn2.pk0039.h8 (FIS) | CGS | 23.70 |
| rls12.pk0015.e12 (FIS) | CGS | 23.70 |
| sdp4c.pk031.p18 (FIS) | CGS | 24.20 |
| wlm1.pk0016.f3 | FIS | 23.70 |

Sequence analysis indicated that the cDNA insert in rice clone rls12.pk0015.e12 encodes a full-length rice DRAP1 protein. The coding region in the cDNA insert is 777 bp in length and encodes a polypeptide of 258 amino acids (SEQ ID NO:32) with a calculated molecular weight of 28 kDa. In the N-terminal part of the rice DRAP1 protein encoded by rice clone rls2.pk0015.e12, there is a histone fold-like structure located from residue 9 to 84 (Baxevanis and Landsman (1998) Nucl Acids Res 26:372-375), which has significant homology with the histone fold domain of the human DRAP1 protein (Inostroza et al. (1992) Cell 70:477-489; Goppelt et al. (1996) EMBO J 15:3105-3116; Mermelstein et al. (1996) Genes Dev 10:1033-1048), and the yeast Dr1 protein (Kim et al. (1997) Proc Natl Acad Sci USA 94:820-825). Compared with human DRAP1, there are three extra amino acid stretches in rice DRAP1 described herein. The first one is residues 94 through 113, which contains a nuclear localization signal. The second one is residues 124 through 143, which includes arginine (R) and glycine (G) repeats (RG repeat). Some transcription factors have the RG repeat domain, whose function has not been elucidated yet. The third one is residues 213 through 226, 5 of which are acidic amino acids. In the rice DRAP1 described herein (SEQ ID NO:32), there are two acidic amino acid-rich domains (residues 155 through 189 and residues 249 through 258 and one proline-rich domain (residues 192 through 238). The acidic amino acid-rich domains and proline-rich domain are often involved in activation or repression of transcription factors. FIGS. 2A-2B present an alignment of the amino acid sequences set forth in SEQ ID NOs:28, 32, 34 and 40, and the *Homo sapiens* sequences (NCBI GI No. 7513394; SEQ ID NO:42). The data in Table 6 represents a calculation of the present identity of the amino acid sequences set forth in SEQ ID NOs:28, 32, 34 and 40, and the Homo sapiens sequence (NCBI GI No. 7513394; SEO ID NO:42).

TABLE 6

Percent Identity of Amino Acid Sequences Deduced
From the Nucleotide Sequences of cDNA Clones
Encoding Polypeptides Homologous to DRAP1 Protein

| SEQ ID NO. | Percent Identity to NCBI GI No. 7513394; SEQ ID NO: 42 |
|---|---|
| 28 | 31.2 |
| 32 | 33.2 |
| 34 | 34.1 |
| 40 | 33.2 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a DRAP1 protein. These sequences represent the first corn, rice, soybean, and wheat sequences encoding DRAP1 protein known to Applicant.

Example 5

Genomic Organization of Genes Encoding Dr1 and DRAP1 Proteins in Rice

The number of Dr1 and DRAP1 genes in rice genome, was determined by Southern blot analysis. Rice genomic DNA was digested with BamH I, EcoR I, EcoRV and Hind III restriction enzymes, separated by electrophoresis on an 1% agarose gel and blotted onto Hybond N+ membrane (Amersham Co., Piscataway, N.J.) using alkaline (0.4 N NaOH) blotting procedure. Kilobase markers were used as molecular weight standards (GiBCO-BRL, Rockville, Md.). Rice genomic DNA blots were separately hybridized with a full length cDNA corresponding to the insert in clone r10n.pk0076.g1 that encodes an entire rice Dr1 protein (SEQ ID NO: 10) and a full-length cDNA corresponding to the insert in clone rls12.pk0015.e12 that encodes an entire rice DRAP1 protein (SEQ ID NO:32). cDNAs were labeled with $^{32}$P-dCTP using RadPrime DNA Labeling system (GIBCO-BRL). Hybridization was carried out in church buffer at 55° C. for 24 hr. The blot was washed in 2×SSC for 5 min at room temperature twice, and then washed in 1×SSC, 0.5% SDS at 55° C. for 25 min twice.

As shown in FIG. 3A, the full-length rice Dr1 cDNA probe hybridized to two BamH I restriction fragments, two Hind III restriction fragments, three 3 EcoR I restriction fragments and three EcoRV restriction fragments, suggesting that there are two to three genes encoding Dr1 in the rice genome. The full-length rice DRAP1 cDNA probe hybridized to one restriction fragment from each of the BamH I, EcoR I, EcoRV and Hind III digested genomic DNAs (FIG. 3B) which suggests that there is only one gene encoding DRAP1 in the rice genome.

Example 6

Molecular Characterization of Rice Dr1 and DRAP1 Interaction

A Gal4 protein-based yeast two-hybrid system (Stratagene, San Diego, Calif.; Chien et al., (1991) Proc. Natl. Acad. Sci. USA 88: 9578-9582) was used to characterize the interaction between rice Dr1 and DRAP1 proteins in vivo. It has been shown that Dr1 requires DRAP1 as a co-factor to efficiently execute repression activity (Goppelt et al., (1996) EMBO J. 15: 3105-3116; Mermelstein et al., (1996) Genes & Dev. 10:1033-1048; Prelish (1997) Mol. Cell. Biol. 17: 2057-2065; Kim et al., (2000) Mol. Cell. Biol 20:2455-2465). The Gal4 protein-based two-hybrid system uses constructs pBD-Gal4 and pAD-Gal4 which encode the DNA binding domain and the activation domain respectively of the Gal4 protein (Stratagene, San Diego, Calif.; Chien et al., (1991) Proc. Natl. Acad. Sci. USA 88: 9578-9582). The rice Dr1 and DRAP1 cDNAs described in Example 5 were fused with pAD-Gal4 and pBD-Gal4 to generate pADGal4::rDr1 and pBDGal4::rDRAP1 constructs respectively. The EcoR I and Sma I fragment containing coding region of rice Dr1 was cloned into pAD-Gal4 EcoR I and Sma I sites to generate pADGal4::rDr1. The Mfe I and Pst I fragment containing coding region of rice DRAP1 was cloned into pBD-Gal4 EcoR I and Pst I sites to generate pBDGal4::rDRAP1. The pADGal4::rDr1 and pBDGal4::rDRAP1 were transformed independently and co-transformed into Stratagene's YRG-2 yeast strain (Stratagene, San Diego, Calif.). Competent YRG-2 cells were prepared according to the method of Eible (1992) *Biotechniques* 13:18-20) and transformed with one microgram of DNA added to a 50 ml aliquot of competent yeast cells. A mixture containing 240 µl 50% PEG (MW 3350), 36 µl 1M lithium acetate, and 50 µg of salmon sperm DNA was added to the yeast-DNA mixture. After mixing the mixture was incubated at 30° C. for 30 minutes and heat shocked at 42° C. for 20 minutes. Maximum of 200 µl of transformation mixture was plated on selective plates. For initial plating transformants containing the pADGal4::rDr1 construct (trp+), were plated on selection medium lacking tryptophan. Transformants containing the pBDGal4::rDRAP1 construct (leu+) were plated on selection medium lacking leucine and transformants harboring both pADGal4::rDr1 and pBDGal4::rDRAP1 were plated on medium lacking tryptophan, leucine and histidine. The interaction between fusion proteins ADGal4/rDr1 and BDGal4/rDRAP1 promotes expression, via the Gal4 promoter, of the plasmid based histidine synthase gene. FIG. 4 shows that yeast co-transformed with pADGal4::rDr1 and pBDGal4::rDRAP1 could grow in selection media without Trp, Leu and His, whereas yeast transformants containing pADGal4::rDr1 or pBDGal4::rDRAP1 alone could not grow on selection media lacking Trp, Leu and His (FIG. 4A). These results demonstrate that there is a physical interaction between Dr1 and DRAP1, which functions as a bridge to allow the ADGal4/rDr1 activation domain to activate the expression of histidine synthase gene, once the BDGal4/rDRAP1 fusion protein binds to the Gal4 promoter binding site.

The yeast two-hybrid system was also used to precisely map the amino acid domain of rice DRAP1 that physically interacts with the rice Dr1 protein. Three constructs encoding truncated rice DRAP1 proteins were made. For this purpose, an Mfe I site was introduced separately by site-directed mutagenesis after the codons for residues 12 and 63 in the rice DRAP1 cDNA disclosed herein, resulting in two different constructs with one having an Mfe I site after the codon for residue 12, and the other an Mfe I site after the codon for residue 63. These constructs were then digested with Mfe I and Pst I, and Mfe I/Pst I fragments encoding truncated versions of the rice DRAP1 protein lacking the N-terminal 12 and 63 amino acids were inserted into pBD-Gal4 to generate pBDGal4::rDRAP1NR13 and pBDGal4::rDRAP1NN64, respectively. Separately, a Msc I site was also introduced after the codon for residue 93 in the rice DRAP1 cDNA, enabling the isolation of an Mfe I/Msc I fragment encoding the rice DRAP1 N-terminal 93 amino acids which was then inserted into the EcoR I/Sma I sites of pBD-Gal4 to generate pBDGal4::rDRAP1G93. The interactions of pBDGal4::rDRAP1 G93, pBDGal4::rDRAP1 NR13, and pBDGal4::rDRAP1 NN64 with pADGal4::rDr1 were analyzed separately using the yeast two-hybrid system as described above. Construct pBDGal4::rDRAP1G93 encodes a truncated rice DRAP1 protein having only the N-terminal 93 amino acids. Constructs pBDGal4::rDRAP1NN64 and pBDGal4::rDRAP1NN13 encode truncated rice DRAP1 proteins with N-terminal deletions of 63 amino acids and 12 amino acids respectively (FIG. 4C). Each of the constructs (pBDGal4::rDRAP1 G93, pBDGal4::rDRAP1NN13 and pBDGal4::rDRAP1NN64) were individually cotransferred along with pADGal4::rDr1 into yeast (strain YRG-2). The transformants were then placed on selection medium lacking Trp, Leu and His for analysis as described above. The results indicated that the truncated rice DRAP1 proteins encoded by both pBDGal4::rDRAP1G93 and pBDGal4::rDRAP1NN13 could functionally interact with Gal4/rDr1 to support the grow of yeast on selection media without Trp, Leu and His. However, the truncated protein encoded by the pBDGal4::rDRAP1NN64 construct was unable to interact with Gal4/rDr1 which in turn inhibited the growth of transformants on the selection medium (FIG. 4C). The analysis demonstrates that the N-terminal region of rice DRAP1 from amino acid 13 to amino acid 93 is necessary for efficient interaction of rice DRAP1 with rice Dr1. The N-terminal 93 amino acids of the rice DRAP1 protein contains a histone fold-like structure that appears to be required for functional interaction with rice Dr1.

To further elucidate the function of rice DRAP1 and Dr1 proteins, tobacco protoplast transfection assays were utilized in which 35S4Gal4::GUS was used as a reporter plasmid, 35S::Luc was used as an internal control, and plasmid constructs 35S::rDr1, 35S::rDRAP1, 35S::Gal4/rDr1, 35S::Gal4/rDRAP1, 35S::Gal4/rDr1N150, and 35S::Gal4/rDr1C150 were tested as effectors (Liu et al., (1994) *Plant Cell* 6:645-657), analyzing how these different plasmid constructs affected expression of the reporter plasmid. *Nicotiana tabacum* NT-1 cells were grown in suspension culture to mid-log phase as described by Allen et al., (1996) *Plant Cell* 5:603-613, and protoplasts were isolated using a modification of the procedure of Liu et al. (1994) *Plant Cell* 6:645-657. Cells were harvested by centrifugation at 300×g for 10 minutes and resuspened in 50 ml of enzyme solution (Sigma Protoplast Isolation Enzyme Solution I) and incubated at room temperature with gentle shaking for 4-6 hours. The resulting protoplasts were harvested by centrifugation at 133×g for 5 minutes and resuspended in W5 media (154 mM NaCl, 5 mM HCl, 125 ml $CaCl_2$, 5 mM glucose, pH 6.0) at a density of $2 \times 10^6$ cells/ml. Prior to transformation, cells were resuspended at the same density in MC media (5 mM MES, 20 mM $CaCl_2$, 0.5 M mannitol, pH 5.7).

NT-1 protoplasts were transfected and analyzed using a modified version of Liu et al. (1994) *Plant Cell* 6:645-657. A transformation mix consisting of 300 µl of protoplasts, 1-5 µg of plasmid DNA and 300 µl PEG solution (0.1 M $Ca(NO3)_2$, 0.4 M mannitol, 40% PEG 3350, pH 10) was prepared then transferred to 4 ml of MS media (4.3 g/l MS salts, 40 g/l sucrose, 4 mg/l glycine, 1 mg/l thiamine, 1 mg/l pyridoxine, 1 mg/l nicotinic acid, 2 mg/l NAA (α-naphthalenacetic acid), 0.4 mg/l kinetin, pH 5.8), gently mixed, and incubated for 2 days.

Transfected protoplasts were harvested by centrifugation at 133×g for 15 minutes and the PEG solution removed by aspiration. Cells were resuspended in 200 µl of lysis buffer (Promega Luciferase Cell Culture Lysis Reagent), mixed by vortexing, and centrifuged at 14,000×g for 2 minutes at 4° C. The supernatant extract was used for LUC and GUS assays.

Luciferase assays were performed by mixing 2 µl of extract with 100 µl of LUC substrate (Promega Luciferase Assay Reagent) and measuring the emitted photons for 0.5 seconds in a luminometer.

Fluorometric GUS assays were performed as described (Jefferson, (1987) *Mol. Biol. Rep.* 5:387-405). For each assay, 82.5 µl of extract was added to 495 µl of GUS substrate (1.7 mM 4-MUG in lysis buffer) and incubated at 37° C. Aliquots of 175 µl were taken at 0, 1, and 2 hours and mixed with 75 µl of stop buffer (0.6 M Na2CO3). A fluorescence multi-well plate reader was used to measure the GUS activity at 1ex 365 m and 1em 455 nm.

The enhancer fragment (−832 to −50) of 35S promoter from p35SGal4VP16 (U.S. Pat. No. 5,968,793) was first amplified by PCR using oligonucleotides p278 (SEQ ID NO:51) and p280 (SEQ ID NO:52) as primers. The PCR product was then digested with Spe I/BamH I and inserted into the Spe I/BamH I sites of pG4G vector (U.S. Pat. No. 5,968,793) to generate p35S4Gal4::GUS reporter construct, in which the GUS gene is driven by the strong CaMV 35S promoter with four Gal4 binding sites.

```
p278:
5'-CGGGATCCGATAGTGGGATTGTGCGTC-3'    (SEQ ID NO: 51)

p280:
5'-ACTGGCTCACGCTAGGAACC-3'           (SEQ ID NO: 52)
```

Construct p35S::Gal4/rDr1 was made by replacing the EcoRI/MscI fragment of p35SGal4VP16 (U.S. Pat. No. 5,968,793) with the EcoR1/SmaI fragment of rice Dr1 cDNA from pGEM-rDr1. Construct p35S::Gal4/rDr1 contains the coding region for a Gal4 DNA-binding domain-rice Dr1 hybrid protein (Gal4/rDr1) driven by the CaMV 35S promoter.

p35S::Gal4/rDr1 was digested with NcoI and EcoRI, filled in with Klenow fragment, and then self-ligated to generate p35S::rDr1, which contains the coding region for a rice Dr1 protein (rDr1) driven by the CaMV 35S promoter.

Construct p35S::rDRAP1 contains the coding region for a rice DRAP1 protein (rDRAP1) driven by the CaMV 35S promoter. To generate the construct 35S::rDRAP1, the 774 bp NcoI/XhoI fragment of rice DRAP1 cDNA from pET29-rDRAP1 was used to replace the NcoI/Pm1I fragment of p35SGal4VP16 (U.S. Pat. No. 5,968,793). NcoI and XhoI sites were introduced into rice DRAP1 cDNA around its translation initiation and stop codons respectively by in vitro mutagenesis using oligos Q19 (SEQ ID NO:53) and Q20 (SEQ ID NO:54), respectively, as primers. The 774 bp NcoI/XhoI fragment of rice DRAP1 was inserted into pET-29b (Novagen) to generate pET29-rDRAP1.

```
Q19:
5'-GCCCAGCTTCTTCCCCATGGCTTCGTCTTCC  (SEQ ID NO: 53)
TGC-3'

Q20:
5'-GATGGCCGTGGCTACTCGAGATCCTCGTTGT  (SEQ ID NO: 54)
CGTAG-3'
```

Construct p35S::Gal4/rDRAP1 contains the coding region for a Gal4 DNA-binding domain-rice DRAP1 hybrid protein (Gal4/rDRAP1) driven by the CaMV 35S promoter. To construct p35S::Gal4/rDRAP1, the coding region of rice DRAP1 cDNA was amplified with primers p300 (SEQ ID NO:55) and p301 (SEQ ID NO:56). The PCR product was digested with EcoRI/MscI and used to replace the EcoRI/MscI fragment of p35SGal4VP16 (U.S. Pat. No. 5,968,793).

```
p300:
5'-GGCAATTGAGGAAGAAGCTGGGCA-3'      (SEQ ID NO: 55)

p301:
5'-CCATCACAGCTAGCTGCAGC-3'          (SEQ ID NO: 56)
``` p35S::Gal4/rDr1C150 encodes a protein wherein the Gal4 DNA binding domain is fused with the rice Dr1 C-terminal part from residue 151 to 296 (Gal4/rDr1C150). A MscI site was introduced by site-directed mutagenesis using Q175 (SEQ ID NO:57) as primer into p35S::Gal4/Dr1 at the codon encoding residue 150 of rice Dr1 to generate p35S::Gal4/Dr1-M, which was then cut with EcoRV and MscI, and then self-ligated to generate p35S::Gal4/Dr1C150.

```
Q175:   5'-CCAGAACCTGAAGCGTGGCCACAGCAA-
CAAACACAACA-3' (SEQ ID NO:57)
```

35S::Gal4/rDr1N150 encodes a protein wherein the Gal4 DNA binding domain is fused with the rice Dr1 N-terminal part from residue 1 to 150 (Gal4/rDr1N150). To generate 35S::Gal4/rDr1N150, the NcoI/MscI fragment of p35S::Gal4/rDr1-M was used to replace the NcoI/MscI fragment of p35S::Gal4/rDRAP1.

The coding region of luciferase gene in pMAMneo-luc (ClonTech) was amplified by PCR using oligos LUC5' (SEQ ID NO:58) and LUC3' (SEQ ID NO:59) as primers to produce a 1.8 kb fragment with 5' NcoI and 3' KpnI sites, which was used to replace the NcoI/KpnI fragment of pMH40 (PCT Publication No. WO 98/16650) to generate p35S::Luc construct. p35S::Luc construct contains the luciferase coding region driven by the CaMV35S promoter, and was used as an internal control to take into account variability in transfection efficiency.

```
LUC5':
5'-GGCCATGGAAGACGCCAAAAAC-3'        (SEQ ID NO: 58)

LUC3':
5'-GGGGCCCGGTACCCGGGGATCC-3'        (SEQ ID NO: 59)
```

The results of the analysis as shown in FIG. 5, indicated that Gal4/rDr1 functions as a weak repressor, which represses about 20% expression of p35S4Gal4::GUS, and Gal4/rDRAP1 functions as a strong repressor, which represses about 50% expression of p35S4Gal4::GUS. Combination of p35S::Gal4/rDRAP1 with p35S::rDr1 as effectors exhibit stronger repression than that of p35S::Gal4/rDRAP1 alone. A combination of p35S::Gal4/rDr1 with p35S::rDRAP1 as effectors also exhibit stronger repression than that of p35S::Gal4/rDr1 alone. Over-expression of rice Dr1 or rice DRAP1 protein lacking Gal4 fusion (using p35S::rDr1 or p35S::rDRAP1, respectively) in transfected tobacco protoplasts had no effect on the expression of the reporter gene (FIG. 5). These results demonstrate that the Gal4 binding domain provides site-specific selection for repression of the targeted gene and that rice Dr1 and rice DRAP1 functionally interact with each other to form stronger repressor complex in vivo. It is interesting to note that Gal4/rDRAP1 functions as a stronger repressor than the Gal4/rDr1, which has not been detected before.

It was also found that Gal4/Dr1C150, which contains the Gal4 DNA binding domain fused with the rice Dr1 C-terminal part from residue 151 to 296, has no repression activity on GUS expression from p35S4Gal4::GUS (FIG. 5B). This result suggests that the proline and glutamine rich domain of the rice Dr1 can not function as repression domain by itself, at least in this protoplast transient expression system.

As disclosed above the histone-fold domain of rice DRAP1 is necessary for interaction with rice Dr1 in yeast. To determine whether the histone-fold domain is necessary for its repression activity, a series of N- and C-terminal deletion mutants were made and tested for repression activity in transfected tobacco protoplasts.

Using p35S::Gal4/rDRAP1 as template and oligonucleotide Q159 (SEQ ID NO:60) as primer, a MfeI site was introduced by site directed mutagenesis into p35S::Gal4/rDRAP1 to generate p35S::Gal4/rDRAP1-MM1 construct.

Q159: 5'-GCAAAGACATTGAATCAATTGTCCTTC-CACCTAAAGCA-3' (SEQ ID NO:60)

p35S::Gal4/rDRAP1-MM1 was digested with MfeI and then self ligated to produce 35S::Gal4/rDRAP1NN64 which encodes a Gal4 DNA-binding domain/rDRAP1 fusion protein in which the rice DRAP1 protein part is truncated, lacking the N-terminal 63 amino acids of rice DRAP1 as set forth in SEQ ID NO:32.

Using p35S::Gal4/rDRAP1 as template and oligonucleotides Q156 (SEQ ID NO:61), Q157 (SEQ ID NO:62) and Q172 (SEQ ID NO:63) as primers, an EcoRV site was introduced by site-directed mutagenesis into p35S::Gal4/rDRAP1 to produce p35S::Gal4/rDRAP1-EV3, p35S::Gal4/rDRAP1-EV4, and p35S::Gal4/rDRAP1-EV6, respectively.

```
Q156:
5'-AGAGGGCGAGGACGAGATATCCCACCCACCA (SEQ ID NO: 61)
AGCGGA-3'

Q157:
5'-GAATCTCGATCAAGCGATATCAAAATGGCCG (SEQ ID NO: 62)
TAAGAA-3'

Q172:
5'-TGTGTGAGGAGGTACGATATCAGTTCTTTTG (SEQ ID NO: 63)
ACTTC-3'
```

Plasmids p35S::Gal4/rDRAP1-EV3, p35S::Gal4/rDRAP1-EV4, and p35S::Gal4/rDRAP1-EV6 were digested with EcoRV/MscI, and then self ligated to produce p355::Gal4/rDRAP1 R148, p355::Gal4/rDRAP1 S123, and p35S::Gal4/rDRAP1Y75, respectively. p35S::Gal4/rDRAP1R148, p35S::Gal4/rDRAP1 S123, and p35S::Gal4/rDRAP1 Y75 encode Gal4 DNA-binding domain/rDRAP1 fusion proteins in which the rice DRAP1 protein part is truncated, lacking the C-terminal 111 amino acids, 136 amino acids, and 184 amino acids, respectively, of rice DRAP1 as set forth in SEQ ID NO:32.

The results (FIG. 6B) showed that deletion of the N-terminal 63 amino acids of rice DRAP1 eliminated DRAP1 repression activity. Deletion of DRAP1 C-terminal 111 amino acids gave stronger repression activity than that of the full length protein. Deletion of DRAP1 C-terminal 136 amino acids still had full repression activity, but deletion of C-terminal 184 1-66 amino acids eliminated its repression activity (FIG. 6B). These results demonstrate that the N-terminal 122 423 amino acids are sufficient for rice DRAP1 repression activity, the 48 amino acids between 74 and 123 are necessary for the repression activity, and the amino acids between 122 and 148 are also involved in mediating strong repression activity of DRAP1.

Example 7

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810-812) and the 3' region of the nopaline synthase gene from the T-DNA of the Ti plasmid of Agrobacterium tumefaciens.

The particle bombardment method (Klein et al. (1987) Nature 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 8

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al.(1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-α-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Other expression plasmids may be used for expression in *E. coli*. For example, the EcoRI and Bam HI fragment of pGEM-rDr1 was inserted into the EcoRI/BamHI sites of pET33b (Novagen) to generate pET33b-rDr1 construct. NcoI and XhoI sites were introduced into rice DrAp1 cDNAs around its translation initiation and stop codons respectively by in vitro mutagenesis as described in Example 6. The 774 bp NcoI/XhoI fragment of rice DRAP1 was inserted into the NcoI/XhoI sites of pET-29b (Novagen) to generate pET29-rDRAP1. pET33b-rDr1 and pET29-rDrAp1 were transformed into *E. coli* BL21 (DE3) cells. Transformed BL21 (DE3) cells were grown at 30° C. to an $OD_{600}$ of 1.0, induced by 0.2 mM isopropyl-β-D-thiogalactopyranosite (IPTG) for 3 h and then harvested. The recombinant proteins were purified with His-tag agarose beads (Qiagen) and further purified with T-7 tag agarose beads (Novagen) for rice Dr1 or S-tag agarose beads (Novagen) for rice DRAP1. The purified recombinant proteins were denatured with 2 M urea, and dialyzed in renature buffer (20 mM Hepes-KOH, 1 mM $MgCl_2$, 50 mM KCl, 1 mM DTT, 20% glycerol and 0.02% NP40) overnight, and then concentrated with centriprep10 (Amicon). Concentrated rice Dr1 and rice DRAP1 were frozen in liquid $N_2$ and stored at −70° C.

Example 10

Evaluating Compounds for Their Ability to Inhibit the Activity of Proteins Involved in Regulation of Gene Expression The polypeptides described herein may be produced using any number of methods known to those skilled in the art. Such methods include, but are not limited to, expression in bacteria as described in Example 9, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. Functional assays for Dr1 and DRAP1 proteins are taught herein.

Example 11

Rice Dr1 and rice DRAP1 Cellular Localization and Interaction with TBP-DNA Complex To study the localization of rDr1 and rDrAp1 in plant cells, the coding regions of rDr1 and rDrAp1 were inserted into vector pRTL2-mGFP (von Arnim et al. (1998) *Gene* 221:35-43) to generate p35S::rDr1/mGFP and p35S::rDRAP1/mGFP constructs (FIG. 5A), which contain rDr1/mGFP and rDrAp1/mGFP fusion genes, respectively. The localization of these fusion proteins and the control mGFP in live transfected protoplasts were monitored by confocal microscopy (Gindullis et al. (1999) *Plant Cell* 11:1755-1767). The constructs were transfected into tobacco protoplasts as described in Example 6.

To make p35S::rDr1/mGFP, the EcoRI/NcoI fragment of pRTL2-mGFP (von Arnim et al. (1998) *Gene* 221:35-43) was replaced with the EcoRI/NcoI fragment of pGEM-rDr1. Plasmid p35S::rDr1/mGFP encodes rDr1/mGFP, a rice Dr1/mGFP (green fluorescent protein) fusion protein.

To make p35S::rDRAP1/mGFP, the coding region of rice DRAP1 was first amplified with Q222 (Mfe I site-containing rice DRAP1 gene-specific oligonucleotide) (SEQ ID NO:64) and Q223 (Nco I site-containing rice DRAP1 gene-specific oligonucleotide) (SEQ ID NO:65) as primers.

```
Q222:
5'-AACAATTGGAGGAGCGGAGGCGGA-3'    (SEQ ID NO: 64)

Q223:
5'-AACCATGGAATCCTCGTTGTCGTAGTC-3' (SEQ ID NO: 65)
```

The PCR product was inserted into pre-cut blunt-end vector pPCR-Script Amp (Stratagene, Calif.) to generate pST-rDRAp1, which was completely digested with MfeI and partially digested with Nco I. The resulting 822 bp Mfe VI/Nco I fragment of rice DRAP1 cDNA was used to replace the Eco RI/Nco I fragment of pRTL-mGFP (von Arnim et al. (1998) *Gene* 221:35-43) to generate p35S::rDRAP1I/mGFP which encodes rDRAP1/mGFP, a rice DRAP1/mGFP fusion protein.

Both the p35::rDr1/mGFP and p35S::rDRAP1/mGFP constructs were confirmed by DNA sequencing.

FIG. 7B shows that the mGFP itself was found to be present both in the cytoplasm and in the nucleus. Although mGFP does not have a nuclear localization signal peptide, it can passively diffuse into the nucleus due to its small size (27 kDa) (Gorlich and Mattaj (1996) *Science* 271:1513-1518; Grebenok et al. (1997) *Plant J* 12:685-696). However, both rDr1/mGFP and rDRAP1/mGFP were observed to be nearly exclusively localized in the nuclei, except the nucleolus, of transfected protoplasts. These data suggest that rice Dr1 and rice DRAP1 are nuclear proteins, both of which can drag the mGFP into nuclei when fused with mGFP.

The gel shift assay was then used to study whether or not rice Dr1 and rice DRAP1 interact with DNA. Using the DNA fragment of the rice PAL gene from −61 to +79 region (transcription start site as +1) as a probe (Zhu et al. (1995) *Plant Mol Biol* 29:535-550), and purified recombinant rDr1 and rDrAp1 (obtained from *E. coli* as described in Example 9), rice Dr1 was found to have no DNA affinity. There was no detectable shifted band when 250 ng of purified rice Dr1 was used in the reactions (FIG. 8A, lane 2). Purified recombinant rice DRAP1 interacted with the DNA to form three shifted bands, A, B and C (FIG. 8A, lane 3). 100 ng rice DRAP1 was enough to detect the DNA-protein interaction in the assays. Addition of rice Dr1 and rice DRAP1 together produced stronger signals for the three shifted bands and also produced a further shifted band D (FIG. 8A, lane 4). These data demonstrate that rice DRAP1 itself interacts with DNA, and that rice Dr1 can enhance rice DRAP1 binding to DNA and to form a higher order complex.

The interactions of rice Dr1 and rice DRAP1 with the rice TBP-DNA complex were then studied. As shown in Example 12, rice TBP (TATA-binding protein) has weak affinity with the TATA element of rice PAL promoter, which is in agreement with other studies (Iwataki et al. (1997) *Plant Mol Biol* 34:69-79). Because of the instability of rice TBP-DNA complex, it produces several bands in gel shift assays (FIG. 8B, lane 1). Upon addition of rDr1 into the reaction of rice TBP (rTBP) and DNA, all the shifted bands in lane 1 by rTBP were supershifted. More importantly, it also produced a further shifted band E (FIG. 8B, lane 2). Addition of rDRAP1 to the reaction of rTBP and DNA also supershifted all bands (A, B, C) in lane 1 into F area (FIG. 8B, lane 3). Addition of rDr1 and rDRAP1 together produced not only supershift band at G area from F area, the D band into H band, but also much stronger signal of E band (FIG. 8B, lane 4). These data show that while both rDr1 and rDRAP1 alone can interact with the rTBP-DNA complex, together they can interact strongly with the TBP-DNA complex to form larger complexes.

Example 12

RiceDr1 and Rice DRAP1 Repression of the Rice TBP Enhanced Transcription From the Rice PAL Promoter In Vitro In other eukaryotic systems, the Dr1/DRAP1 complex has been considered as a general repressor of class II promoters. To study the function of rDr1 and rDRAP1, the plant in vitro transcription analysis using rice PAL promoter/Gus gene fusion as a transcription reporter and rice whole cell extract for the transcription machinery (Zhu et al.(1995) *Plant J* 5:1021-1030) was used. Recombinant rDr1 and rDRAP1 were purified to near homogenity as described in Example 9.

To isolate recombinant rice TATA-binding protein, a cDNA encoding an entire rice TATA-binding protein (rTBP) was first cloned by screening a rice 1 ZPII leaf cDNA library (S. R. McCouch, Cornell University). The pBluescript plasmid (Stratagene) containing the rice TBP cDNA was recovered. Nucleotide sequences were determined by the dideoxy chain termination method (Sanger et al. (1977) *Proc. Natl. Acad. Sci. USA* 74:5463-5467). The sequence of the cDNA is set forth in SEQ ID NO:66 and the encoded protein sequence is set forth in SEQ ID NO:67. With these sequences, and the likelihood that rTBP is expressed in all tissues because it is involved in the transcription machinery, it is envisioned that cloning cDNAs encoding rTBP will become routine since methods for cDNA library construction, library screening using probes based on SEQ ID NOs:66 and 67, DNA sequencing, and DNA cloning are well-known in the art.

NcoI and XhoI sites were introduced into the rice TBP cDNA in the pBluescript plasmid (Stratagene) that was recovered as described above around its translation initiation and stop codons respectively by in vitro mutagenesis (Zhu et al. (1995) Plant Cell 7:1681-1689) using as primers oligonucleotides QZ-1 (SEQ ID NO:68) and QZ-2 (SEQ ID NO:69), respectively.

```
QZ-1:
5'-GCCATCGTCGGATCCATGGCGGCGGAGGC      (SEQ ID NO: 68)
G-3'

QZ-2:
5'-CCATAAGTTTTCACTCGAGCTGCTGGACT      (SEQ ID NO: 69)
TT-3'
```

The NcoI/XhoI fragment of rice TBP was inserted into the NcoI/XhoI sites of pET-29a (Novagen) to generate pET-rTBP, which was transformed into E. coli BL21 (DE3) cells (Stratagene). Cells were grown at 30° C. to an $OD_{600}$ of 1.0, induced by 0.2 mM isopropyl-b-D-thiogalactopyranosite (IPTG) for 3 h. Cells were harvested and the recombinant proteins were purified with His-Trap™ (Pharmacia Biotech) and further purified with S-tag agarose beads (Novagen). The S-tag was excised from purified rTBP protein by thrombin treatment. The recombinant protein was denatured with 2 M urea, and dialyzed in renature buffer (20 mM Hepes-KOH, 1 mM $MgCl_2$, 50 mM KCl, 1 mM DTT, 20% glycerol and 0.02% NP40) overnight, and then concentrated with centriprep10 (Amicon). Concentrated rTBP and rTFIIB was frozen in liquid $N_2$ and stored at −70° C. The deduced molecular weight of rTBP recombinant protein is about 23.2 kDa as indicated in a Coomassie Brilliant Blue stained gel.

FIG. 9 shows that rTBP enhanced basal transcription in rice whole cell extracts. Addition of purified recombinant rDRAP1 repressed the transcription of PAL/GUS reporter gene in a dose dependent manner. rDRAP1 (200 ng) repressed transcription of the reporter gene by about 40% (FIG. 9, lane 4). Purified rDr1 exhibited weak repression activity when added into the rice whole cell extract. rDr1 (500 ng) repressed reporter gene transcription by about 20%. However, a combination of 250 ng rDr1 with 200 ng rDRAP1 repressed the transcription activity of the reporter gene by about 74%, which eliminated almost all the enhanced effects of rTBP (FIG. 9, lanes 1, 2 and 7). These results demonstrate that rDRAP1 alone can function as repressor, rDr1 alone has weak repression activity, and combination of rDr1 and rDRAP1 functions as a very strong repressor.

What is claimed is:

1. An isolated polynucleotide comprising:
   (a) a nucleotide sequence encoding a polypeptide having transcriptional repressor activity, wherein the polypeptide has an amino acid sequence of at least 85% sequence identity when compared to SEQ ID NO:32, based on the Clustal method of alignment with pairwise alignment default parameters of KTUPLE=1, GAP PENALTY=3, WINDOW=5 and DIAGONALS SAVED=5; or
   (b) a complement of the nucleotide sequence of (a), wherein the complement and the nucleotide sequence consist of the same number of nucleotides and are 100% complementary.

2. The polynucleotide of claim 1, wherein the amino acid sequence of the polypeptide has at least 90% sequence identity when compared to SEQ ID NO:32, based on the Clustal method of alignment with the pairwise alignment default parameters.

3. The polynucleotide of claim 1, wherein the amino acid sequence of the polypeptide has at least 95% sequence identity when compared to SEQ ID NO:32, based on the Clustal method of alignment with the pairwise alignment default parameters.

4. The polynucleotide of claim 1, wherein the amino acid sequence of the polypeptide comprises SEQ ID NO:32.

5. The polynucleotide of claim 1 wherein the nucleotide sequence comprises SEQ ID NO:31.

6. A vector comprising the polynucleotide of claim 1.

7. A recombinant DNA construct comprising the polynucleotide of claim 1 operably linked to at least one regulatory sequence.

8. A method of transforming a cell, comprising transforming a cell with the polynucleotide of claim 1.

9. A cell comprising the recombinant DNA construct of claim 7.

10. A method for producing a transgenic plant comprising transforming a plant cell with the polynucleotide of claim 1 and regenerating a transgenic plant from the transformed plant cell.

11. A plant comprising the recombinant DNA construct of claim 7.

12. A seed comprising the recombinant DNA construct of claim 7.

13. A method for isolating a encoded polypeptide having transcriptional repressor activity, comprising isolating the polypeptide from the cell of claim 9, wherein the recombinant DNA construct is expressed in the cell.

* * * * *

SEQUENCE LISTING

```
<160> NUMBER OF SEQ ID NOS: 69

<210> SEQ ID NO 1
<211> LENGTH: 400
<212> TYPE: DNA
<213> ORGANISM: Zea mays

<400> SEQUENCE: 1
ggcacgagct cgattcaact ctgcgcgaga cgaattctct cccgaattcg ctcgccgaaa        60
gcacctgcta cctcgcgccc gccttccgtc gcgcggattc ggtgccgtgc gtggagatgg       120
acccgatgga catcgtgggg aagtctaagg aggacgtttc cctccccaaa tcaacaatgg       180
ttaagataat taaggagatg cttcctcctg atgtacgagt ggcaagagat gcacaggatc       240
ttcttgttga atgctgcgta gagttcatca atctcctttc gtctgaatcc aatgaagtgt       300
gcagcagaga agagaagaaa acaattgctc ctgagcatgt tatcaaggct ctaagtgatc       360
ttggcttcag agagtacatt gaggaggttt atgctgcgta                            400

<210> SEQ ID NO 2
<211> LENGTH: 132
<212> TYPE: PRT
<213> ORGANISM: Zea mays

<400> SEQUENCE: 2

His Glu Leu Asp Ser Thr Leu Arg Glu Thr Asn Ser Leu Pro Asn Ser
  1               5                  10                  15

Leu Ala Glu Ser Thr Cys Tyr Leu Ala Pro Ala Phe Arg Arg Ala Asp
             20                  25                  30

Ser Val Pro Cys Val Glu Met Asp Pro Met Asp Ile Val Gly Lys Ser
```

```
                35                  40                  45
Lys Glu Asp Val Ser Leu Pro Lys Ser Thr Met Val Lys Ile Ile Lys
 50                  55                  60

Glu Met Leu Pro Pro Asp Val Arg Val Ala Arg Asp Ala Gln Asp Leu
 65                  70                  75                  80

Leu Val Glu Cys Cys Val Glu Phe Ile Asn Leu Leu Ser Ser Glu Ser
                 85                  90                  95

Asn Glu Val Cys Ser Arg Glu Glu Lys Lys Thr Ile Ala Pro Glu His
                100                 105                 110

Val Ile Lys Ala Leu Ser Asp Leu Gly Phe Arg Glu Tyr Ile Glu Glu
            115                 120                 125

Val Tyr Ala Ala
            130

<210> SEQ ID NO 3
<211> LENGTH: 1405
<212> TYPE: DNA
<213> ORGANISM: Zea mays

<400> SEQUENCE: 3
ccacgcgtcc gcaacccctc ccctcgtatt aggccccacc tccccgcgcg ccctaaccct      60
agcttctcga ttcaactctg cgcgagacga attctctccc gaattcgctc gccgaaagca     120
cctgctacct cgcgcccgcc ttccgtcgcg cggattcggt gccgtgcgtg gagatggacc     180
cgatggacat cgtggggaag tctaaggagg acgtttccct ccccaaatca acaatggtta     240
agataattaa ggagatgctt cctcctgatg tacgagtggc aagagatgca caggatcttc     300
ttgttgaatg ctgcgtagag ttcatcaatc tcctttcgtc tgaatccaat gaagtgtgca     360
gcagagaaga gaagaaaaca attgctcctg agcatgttat caaggctcta agtgatcttg     420
gcttcagaga gtacattgag gaggtttatg ctgcgtatga acagcacaaa ctcgagactc     480
tggattctcc aaaagctggc aagttcacta ggattgagat gacagaggaa gaagctgttg     540
ctgagcaaca aggatgtttt gctgaggctc gagcaaggat gaataacgga gcccccaagc     600
caaaggagcc agaacaagaa ccgccacagc taccacaagc acaacccaa cttcagctgc      660
atactgaacc acagcaaccc atgcaatctc aagttcagtt gcattcgcaa acacaacact     720
acctccaacc tcaactgcag ctccaccatc agccacaaca gctcccacaa gtgcagctgc     780
actctcagcc gcagctgcaa ccccaagtgc atctgcaccc tcagccgcag ttgcccccac     840
aattgcaggt ccatcagcag ctgcagcaac ccccacaagt gcaggtccac cagcagcccg     900
aagtgcagcc ccaagaagcg cagttgcaat catcagccca gcaaacctcc caaccgcaac     960
ctcaggcaca actacaatca caggggcact acaagcgcga gctgcaagcc ggactgctgg    1020
gtcagttgca gacacaggcg caaaccggac ctgacatgga tagttagaga ctattgtgta    1080
gcctgagtat aagcaaaaaa gggaaaaaaa accaggcact tttgctgcat ctactagaaa    1140
cctgtatgcc tgcttgtgac tcattagatc ctgatttagg tttccgtgct tcctgtagaa    1200
tgtaaatgca gtgtgattgc agttgccttg ttgctaataa tgcgaagccg ttagttactg    1260
atgatgtcat tattgtgtgg aatactgaat tcgtgacaag tgtcatggca tggttttatg    1320
tgacgtgctg aaagatattc cgttgccaaa aaaaaaaaa aaaaaaaaa aaaaaaaaa       1380
aaaaaaaaa aaaaaaaaa aaaaa                                            1405

<210> SEQ ID NO 4
<211> LENGTH: 334
```

```
<212> TYPE: PRT
<213> ORGANISM: Zea mays

<400> SEQUENCE: 4
```

| | | | | | | | | | | | | | | |
|---|---|---|---|---|---|---|---|---|---|---|---|---|---|---|
| Leu | Leu | Asp | Ser | Thr | Leu | Arg | Glu | Thr | Asn | Ser | Leu | Pro | Asn | Ser | Leu |
| 1 | | | | 5 | | | | | 10 | | | | | 15 | |
| Ala | Glu | Ser | Thr | Cys | Tyr | Leu | Ala | Pro | Ala | Phe | Arg | Arg | Ala | Asp | Ser |
| | | | 20 | | | | | 25 | | | | | 30 | | |
| Val | Pro | Cys | Val | Glu | Met | Asp | Pro | Met | Asp | Ile | Val | Gly | Lys | Ser | Lys |
| | | 35 | | | | | 40 | | | | | 45 | | | |
| Glu | Asp | Val | Ser | Leu | Pro | Lys | Ser | Thr | Met | Val | Lys | Ile | Ile | Lys | Glu |
| | 50 | | | | | 55 | | | | | 60 | | | | |
| Met | Leu | Pro | Pro | Asp | Val | Arg | Val | Ala | Arg | Asp | Ala | Gln | Asp | Leu | Leu |
| 65 | | | | | 70 | | | | | 75 | | | | | 80 |
| Val | Glu | Cys | Cys | Val | Glu | Phe | Ile | Asn | Leu | Leu | Ser | Ser | Glu | Ser | Asn |
| | | | | 85 | | | | | 90 | | | | | 95 | |
| Glu | Val | Cys | Ser | Arg | Glu | Lys | Lys | Thr | Ile | Ala | Pro | Glu | His | Val |
| | | | 100 | | | | | 105 | | | | | 110 | | |
| Ile | Lys | Ala | Leu | Ser | Asp | Leu | Gly | Phe | Arg | Glu | Tyr | Ile | Glu | Glu | Val |
| | | 115 | | | | | 120 | | | | | 125 | | | |
| Tyr | Ala | Ala | Tyr | Glu | Gln | His | Lys | Leu | Glu | Thr | Leu | Asp | Ser | Pro | Lys |
| | 130 | | | | | 135 | | | | | 140 | | | | |
| Ala | Gly | Lys | Phe | Thr | Arg | Ile | Glu | Met | Thr | Glu | Glu | Glu | Ala | Val | Ala |
| 145 | | | | | 150 | | | | | 155 | | | | | 160 |
| Glu | Gln | Gln | Arg | Met | Phe | Ala | Glu | Ala | Arg | Ala | Arg | Met | Asn | Asn | Gly |
| | | | | 165 | | | | | 170 | | | | | 175 | |
| Ala | Pro | Lys | Pro | Lys | Glu | Pro | Glu | Gln | Glu | Pro | Pro | Gln | Leu | Pro | Gln |
| | | | 180 | | | | | 185 | | | | | 190 | | |
| Ala | Gln | Pro | Gln | Leu | Gln | Leu | His | Thr | Glu | Pro | Gln | Gln | Pro | Met | Gln |
| | | 195 | | | | | 200 | | | | | 205 | | | |
| Ser | Gln | Val | Gln | Leu | His | Ser | Gln | Thr | Gln | His | Tyr | Leu | Gln | Pro | Gln |
| | 210 | | | | | 215 | | | | | 220 | | | | |
| Leu | Gln | Leu | His | His | Gln | Pro | Gln | Gln | Leu | Pro | Gln | Val | Gln | Leu | His |
| 225 | | | | | 230 | | | | | 235 | | | | | 240 |
| Ser | Gln | Pro | Gln | Leu | Gln | Pro | Gln | Val | His | Leu | His | Pro | Gln | Pro | Gln |
| | | | | 245 | | | | | 250 | | | | | 255 | |
| Leu | Pro | Pro | Gln | Leu | Gln | Val | His | Gln | Gln | Leu | Gln | Gln | Pro | Pro | Gln |
| | | | 260 | | | | | 265 | | | | | 270 | | |
| Val | Gln | Val | His | Gln | Pro | Glu | Val | Gln | Pro | Gln | Glu | Ala | Gln | Leu |
| | | 275 | | | | | 280 | | | | | 285 | | | |
| Gln | Ser | Ser | Ala | Gln | Gln | Thr | Ser | Gln | Pro | Gln | Pro | Gln | Ala | Gln | Leu |
| | 290 | | | | | 295 | | | | | 300 | | | | |
| Gln | Ser | Gln | Gly | His | Ser | Gln | Ala | Gln | Leu | Gln | Ala | Gly | Leu | Leu | Gly |
| 305 | | | | | 310 | | | | | 315 | | | | | 320 |
| Gln | Leu | Gln | Thr | Gln | Ala | Gln | Thr | Gly | Pro | Asp | Met | Asp | Ser |
| | | | | 325 | | | | | 330 | | | | | | |

```
<210> SEQ ID NO 5
<211> LENGTH: 1316
<212> TYPE: DNA
<213> ORGANISM: Zea mays

<400> SEQUENCE: 5
ccacgcgtcc gattccactc tgcccgagca agccgaattg tcgtccgaat tcgctcgcgg      60
ggagcacttg ctacctcgcg cccgccttct gtcgcgcgga ttcgttgctg cgcctggaga     120
```

```
tggacccgat ggacatcgtc ggcaagtcca aggaggacgt ctccctcccc aaatcaacaa    180
tgtttaagat aattaaggag atgcttcctc ctgatgtacg agtggcaaga gatgcacagg    240
atcttcttgt tgaatgctgt gtagagttca tcaatctcct ttcgtctgaa tcgaatgaag    300
tgtgcagcag agaagagaaa aaaacgattg ctcctgagca tgttatcaag gctctaagtg    360
atcttggctt cagagagtac attgaggagg tttatgctgc atatgaacag cacaaacttg    420
atactttgga ttctccaaaa gctggcaaat tcactgggat tgagatgaca gaggaagaag    480
ctgttgctga gcaacaaagg atgtttgctg aggctcgagc aaggatgaat aatggagccc    540
ccaaaccaaa ggagacagaa caagagccgc cacagcaacc acaagcacaa ccccaacttc    600
agctgcatac tgaaccacag caacccgtgc aatctcaagt gcagttgcat tcgccaacac    660
agcattccct ccaacctcaa gtgcagctgc accccagcc acaacagctc ccacaagtgc    720
aggtgcactc tcagacgcag ctgcaccctc agccacagca gccccaagtg caggtccatc    780
cgcagctgca gcaactccca caattacagg cccactcgca gccaccgcaa ccccaagtgc    840
aaatccaccc acagccgcag cagccccac aagtgcagtt gcagtcatca gtccagcaga    900
cctcccaacc ccaacctcag gtacatctct acaatcacag ggggggctca caagcgcagc    960
tgcagcccca actgccaggt cagctgcaga cacaggggca aaccggacct ggcattgaca   1020
gttagagact actgctggca tatactagga acctgtatgc ttgcttgtga ctcgttagat   1080
cctgatttag gtttctgtgc ttcctgtaca atgtaaatcc agtgtgattg cagttgcctt   1140
gttgctaata atgtgaaacc gttagttact gatgatgtcc ttactgtgtc gaatactgaa   1200
tgtcatggcg tggcttatgt gccatgctga atgatgttct gtggtcattg taatagccta   1260
acttgacatc tgtccatgat gatagtgatt gatttgaatg aaaaaaaaaa aaaaaa       1316
```

<210> SEQ ID NO 6
<211> LENGTH: 340
<212> TYPE: PRT
<213> ORGANISM: Zea mays

<400> SEQUENCE: 6

```
Thr Arg Pro Ile Pro Leu Cys Pro Ser Lys Pro Asn Cys Arg Pro Asn
 1               5                  10                  15

Ser Leu Ala Gly Ser Thr Cys Tyr Leu Ala Pro Ala Phe Cys Arg Ala
            20                  25                  30

Asp Ser Leu Leu Arg Leu Glu Met Asp Pro Met Asp Ile Val Gly Lys
        35                  40                  45

Ser Lys Glu Asp Val Ser Leu Pro Lys Ser Thr Met Phe Lys Ile Ile
    50                  55                  60

Lys Glu Met Leu Pro Pro Asp Val Arg Val Ala Arg Asp Ala Gln Asp
65                  70                  75                  80

Leu Leu Val Glu Cys Cys Val Glu Phe Ile Asn Leu Ser Ser Glu
                85                  90                  95

Ser Asn Glu Val Cys Ser Arg Glu Lys Lys Thr Ile Ala Pro Glu
            100                 105                 110

His Val Ile Lys Ala Leu Ser Asp Leu Gly Phe Arg Glu Tyr Ile Glu
        115                 120                 125

Glu Val Tyr Ala Ala Tyr Glu Gln His Lys Leu Asp Thr Leu Asp Ser
    130                 135                 140

Pro Lys Ala Gly Lys Phe Thr Gly Ile Glu Met Thr Glu Glu Glu Ala
145                 150                 155                 160
```

-continued

```
Val Ala Glu Gln Gln Arg Met Phe Ala Glu Ala Arg Ala Arg Met Asn
            165                 170                 175
Asn Gly Ala Pro Lys Pro Lys Glu Thr Glu Gln Glu Pro Pro Gln Gln
        180                 185                 190
Pro Gln Ala Gln Pro Gln Leu Gln Leu His Thr Glu Pro Gln Gln Pro
        195                 200                 205
Val Gln Ser Gln Val Gln Leu His Ser Pro Thr Gln His Ser Leu Gln
    210                 215                 220
Pro Gln Val Gln Leu His Pro Gln Pro Gln Gln Leu Pro Gln Val Gln
225                 230                 235                 240
Val His Ser Gln Thr Gln Leu His Pro Gln Pro Gln Pro Gln Val
                245                 250                 255
Gln Val His Pro Gln Leu Gln Gln Leu Pro Gln Leu Gln Ala His Ser
            260                 265                 270
Gln Pro Pro Gln Pro Gln Val Gln Ile His Pro Gln Pro Gln Gln Pro
        275                 280                 285
Pro Gln Val Gln Leu Gln Ser Ser Val Gln Gln Thr Ser Gln Pro Gln
    290                 295                 300
Pro Gln Val His Leu Tyr Asn His Arg Gly Gly Ser Gln Ala Gln Leu
305                 310                 315                 320
Gln Pro Gln Leu Pro Gly Gln Leu Gln Thr Gln Gly Gln Thr Gly Pro
                325                 330                 335
Gly Ile Asp Ser
            340
```

<210> SEQ ID NO 7
<211> LENGTH: 205
<212> TYPE: DNA
<213> ORGANISM: Oryza sp.
<220> FEATURE:
<221> NAME/KEY: unsure
<222> LOCATION: (178)
<223> OTHER INFORMATION: n=a,c,g or t
<220> FEATURE:
<221> NAME/KEY: unsure
<222> LOCATION: (196)
<223> OTHER INFORMATION: n=a,c,g or t

<400> SEQUENCE: 7

```
cttacacatc aacctcctat cttctgaatc caatgaagtt tgcagccgag aggacaagaa    60
aactattgct cctgagcatg ttcttagagc tctgcaggtt tgcctttcat ttcctgaata   120
ttaacattat tttttatcac ttatgatgct gtcctacctg ttttatcatg gtcgtagntt   180
tgtagtacat cgtcancatc atttc                                         205
```

<210> SEQ ID NO 8
<211> LENGTH: 38
<212> TYPE: PRT
<213> ORGANISM: Oryza sp.

<400> SEQUENCE: 8

```
Ile Asn Leu Leu Ser Ser Glu Ser Asn Glu Val Cys Ser Arg Glu Asp
1               5                   10                  15
Lys Lys Thr Ile Ala Pro Glu His Val Leu Arg Ala Leu Gln Val Cys
            20                  25                  30
Leu Ser Phe Pro Glu Tyr
        35
```

<210> SEQ ID NO 9

```
<211> LENGTH: 1322
<212> TYPE: DNA
<213> ORGANISM: Oryza sativa

<400> SEQUENCE: 9
gttaggtgtc gcgcctggag acgcggagat ggatccgatg gatatcgtgg ggaagtccaa      60
ggaggacgtc tccctcccca aatcaacaat gtttaagatt ataaaggaga tgttgccccc     120
tgatgttcga gtggcaagag atgcacaaga tcttcttgtg aatgctgtg tagagttcat      180
caacctccta tcttctgaat ccaatgaagt ttgcagccga gaggacaaga aaactattgc     240
tcctgagcat gttcttagag ctctgcagga tcttggcttt agggagtaca ttgaagaggt     300
tcaagcggcc tacgaacacc ataagcatga taccctggat ctccaaaag caagcaaatt      360
cactggtgtg gagatgacag aggaacaagc tgtagctgag caacagagga tgtttgctga     420
ggcccgagca aggatgaaca atggtgccgc caaaccgaag gagccagaac ctgaagcgca     480
gcaacaaaca caacagccac cacagcctca gctgcaccct caaccacagc aaccctgca      540
gcctcaactt cagctccatc ctcaaccaca acaacagccc tcacagctac atcctcaaca     600
gctgctgcat cctcaatcgc agcaaactcc gcagcctcaa cctcaggtcc accctcaacc     660
acagcagcct ccacagctgc aaccgcaacc tcagcttctc cagcaaccgc agctgcccca     720
acagctgcag ccgcaatctc agctcccccc acaaccgcag cagcccccac agctgcagct     780
gcaatctcag ctccacccac aaccgcagca gcccccacag ctgcagccgc aacctcagct     840
ccatcagcaa ccgcagccgc aggcagagct gcaatcacag tcacaaccac aaacagaaca     900
tggcttggac agttcatgat tcagattcca tgttgtgtag cctcagtata aggaaaagtt     960
ggtgtacttc cgctggcatt tactaggact ctgtgtgccc cttgatagtt ttaggtttcc    1020
atgcttcatg tacaatgtaa atccagtgtg atttcagtta ccatgttgct aataatctga    1080
agctctcttt tgtcactgat gttattactt ttccaaacac cctttctctg actctatgac    1140
tgtagtagta tcatggcatg tatgatgcct tgtcaaaagg gactccatta gcagtgtaac    1200
ttgactttt ccggtggcgg ttgtggtttc cgtggctttt ttaaaaaaaa aaaaaaaaa     1260
aaaaaaaaa aaaaaaaaa aaaaaaaaa aaaaaaata aaaaaaaaa gaaagaaaaa         1320
aa                                                                   1322

<210> SEQ ID NO 10
<211> LENGTH: 296
<212> TYPE: PRT
<213> ORGANISM: Oryza sativa

<400> SEQUENCE: 10

Met Asp Pro Met Asp Ile Val Gly Lys Ser Lys Glu Asp Val Ser Leu
  1               5                  10                  15

Pro Lys Ser Thr Met Phe Lys Ile Ile Lys Glu Met Leu Pro Pro Asp
             20                  25                  30

Val Arg Val Ala Arg Asp Ala Gln Asp Leu Leu Val Glu Cys Cys Val
         35                  40                  45

Glu Phe Ile Asn Leu Leu Ser Glu Ser Asn Glu Val Cys Ser Arg
     50                  55                  60

Glu Asp Lys Lys Thr Ile Ala Pro Glu His Val Leu Arg Ala Leu Gln
 65                  70                  75                  80

Asp Leu Gly Phe Arg Glu Tyr Ile Glu Glu Val Gln Ala Ala Tyr Glu
                 85                  90                  95

His His Lys His Asp Thr Leu Asp Ser Pro Lys Ala Ser Lys Phe Thr
```

```
                100                 105                 110
Gly Val Glu Met Thr Glu Glu Gln Ala Val Ala Glu Gln Gln Arg Met
        115                 120                 125

Phe Ala Glu Ala Arg Ala Arg Met Asn Asn Gly Ala Ala Lys Pro Lys
130                 135                 140

Glu Pro Glu Pro Glu Ala Gln Gln Gln Thr Gln Gln Pro Pro Gln Pro
145                 150                 155                 160

Gln Leu His Pro Gln Pro Gln Pro Leu Gln Pro Gln Leu Gln Leu
            165                 170                 175

His Pro Gln Pro Gln Gln Pro Ser Gln Leu His Pro Gln Gln Leu
        180                 185                 190

Leu His Pro Gln Ser Gln Gln Thr Pro Gln Pro Gln Pro Gln Val His
        195                 200                 205

Pro Gln Pro Gln Gln Pro Pro Gln Leu Gln Pro Gln Pro Gln Leu Leu
    210                 215                 220

Gln Gln Pro Gln Leu Pro Gln Gln Leu Gln Pro Ser Gln Leu Pro
225                 230                 235                 240

Pro Gln Pro Gln Gln Pro Pro Gln Leu Gln Leu Gln Ser Gln Leu His
            245                 250                 255

Pro Gln Pro Gln Gln Pro Pro Gln Leu Gln Pro Gln Pro Gln Leu His
            260                 265                 270

Gln Gln Pro Gln Pro Gln Ala Glu Leu Gln Ser Gln Ser Gln Pro Gln
        275                 280                 285

Thr Glu His Gly Leu Asp Ser Ser
    290                 295

<210> SEQ ID NO 11
<211> LENGTH: 581
<212> TYPE: DNA
<213> ORGANISM: Glycine max
<220> FEATURE:
<221> NAME/KEY: unsure
<222> LOCATION: (331)
<223> OTHER INFORMATION: n=a,c,g or t
<220> FEATURE:
<221> NAME/KEY: unsure
<222> LOCATION: (433)
<223> OTHER INFORMATION: n=a,c,g or t
<220> FEATURE:
<221> NAME/KEY: unsure
<222> LOCATION: (524)
<223> OTHER INFORMATION: n=a,c,g or t
<220> FEATURE:
<221> NAME/KEY: unsure
<222> LOCATION: (534)
<223> OTHER INFORMATION: n=a,c,g or t
<220> FEATURE:
<221> NAME/KEY: unsure
<222> LOCATION: (544)
<223> OTHER INFORMATION: n=a,c,g or t
<220> FEATURE:
<221> NAME/KEY: unsure
<222> LOCATION: (547)
<223> OTHER INFORMATION: n=a,c,g or t
<220> FEATURE:
<221> NAME/KEY: unsure
<222> LOCATION: (555)
<223> OTHER INFORMATION: n=a,c,g or t
<220> FEATURE:
<221> NAME/KEY: unsure
<222> LOCATION: (563)
<223> OTHER INFORMATION: n=a,c,g or t
<220> FEATURE:
<221> NAME/KEY: unsure
<222> LOCATION: (566)
<223> OTHER INFORMATION: n=a,c,g or t
```

```
<220> FEATURE:
<221> NAME/KEY: unsure
<222> LOCATION: (578)
<223> OTHER INFORMATION: n=a,c,g or t

<400> SEQUENCE: 11
gagaaaagca gcaccatcac caccccacc tcttacccct tctttcataa atatgcgtct      60
ctgcaacaac atgttcacca ccacctcctt gttcttcaca tcatcctcat catcttcttc    120
aatcagttga ctcttcgttc ctccctctat tctttcggat ggagcccatg gacatcgttg    180
ggaaggccaa ggaagacgct tctcttccta aagcgacaat gacgaaaatt attaaagaga    240
tgttgccccc ggacgtgcgt gtcgccagag atgcacagga tttattgatc gagtgttgtg    300
tcgagtttat aaaccttgtc tcgtcagagt ncaatgaagt ctgtaacaaa gaagaaagaa    360
ggacgattgc accggagcac gtgttaaagg ctttaggggt tcttggattt ggcgagtaca    420
ttgaagaagt ttntgcagca tatgaacaac acagttggaa aaatgcaga ttctttaaaa     480 ggggcaagtg gagcaacaga gctgagatga ctgaggaaga agcnttggct gaanaccaag    540
gatnttnccg agggncctgc aanataatg gggggccnttt t                        581

<210> SEQ ID NO 12
<211> LENGTH: 98
<212> TYPE: PRT
<213> ORGANISM: Glycine max
<220> FEATURE:
<221> NAME/KEY: UNSURE
<222> LOCATION: (58)
<223> OTHER INFORMATION: Xaa=ANY AMINO ACID
<220> FEATURE:
<221> NAME/KEY: UNSURE
<222> LOCATION: (92)
<223> OTHER INFORMATION: Xaa=ANY AMINO ACID

<400> SEQUENCE: 12

Met Glu Pro Met Asp Ile Val Gly Lys Ala Lys Glu Asp Ala Ser Leu
 1               5                  10                  15

Pro Lys Ala Thr Met Thr Lys Ile Ile Lys Glu Met Leu Pro Pro Asp
            20                  25                  30

Val Arg Val Ala Arg Asp Ala Gln Asp Leu Leu Ile Glu Cys Cys Val
        35                  40                  45

Glu Phe Ile Asn Leu Val Ser Ser Glu Xaa Asn Glu Val Cys Asn Lys
    50                  55                  60

Glu Glu Arg Arg Thr Ile Ala Pro Glu His Val Leu Lys Ala Leu Gly
65                  70                  75                  80

Val Leu Gly Phe Gly Glu Tyr Ile Glu Glu Val Xaa Ala Ala Tyr Glu
                85                  90                  95

Gln His

<210> SEQ ID NO 13
<211> LENGTH: 885
<212> TYPE: DNA
<213> ORGANISM: Glycine max

<400> SEQUENCE: 13
gcacgagaaa agcagcacca tcaccacccc cacctcttac cccttctttc ataaatatgc     60
gtctctgcaa caacatgttc accaccacct ccttgttctt cacatcatcc tcatcatctt    120
cttcaatcag ttgactcttc gttcctcct ctattctttc ggatggagcc catggacatc     180
gttgggaagg ccaaggaaga cgcttctctt cctaaagcga caatgacgaa aattattaaa    240
```

-continued

| | |
|---|---|
| gagatgttgc ccccggacgt gcgtgtcgcc agagatgcac aggatttatt gatcgagtgt | 300 |
| tgtgtcgagt ttataaacct tgtctcgtca gagtccaatg aagtctgtaa caaagaagaa | 360 |
| agaaggacga ttgcaccgga gcacgtgtta aaggctttag gggttcttgg atttggcgag | 420 |
| tacattgagg aagtttatgc agcatatgaa caacacaagt tggaaacaat gcaagattct | 480 |
| ttaaaaggtg caaagtggag caacagagct gagatgactg aggaagaagc attggctgaa | 540 |
| cagcaaagga tgtttgcaga ggcacgtgca agaatgaatg gaggagccat tcaatccaag | 600 |
| gagccagagg ctgaccaaag tttagagagc taactttata ggacactttt attttctttt | 660 |
| gaagcatagg caagcagcat ctcttactct tccctatgcg ttgttaattt agctcgattt | 720 |
| tgcacatacc cccattcact agtttgctgg cctacgtgaa tgtactcgcc atttgtgttc | 780 |
| ttttagtaat ccatatttgt aagttaatgt aattattgga gttcatctaa accctcgtct | 840 |
| atttagaatt ttacatgtag attatttcaa aaaaaaaaaa aaaaa | 885 |

<210> SEQ ID NO 14
<211> LENGTH: 192
<212> TYPE: PRT
<213> ORGANISM: Glycine max

<400> SEQUENCE: 14

Ile Cys Val Ser Ala Thr Thr Cys Ser Pro Pro Pro Cys Ser Ser
1               5                   10                  15

His His Pro His His Leu Leu Gln Ser Val Asp Ser Ser Phe Leu Pro
            20                  25                  30

Leu Phe Phe Arg Met Glu Pro Met Asp Ile Val Gly Lys Ala Lys Glu
        35                  40                  45

Asp Ala Ser Leu Pro Lys Ala Thr Met Thr Lys Ile Ile Lys Glu Met
    50                  55                  60

Leu Pro Pro Asp Val Arg Val Ala Arg Asp Ala Gln Asp Leu Leu Ile
65                  70                  75                  80

Glu Cys Cys Val Glu Phe Ile Asn Leu Val Ser Ser Glu Ser Asn Glu
                85                  90                  95

Val Cys Asn Lys Glu Glu Arg Arg Thr Ile Ala Pro Glu His Val Leu
            100                 105                 110

Lys Ala Leu Gly Val Leu Gly Phe Gly Glu Tyr Ile Glu Glu Val Tyr
        115                 120                 125

Ala Ala Tyr Glu Gln His Lys Leu Glu Thr Met Gln Asp Ser Leu Lys
    130                 135                 140

Gly Ala Lys Trp Ser Asn Arg Ala Glu Met Thr Glu Glu Glu Ala Leu
145                 150                 155                 160

Ala Glu Gln Gln Arg Met Phe Ala Glu Ala Arg Ala Arg Met Asn Gly
                165                 170                 175

Gly Ala Ile Gln Ser Lys Glu Pro Glu Ala Asp Gln Ser Leu Glu Ser
            180                 185                 190

<210> SEQ ID NO 15
<211> LENGTH: 843
<212> TYPE: DNA
<213> ORGANISM: Glycine max

<400> SEQUENCE: 15

| | |
|---|---|
| cttccttcag caactacgat cttcgatagt gatttatcag attcttcctt tgcggtcgaa | 60 |
| tcatggagcc catggacatc gttggtaaat caaaggaaga cgcttcgctt cctaaagcaa | 120 |
| caatgacaaa aattattaaa gagatgttac ccccagattt tataaacctt gtctcgtcag | 180 |

-continued

```
aatccaatga agtctgtaat agagaggata aacggacaat tgcacctgag catgtattga      240
aggctctaca ggttctagga ttttgtgagt acattgaaga agtttatgca gcatatgaac      300
agcacaaact ggagaccatg caggactctt taagaggggg tggtggtggt ggtaaatgga      360
acaatggagc tgagatgact gaggaagaag cattagcaga gcagcaaagg atgttagcag      420
aggcacgtgc taggatgaat ggtggagcca ttgcttctaa gcagccagat gctgaccaaa      480
gtttagatag ctaactttag gatctttatt gaagcatagg caagcaccac cctgactcct      540
cctgtctgtg ctttcaatta gctcgattgt gtacaaaaac cgttcactag tctgccggcc      600
tatgtggatg tgctcatttg tattctatcg atgaatccat atttgtaagt caatgtaatt      660
agtgagagat catgaaaacc ctttcgttta gcatttactt gtaattattt aatttacttt      720
ttgtatcttc tacatactaa caactcctag cttgattctg acagtagcta tatgttagat      780
tgtaacaaat tattaaatat gtagaagcaa tggtgttctg tttaaaaaaa aaaaaaaaaa      840
aaa                                                                    843
```

```
<210> SEQ ID NO 16
<211> LENGTH: 143
<212> TYPE: PRT
<213> ORGANISM: Glycine max

<400> SEQUENCE: 16
```

```
Met Glu Pro Met Asp Ile Val Gly Lys Ser Lys Glu Asp Ala Ser Leu
 1               5                  10                  15

Pro Lys Ala Thr Met Thr Lys Ile Ile Lys Glu Met Leu Pro Pro Asp
            20                  25                  30

Phe Ile Asn Leu Val Ser Ser Glu Ser Asn Glu Val Cys Asn Arg Glu
        35                  40                  45

Asp Lys Arg Thr Ile Ala Pro Glu His Val Leu Lys Ala Leu Gln Val
    50                  55                  60

Leu Gly Phe Cys Glu Tyr Ile Glu Glu Val Tyr Ala Ala Tyr Glu Gln
65                  70                  75                  80

His Lys Leu Glu Thr Met Gln Asp Ser Leu Arg Gly Gly Gly Gly Gly
                85                  90                  95

Gly Lys Trp Asn Asn Gly Ala Glu Met Thr Glu Glu Ala Leu Ala
            100                 105                 110

Glu Gln Gln Arg Met Leu Ala Glu Ala Arg Ala Arg Met Asn Gly Gly
        115                 120                 125

Ala Ile Ala Ser Lys Gln Pro Asp Ala Asp Gln Ser Leu Asp Ser
    130                 135                 140
```

```
<210> SEQ ID NO 17
<211> LENGTH: 509
<212> TYPE: DNA
<213> ORGANISM: Triticum sp.
<220> FEATURE:
<221> NAME/KEY: unsure
<222> LOCATION: (396)
<223> OTHER INFORMATION: n=a,c,g or t
<220> FEATURE:
<221> NAME/KEY: unsure
<222> LOCATION: (415)
<223> OTHER INFORMATION: n=a,c,g or t
<220> FEATURE:
<221> NAME/KEY: unsure
<222> LOCATION: (464)
<223> OTHER INFORMATION: n=a,c,g or t
<220> FEATURE:
<221> NAME/KEY: unsure
```

<222> LOCATION: (495)
<223> OTHER INFORMATION: n=a,c,g or t

<400> SEQUENCE: 17

```
cctaacccta gctaagaatc ccctcccgca accaggtcgt gtctcagggc gcatcgccga      60
aggccaagcc ctccctcccc tagcagcggg ccgcccgttc ccggcgggac gcgccggcgc     120
cggcgcccc aggctcaagc tccgtcgcgc tttcgacggc gagggatgga tccgatggac     180
atcgtgggca agtccaagga ggacgtctcc ctccccaaat caacaatgac caagattatt    240
aaggagatgc taccgcctga tgttcgagta gcaagagata cacaggatct tcttgttgaa    300
tgctgtgtag agttcatcaa tcttctttct tcgggaatcc aatgacgtgt gcagccggga    360
cgacaagaaa actattgccc ctgaacatgt tattanggct ttgcaggatc ttggnttcaa    420
ggagtatgtt gaagaagttt atgcagccta cgaacaacac aagnttgaaa cctggactct    480
caaaagcaac caaantcact ggcatagaa                                       509
```

<210> SEQ ID NO 18
<211> LENGTH: 113
<212> TYPE: PRT
<213> ORGANISM: Triticum sp.
<220> FEATURE:
<221> NAME/KEY: UNSURE
<222> LOCATION: (57)
<223> OTHER INFORMATION: Xaa=ANY AMINO ACID
<220> FEATURE:
<221> NAME/KEY: UNSURE
<222> LOCATION: (77)
<223> OTHER INFORMATION: Xaa=ANY AMINO ACID
<220> FEATURE:
<221> NAME/KEY: UNSURE
<222> LOCATION: (100)
<223> OTHER INFORMATION: Xaa=ANY AMINO ACID
<220> FEATURE:
<221> NAME/KEY: UNSURE
<222> LOCATION: (110)
<223> OTHER INFORMATION: Xaa=ANY AMINO ACID

<400> SEQUENCE: 18

```
Met Asp Pro Met Asp Ile Val Gly Lys Ser Lys Glu Asp Val Ser Leu
 1               5                  10                  15

Pro Lys Ser Thr Met Thr Lys Ile Ile Lys Glu Met Leu Pro Pro Asp
            20                  25                  30

Val Arg Val Ala Arg Asp Thr Gln Asp Leu Leu Val Glu Cys Cys Val
        35                  40                  45

Glu Phe Ile Asn Leu Leu Ser Ser Xaa Ser Asn Asp Val Cys Ser Arg
    50                  55                  60

Asp Asp Lys Lys Thr Ile Ala Pro Glu His Val Ile Xaa Ala Leu Gln
65                  70                  75                  80

Asp Leu Gly Phe Lys Glu Tyr Val Glu Glu Val Tyr Ala Ala Tyr Glu
                85                  90                  95

Gln His Lys Xaa Glu Thr Trp Thr Leu Lys Ser Asn Gln Xaa His Trp
            100                 105                 110

His
```

<210> SEQ ID NO 19
<211> LENGTH: 1463
<212> TYPE: DNA
<213> ORGANISM: Triticum aestivum

<400> SEQUENCE: 19

```
gcacgagcct aaccctagct aagaatcccc tcccgcaacc aggtcgtgtc tcagggcgca     60
```

-continued

```
tcgccgaagg ccaagccctc cctcccctag cagcgggccg cccgttcccg gcgggacgcg        120
ccggcgccgg cgcccccagg ctcaagctcc gtcgcgcttt cgacggcgag ggatggatcc        180
gatggacatc gtgggcaagt ccaaggagga cgtctccctc cccaaatcaa caatgaccaa        240
gattattaag gagatgctac cgcctgatgt tcgagtagca agagatacac aggatcttct        300
tgttgaatgc tgtgtagagt tcatcaatct tctttcttcg gaatccaatg acgtgtgcag        360
ccgggacgac aagaaaacta ttgcccctga acatgttatt agggctttgc aggatcttgg        420
cttcaaggag tatgttgaag aagtttatgc agcctacgaa cagcacaagc ttgaaaccct        480
ggactctcca aaagcaacca agttcactgg catagagatg acagaagaag aagctgttgc        540
tgaacagcag agaatgtttg ctgaagcccg agcaaggatg aacaatggag ctgccaaacc        600
aaaggagcct gcattagaac cacagaatca accccaacag cccccacaac ctcatctgca        660
gctgcatcct caagcacagc agcctccaca acctcaaccg caactgcatc atcctcaatc        720
acagcagccc ctgcatcctc aactgcaacc gtatactcag gctccaccac agcagcccct        780
gcatcctcaa ctgcaaccgt atactcaggc tccaccacag caaccctac aacctccact        840 gcagctgtat cctcaggctc aacctgagca accctgcag cctcaatcct caggatcaac        900
cacaggaacc tgtgtaatct caactgccgc tccatctgca accggcacca ctgctgctgc        960
aacctccgcc ccagcaatcc ccgcaatctc aactgcagct ccatcagcaa ccccagccga       1020
tgcaagtgcc gctgccgccg ctgccgcaac ctcaaccca gccacctgaa ctgcagcagc       1080
cccagccgct aacacaactg caagcggaac atggcctgaa ctggacagtt agtggttcgg       1140
aacatgtagc gtcactataa gttaagactc tgcctccttt aaaattgtgc gttaggtttg       1200
cctgcatctt gtacaatgta atcgtgtgt gatttcagcc accgtgtctc taataatctg       1260
aagctctcta gtaagcgatg tacttactgc gctggatact gtgtttatga ctgttgtagt       1320
ctcatggtat tgtgtgtgac gtgtcagaag ctactccatt accagtgtaa tcaattgcct       1380
gacttaatgt tcacccgtga tgatagtaat tgatttcagt gtgctaaaaa aaaaaaaaaa       1440
aaaaaaaaaa aaaaaaaaaa aaa                                               1463
```

<210> SEQ ID NO 20
<211> LENGTH: 348
<212> TYPE: PRT
<213> ORGANISM: Triticum aestivum

<400> SEQUENCE: 20

```
Glu Ser Pro Pro Ala Thr Arg Ser Cys Leu Arg Ala His Arg Arg Arg
 1               5                   10                  15

Pro Ser Pro Pro Ser Pro Ser Ser Gly Pro Pro Val Pro Gly Gly Thr
            20                  25                  30

Arg Arg Arg Arg Arg Pro Gln Ala Gln Ala Pro Ser Arg Phe Arg Arg
        35                  40                  45

Arg Gly Met Asp Pro Met Asp Ile Val Gly Lys Ser Lys Glu Asp Val
    50                  55                  60

Ser Leu Pro Lys Ser Thr Met Thr Lys Ile Ile Lys Glu Met Leu Pro
65                  70                  75                  80

Pro Asp Val Arg Val Ala Arg Asp Thr Gln Asp Leu Leu Val Glu Cys
                85                  90                  95

Cys Val Glu Phe Ile Asn Leu Leu Ser Ser Glu Ser Asn Asp Val Cys
            100                 105                 110

Ser Arg Asp Asp Lys Lys Thr Ile Ala Pro Glu His Val Ile Arg Ala
```

```
                115                 120                 125
Leu Gln Asp Leu Gly Phe Lys Glu Tyr Val Glu Val Tyr Ala Ala
        130                 135                 140

Tyr Glu Gln His Lys Leu Glu Thr Leu Asp Ser Pro Lys Ala Thr Lys
145                 150                 155                 160

Phe Thr Gly Ile Glu Met Thr Glu Glu Ala Val Ala Glu Gln Gln
                165                 170                 175

Arg Met Phe Ala Glu Ala Arg Ala Arg Met Asn Asn Gly Ala Ala Lys
            180                 185                 190

Pro Lys Glu Pro Ala Leu Glu Pro Gln Asn Gln Pro Gln Pro Pro
        195                 200                 205

Gln Pro His Leu Gln Leu His Pro Gln Ala Gln Pro Pro Gln Pro
    210                 215                 220

Gln Pro Gln Leu His His Pro Gln Ser Gln Gln Pro Leu His Pro Gln
225                 230                 235                 240

Leu Gln Pro Tyr Thr Gln Ala Pro Pro Gln Gln Pro Leu His Pro Gln
                245                 250                 255

Leu Gln Pro Tyr Thr Gln Ala Pro Pro Gln Gln Pro Leu Gln Pro Pro
            260                 265                 270

Leu Gln Leu Tyr Pro Gln Ala Gln Pro Glu Gln Pro Leu Gln Pro Gln
        275                 280                 285

Ser Ser Gly Ser Thr Thr Gly Thr Cys Val Ile Ser Thr Ala Ala Pro
    290                 295                 300

Ser Ala Thr Gly Thr Thr Ala Ala Ala Thr Ser Ala Pro Ala Ile Pro
305                 310                 315                 320

Ala Ile Ser Thr Ala Ala Pro Ser Ala Thr Pro Ala Asp Ala Ser Ala
                325                 330                 335

Ala Ala Ala Ala Ala Ala Thr Ser Thr Pro Ala Thr
            340                 345

<210> SEQ ID NO 21
<211> LENGTH: 1288
<212> TYPE: DNA
<213> ORGANISM: Triticum aestivum

<400> SEQUENCE: 21
ggcacgagcc caagctccgt cgcgcgctcg acggcgaggg atggatccga tggacatcgt    60
gggcaagtcc aaggaggacg tctccctccc caaatcaaca atgaccaaga ttatcaagga   120
gatgctaccg cctgatgttc gagtagcaag agatacacag gatcttcttg ttgaatgctg   180
tgtagagttc atcaatcttc tttcttcgga atccaatgac gtgtgcagcc gggacgacaa   240
gaaaactatt gccctgaac atgttattag gctttgcag gatcttggct tcaaggagta    300
tgttgaagaa gtttatgcag cctacgaaca gcacaagctt gaaactctgg actctccaaa   360
agcaaccaag ttcactggta tagagatgac tgaagaagaa gctgttgctg aacagcagag   420
aatgtttgct gaagcccgag caaggatgaa caatggagct gccaaaccaa aggagcctgc   480
attagaacca cagaatcaac cccaacagcc cccacaacct catctgcagc tgcatcccca   540
agcacagcag cctccacaac tcaaccgca actgcattat cctcaatcac agcagcccct    600
gcaaccgttt actcaggctc caccacagca accctgcat cctcaactgc aacagtatac    660
tcaggctcca ccacagcaac cctacaacc tccactgcag ctgtatcctc aggctcaacc   720
tgagcaaccg ctgcagcctc aatcctcagg atcaaccaca ggaacctgtg taatctcagc   780
tgcagctcca tctgcaaccg gcacactgct gctgcaacct ccgccccagc aatccccgca   840
```

```
atctcaactg cagctccatc agcaacccca gccgacgcta gtgccgccgc cgcaacctca    900
accccagcca cttgaactgc agcagcccca gccgctaaca caactgcaag cggaacatgg    960
cctggactgg gacagttagt ggttcggaac atgtagcgtc actataagtt aagactctgc   1020
ctcctttaaa attgtgcgtt aggtttgcct gcatcttgta caatgtaaat cgtgtgtgat   1080
ttcagccacc gtgtctaata atctgaagct ctctagtaag cgatgtactt actgcgctgg   1140
gtactgtgtt tatgactgct gtagtctcat ggtattgtgt gtgacgtgtc agaagctact   1200
ccattaccag tgtaatcaat tgcctaactt aatgttcacc cgtgatgata aaaaaaaaa    1260
aaaaaaaaaa aaaaaaaaaa aaaaaaa                                       1288
```

<210> SEQ ID NO 22
<211> LENGTH: 312
<212> TYPE: PRT
<213> ORGANISM: Triticum aestivum

<400> SEQUENCE: 22

```
Met Asp Pro Met Asp Ile Val Gly Lys Ser Lys Glu Asp Val Ser Leu
 1               5                  10                  15

Pro Lys Ser Thr Met Thr Lys Ile Ile Lys Glu Met Leu Pro Pro Asp
             20                  25                  30

Val Arg Val Ala Arg Asp Thr Gln Asp Leu Leu Val Glu Cys Cys Val
         35                  40                  45

Glu Phe Ile Asn Leu Leu Ser Ser Glu Ser Asn Asp Val Cys Ser Arg
     50                  55                  60

Asp Asp Lys Lys Thr Ile Ala Pro Glu His Val Ile Arg Ala Leu Gln
 65                  70                  75                  80

Asp Leu Gly Phe Lys Glu Tyr Val Glu Val Tyr Ala Ala Tyr Glu
                 85                  90                  95

Gln His Lys Leu Glu Thr Leu Asp Ser Pro Lys Ala Thr Lys Phe Thr
            100                 105                 110

Gly Ile Glu Met Thr Glu Glu Ala Val Ala Glu Gln Gln Arg Met
        115                 120                 125

Phe Ala Glu Ala Arg Ala Arg Met Asn Asn Gly Ala Ala Lys Pro Lys
130                 135                 140

Glu Pro Ala Leu Glu Pro Gln Asn Gln Pro Gln Gln Pro Pro Gln Pro
145                 150                 155                 160

His Leu Gln Leu His Pro Gln Ala Gln Gln Pro Pro Gln Pro Gln Pro
                165                 170                 175

Gln Leu His Tyr Pro Gln Ser Gln Gln Pro Leu Gln Pro Phe Thr Gln
            180                 185                 190

Ala Pro Pro Gln Gln Pro Leu His Pro Gln Leu Gln Gln Tyr Thr Gln
        195                 200                 205

Ala Pro Pro Gln Gln Pro Leu Gln Pro Leu Gln Leu Tyr Pro Gln
210                 215                 220

Ala Gln Pro Glu Gln Pro Leu Gln Pro Gln Ser Ser Gly Ser Thr Thr
225                 230                 235                 240

Gly Thr Cys Val Ile Ser Ala Ala Ala Pro Ser Ala Thr Gly Thr Leu
                245                 250                 255

Leu Leu Gln Pro Pro Gln Gly Ser Pro Gln Ser Gln Leu Gln Leu
            260                 265                 270

His Gln Gln Pro Gln Pro Thr Leu Val Pro Pro Gln Pro Gln Pro
        275                 280                 285
```

```
Gln Pro Leu Glu Leu Gln Gln Pro Gln Pro Leu Thr Gln Leu Gln Ala
    290                 295                 300

Glu His Gly Leu Asp Trp Asp Ser
305                 310
```

<210> SEQ ID NO 23
<211> LENGTH: 1001
<212> TYPE: DNA
<213> ORGANISM: Zea mays

<400> SEQUENCE: 23

```
aggaggcgga ggcgaagatg aggaagaagc tcggcacccg gttccccgcg gctcgaatca    60
aaaagataat gcaagcagat gaggatgttg gaaagattgc actagcagtt cctgttttag   120
tttcgaggtc tcttgaattg ttttttacaag atttaattga ccgtacttat gaaattactc   180
ttcaaagtgg agcaaagaca ctgaattcct tccacctgaa gcaatgtgtg aagaggtaca   240
gttcttttga tttcctaact gaagttgtca gcaaggtacc agatcttggt ggcgctgatt   300
cctgtggaga tgaaagagga ttacctagaa gaagaaagtc aaatggcagt gacccagaga   360
atgatgaatc aagatctagt aaaatggcca taagaaatgc aaacatcagc cccagaggaa   420
cgtgggaggg gtcgaggcag aggacgaggt cggccaccaa ccaagagaaa ggaggttggt   480
tatgtacaat tgaagatgaa gagcagcatg tttgctgaac aaggtgagcc cttgccagga   540
gaggaaacag ttcaagagat caatggcaac gagaccatgc ctcaaagcac gcaacctcca   600
gtagagtccg ccaacagccc ttgcacaagc tacaacaagt tctaaggcgg aagaagcgaa   660
cagtgatcat cagtcagatt ggcctatgcc agatgccatt ggaagcatcg gtgtcgtgcc   720
atctggtttt ggacatctga cagtgcaggt tgaagatgag gactacgaca atgaggatta   780
gtcagggtca tcttctcatt gtatgcacta acaggactgt tctggtgttg taaaatgtaa   840
atatagtttg aaatagttgc cgcagtttac ctgtgattgt ctgtcgtttt atgcggttat   900
gtagtcctgt gtaactttcg ttctccaata attgcttggt agttgctttt ttacatgatt   960
caagtgtttt gtgacaaaaa aaaaaaaaaa aaaaaaaaa a                         1001
```

<210> SEQ ID NO 24
<211> LENGTH: 158
<212> TYPE: PRT
<213> ORGANISM: Zea mays

<400> SEQUENCE: 24

```
Met Arg Lys Lys Leu Gly Thr Arg Phe Pro Ala Ala Arg Ile Lys Lys
  1               5                  10                  15

Ile Met Gln Ala Asp Glu Asp Val Gly Lys Ile Ala Leu Ala Val Pro
             20                  25                  30

Val Leu Val Ser Arg Ser Leu Glu Leu Phe Leu Gln Asp Leu Ile Asp
         35                  40                  45

Arg Thr Tyr Glu Ile Thr Leu Gln Ser Gly Ala Lys Thr Leu Asn Ser
     50                  55                  60

Phe His Leu Lys Gln Cys Val Lys Arg Tyr Ser Ser Phe Asp Phe Leu
 65                  70                  75                  80

Thr Glu Val Val Ser Lys Val Pro Asp Leu Gly Gly Ala Asp Ser Cys
                 85                  90                  95

Gly Asp Glu Arg Gly Leu Pro Arg Arg Arg Lys Ser Asn Gly Ser Asp
            100                 105                 110

Pro Glu Asn Asp Glu Ser Arg Ser Ser Lys Met Ala Ile Arg Asn Ala
        115                 120                 125
```

Asn Ile Ser Pro Arg Gly Thr Trp Glu Gly Ser Arg Gln Arg Thr Arg
    130                 135                 140

Ser Ala Thr Asn Gln Glu Lys Gly Gly Trp Leu Cys Thr Ile
145                 150                 155

<210> SEQ ID NO 25
<211> LENGTH: 562
<212> TYPE: DNA
<213> ORGANISM: Zea mays
<220> FEATURE:
<221> NAME/KEY: unsure
<222> LOCATION: (402)
<223> OTHER INFORMATION: n=a,c,g or t
<220> FEATURE:
<221> NAME/KEY: unsure
<222> LOCATION: (419)
<223> OTHER INFORMATION: n=a,c,g or t
<220> FEATURE:
<221> NAME/KEY: unsure
<222> LOCATION: (423)
<223> OTHER INFORMATION: n=a,c,g or t
<220> FEATURE:
<221> NAME/KEY: unsure
<222> LOCATION: (439)
<223> OTHER INFORMATION: n=a,c,g or t
<220> FEATURE:
<221> NAME/KEY: unsure
<223> OTHER INFORMATION: n=a,c,g or t
<220> FEATURE:
<221> NAME/KEY: unsure
<222> LOCATION: (459)
<223> OTHER INFORMATION: n=a,c,g or t
<220> FEATURE:
<221> NAME/KEY: unsure
<222> LOCATION: (500)
<223> OTHER INFORMATION: n=a,c,g or t
<220> FEATURE:
<221> NAME/KEY: unsure
<222> LOCATION: (504)
<223> OTHER INFORMATION: n=a,c,g or t
<220> FEATURE:
<221> NAME/KEY: unsure
<222> LOCATION: (509)
<223> OTHER INFORMATION: n=a,c,g or t
<220> FEATURE:
<221> NAME/KEY: unsure
<222> LOCATION: (514)
<223> OTHER INFORMATION: n=a,c,g or t
<220> FEATURE:
<221> NAME/KEY: unsure
<222> LOCATION: (518)
<223> OTHER INFORMATION: n=a,c,g or t
<220> FEATURE:
<221> NAME/KEY: unsure
<222> LOCATION: (520)
<223> OTHER INFORMATION: n=a,c,g or t
<220> FEATURE:
<221> NAME/KEY: unsure
<222> LOCATION: (525)
<223> OTHER INFORMATION: n=a,c,g or t
<220> FEATURE:
<221> NAME/KEY: unsure
<222> LOCATION: (533)
<223> OTHER INFORMATION: n=a,c,g or t
<220> FEATURE:
<221> NAME/KEY: unsure
<222> LOCATION: (536)
<223> OTHER INFORMATION: n=a,c,g or t
<220> FEATURE:
<221> NAME/KEY: unsure
<222> LOCATION: (542)
<223> OTHER INFORMATION: n=a,c,g or t

<400> SEQUENCE: 25
cgacagcgtc cgtcgaaccg gagggtcgga ggcggaggcg aagatgagga agaagctcgg     60

```
cacccggttc cccgcggctc gaatcaaaaa gataatgcaa gcagatgagg atgttggaaa      120
gattgcatta gcagtgcctg ttttagtctc gagggctctt gaattgtttt tacaagattt      180
aattgaccgg acttatgaaa ttactcttca aagtggagca aagacactga attccttcca      240
cctgaagcaa tgtgtgaaga ggtacagttc ttttgatttc ctaactgaat tgtcagcaag      300
taccagatct tggtggtgct gatcatgtgg agatgaaaga gtgttactag aagaagaaat      360
caaatggcat gaccagagaa tgataatcaa atcagtaaat gntatagaaa tcaatacanc      420
canagactgg agggtcagna angcaagcgc acaccagana agattgtact cattaaataa      480
cacagttcga cagggaactn cagnaggana tcanttanan gacantaccc aanagnactg      540
cnaacctgca gtaatcaggg aa                                              562
```

```
<210> SEQ ID NO 26
<211> LENGTH: 86
<212> TYPE: PRT
<213> ORGANISM: Zea mays

<400> SEQUENCE: 26
```

```
Met Arg Lys Lys Leu Gly Thr Arg Phe Pro Ala Ala Arg Ile Lys Lys
 1               5                  10                  15

Ile Met Gln Ala Asp Glu Asp Val Gly Lys Ile Ala Leu Ala Val Pro
            20                  25                  30

Val Leu Val Ser Arg Ala Leu Glu Leu Phe Leu Gln Asp Leu Ile Asp
        35                  40                  45

Arg Thr Tyr Glu Ile Thr Leu Gln Ser Gly Ala Lys Thr Leu Asn Ser
    50                  55                  60

Phe His Leu Lys Gln Cys Val Lys Arg Tyr Ser Ser Phe Asp Phe Leu
65                  70                  75                  80

Thr Glu Leu Ser Ala Ser
                85
```

```
<210> SEQ ID NO 27
<211> LENGTH: 1055
<212> TYPE: DNA
<213> ORGANISM: Zea mays

<400> SEQUENCE: 27
cgacagcgtc cgtcgaaccg gagggtcgga ggcggaggcg aagatgagga agaagctcgg      60
cacccggttc cccgcggctc gaatcaaaaa gataatgcaa gcagatgagg atgttggaaa     120
gattgcatta gcagtgcctg ttttagtctc gagggctctt gaattgtttt tacaagattt     180
aattgaccgg acttatgaaa ttactcttca aagtggagca aagacactga attccttcca     240
cctgaagcaa tgtgtgaaga ggtacagttc ttttgatttc ctaactgaag ttgtcagcaa     300
ggtaccagat cttggtggtg ctgattcatg tggagatgaa agagtgttac ctagaagaag     360
aaagtcaaat ggcagtgacc agagaatga tgaatcaaga tctagtaaaa tggctataag     420
aaatgcaaat accagcccca gaggacgtgg gaggggtcga ggcagagggc gaggtcggcc     480
accaaccaag agaaaggaag ttggttacgt acaatttgaa gatgagagca gcatgtttgc     540
tgaacaaggt gaaaccttac caggagaggg aacagttcca gagatcaaca gcggcaacga     600
gattacgcct caaagcacgc aacctccgct aacagcccct gcgcaagcta caaattctaa     660
ggtggaagaa gcaagcaccg atcatcagtc agattggcct atgccagatg ccactggaaa     720
catcggtgtt gggccatctg gttttggaca tctgacagtg caggttgatg aagatgagga     780
```

```
ctacgacaat gaggactagt cagggccatc ctctcactgt atgcgctaac aggactgttc      840
tggtgttgta aaatgtaaat atagcttgaa gtagctgccg cagcttagct atgattgtct      900
gttatgaggt tatgtagttg ccctgtgtaa cttctgtaat tgcttttag ttgccttttc       960 tctacatgat tgactgtcaa agcgttttgt catatttaac ccagtatgtt tgagcagggg     1020
tcgactattt ctaagtaaaa aaaaaaaaaa aaaaa                                1055
```

<210> SEQ ID NO 28
<211> LENGTH: 251
<212> TYPE: PRT
<213> ORGANISM: Zea mays

<400> SEQUENCE: 28

```
Met Arg Lys Lys Leu Gly Thr Arg Phe Pro Ala Ala Arg Ile Lys Lys
 1               5                  10                  15

Ile Met Gln Ala Asp Glu Asp Val Gly Lys Ile Ala Leu Ala Val Pro
            20                  25                  30

Val Leu Val Ser Arg Ala Leu Glu Leu Phe Leu Gln Asp Leu Ile Asp
        35                  40                  45

Arg Thr Tyr Glu Ile Thr Leu Gln Ser Gly Ala Lys Thr Leu Asn Ser
    50                  55                  60

Phe His Leu Lys Gln Cys Val Lys Arg Tyr Ser Ser Phe Asp Phe Leu
65                  70                  75                  80

Thr Glu Val Val Ser Lys Val Pro Asp Leu Gly Gly Ala Asp Ser Cys
                85                  90                  95

Gly Asp Glu Arg Val Leu Pro Arg Arg Arg Lys Ser Asn Gly Ser Asp
            100                 105                 110

Pro Glu Asn Asp Glu Ser Arg Ser Ser Lys Met Ala Ile Arg Asn Ala
        115                 120                 125

Asn Thr Ser Pro Arg Gly Arg Gly Arg Gly Arg Gly Arg Gly
    130                 135                 140

Arg Pro Pro Thr Lys Arg Lys Glu Val Gly Tyr Val Gln Phe Glu Asp
145                 150                 155                 160

Glu Ser Ser Met Phe Ala Glu Gln Gly Glu Thr Leu Pro Gly Glu Gly
                165                 170                 175

Thr Val Pro Glu Ile Asn Ser Gly Asn Glu Ile Thr Pro Gln Ser Thr
            180                 185                 190

Gln Pro Pro Leu Thr Ala Pro Ala Gln Ala Thr Asn Ser Lys Val Glu
        195                 200                 205

Glu Ala Ser Thr Asp His Gln Ser Asp Trp Pro Met Pro Asp Ala Thr
    210                 215                 220

Gly Asn Ile Gly Val Gly Pro Ser Gly Phe Gly His Leu Thr Val Gln
225                 230                 235                 240

Val Asp Glu Asp Glu Asp Tyr Asp Asn Glu Asp
                245                 250
```

<210> SEQ ID NO 29
<211> LENGTH: 543
<212> TYPE: DNA
<213> ORGANISM: Oryza sp.
<220> FEATURE:
<221> NAME/KEY: unsure
<222> LOCATION: (388)
<223> OTHER INFORMATION: n=a,c,g or t
<220> FEATURE:
<221> NAME/KEY: unsure
<222> LOCATION: (389)
<223> OTHER INFORMATION: n=a,c,g or t

```
<220> FEATURE:
<221> NAME/KEY: unsure
<222> LOCATION: (412)
<223> OTHER INFORMATION: n=a,c,g or t
<220> FEATURE:
<221> NAME/KEY: unsure
<222> LOCATION: (417)
<223> OTHER INFORMATION: n=a,c,g or t
<220> FEATURE:
<221> NAME/KEY: unsure
<222> LOCATION: (447)
<223> OTHER INFORMATION: n=a,c,g or t
<220> FEATURE:
<221> NAME/KEY: unsure
<222> LOCATION: (458)
<223> OTHER INFORMATION: n=a,c,g or t
<220> FEATURE:
<221> NAME/KEY: unsure
<222> LOCATION: (469)
<223> OTHER INFORMATION: n=a,c,g or t
<220> FEATURE:
<221> NAME/KEY: unsure
<222> LOCATION: (469)
<223> OTHER INFORMATION: n=a,c,g or t
<220> FEATURE:
<221> NAME/KEY: unsure
<222> LOCATION: (483)
<223> OTHER INFORMATION: n=a,c,g or t
<220> FEATURE:
<221> NAME/KEY: unsure
<222> LOCATION: (489)
<223> OTHER INFORMATION: n=a,c,g or t
<220> FEATURE:
<221> NAME/KEY: unsure
<222> LOCATION: (509)
<223> OTHER INFORMATION: n=a,c,g or t
<220> FEATURE:
<221> NAME/KEY: unsure
<222> LOCATION: (514)
<223> OTHER INFORMATION: n=a,c,g or t
<220> FEATURE:
<221> NAME/KEY: unsure
<222> LOCATION: (516)
<223> OTHER INFORMATION: n=a,c,g or t

<400> SEQUENCE: 29
ctgcgatagc gtggaggagc ggaggcggag gcgaacgcga ggaggaagac gaagatgagg      60
aagaagctgg gcacccgctt ccccgcggca cggatcaaaa agatcatgca ggctgatgag     120
gacgttggca agattgcact agctgtacct gttttagtat cgaggcccct tgaattgttt     180
ttgcaagatt taattgaccg aacttacgaa attacactgc aaagtggtgc aaagacattg     240
aattccttcc acctaaagca atgtgtgagg aggtacattc ttttgacttc ctaactgagt     300
tgtcaacaag gtaccggacc tcggtggcgc tgaccatgtg gagatgatag agcattaccc     360
agaagaagaa aaccttgcca aatggaantg ccannagaat gaggatccca tnaagcnaat     420
ggccttaaga atgcaaatac atcccanagg acttgganaa gccaagtana ggcaaggaca     480
cancacaanc gaaggattgt aagtcattna ggtnanacac atttgcgata gggcaaccta     540
cag                                                                  543

<210> SEQ ID NO 30
<211> LENGTH: 71
<212> TYPE: PRT
<213> ORGANISM: Oryza sp.

<400> SEQUENCE: 30

Met Arg Lys Lys Leu Gly Thr Arg Phe Pro Ala Ala Arg Ile Lys Lys
 1               5                  10                  15

Ile Met Gln Ala Asp Glu Asp Val Gly Lys Ile Ala Leu Ala Val Pro
```

```
                   20                  25                  30
Val Leu Val Ser Arg Ala Leu Glu Leu Phe Leu Gln Asp Leu Ile Asp
        35                  40                  45

Arg Thr Tyr Glu Ile Thr Leu Gln Ser Gly Ala Lys Thr Leu Asn Ser
    50                  55                  60

Phe His Leu Lys Gln Cys Val
65                  70

<210> SEQ ID NO 31
<211> LENGTH: 1024
<212> TYPE: DNA
<213> ORGANISM: Oryza sativa

<400> SEQUENCE: 31
ctgcgatagc gtggaggagc ggaggcggag gcgaacgcga ggaggaagac gaagatgagg     60
aagaagctgg gcacccgctt ccccgcggca cggatcaaaa agatcatgca ggctgatgag    120
gacgttggca agattgcact agctgtacct gttttagtat cgaggcccct tgaattgttt    180
ttgcaagatt taattgaccg aacttacgaa attacactgc aaagtggtgc aaagacattg    240
aattccttcc acctaaagca atgtgtgagg aggtacagtt cttttgactt cctaactgag    300
gttgtcaaca aggtaccgga cctcggtggc gctgactcat gtggagatga tagagcatta    360
cccagaagaa gaaaagcctt gccaaatgga agtgacccag agaatgagga atctcgatca    420
agcaaaatgg ccgtaagaag tgcaaatatc agtcccagag acgtgggag aggtcgaggt    480 agagggcgag gacgaccacc caccaagcgg aaggaagttg gttatgtaca atttgaggat    540
gagagcagca tgtttgctga tcagggcgaa gccttaccag agaggagac ggttccagag    600 accatccatg gcaccgagag cgtacctcca agcacacacc ctccagcaga agccccatcg    660
gcagcagaga taccagctcc aaatccaaag gtggaagaag cgaaaaacga cgaccatcag    720
ccggattggc ctatgccaga tgcgattgga acatcggtg tcggaccatc cggttttgga    780
catcttacgg tgcaagttga cgaggatgag gactacgaca acgaggatta gccacggcca    840
tcttctgatt gttatgcact aacagggcag ttctcctggt gttgtaaaat gtaaatatgt    900
agctgcagct agctgtgatg tgctgctgat gtaatgcagt atgtagttgt cccgtgtaac    960
tttgtctgtt ttccaataat tgcttgctag ttgcctcaca ttgttgaaaa aaaaaaaaaa   1020
aaaa                                                                1024

<210> SEQ ID NO 32
<211> LENGTH: 258
<212> TYPE: PRT
<213> ORGANISM: Oryza sativa

<400> SEQUENCE: 32

Met Arg Lys Lys Leu Gly Thr Arg Phe Pro Ala Ala Arg Ile Lys Lys
1               5                   10                  15

Ile Met Gln Ala Asp Glu Asp Val Gly Lys Ile Ala Leu Ala Val Pro
            20                  25                  30

Val Leu Val Ser Arg Ala Leu Glu Leu Phe Leu Gln Asp Leu Ile Asp
        35                  40                  45

Arg Thr Tyr Glu Ile Thr Leu Gln Ser Gly Ala Lys Thr Leu Asn Ser
    50                  55                  60

Phe His Leu Lys Gln Cys Val Arg Arg Tyr Ser Ser Phe Asp Phe Leu
65                  70                  75                  80

Thr Glu Val Val Asn Lys Val Pro Asp Leu Gly Gly Ala Asp Ser Cys
```

```
                    85                  90                  95
Gly Asp Asp Arg Ala Leu Pro Arg Arg Lys Ala Leu Pro Asn Gly
            100                 105                 110
Ser Asp Pro Glu Asn Glu Glu Ser Arg Ser Lys Met Ala Val Arg
            115                 120                 125
Ser Ala Asn Ile Ser Pro Arg Gly Arg Gly Arg Gly Arg Gly
        130                 135                 140
Arg Gly Arg Pro Pro Thr Lys Arg Lys Glu Val Gly Tyr Val Gln Phe
145                 150                 155                 160
Glu Asp Glu Ser Ser Met Phe Ala Asp Gln Gly Glu Ala Leu Pro Gly
                165                 170                 175
Glu Glu Thr Val Pro Glu Thr Ile His Gly Thr Glu Ser Val Pro Pro
            180                 185                 190
Ser Thr His Pro Pro Ala Glu Ala Pro Ser Ala Ala Glu Ile Pro Ala
            195                 200                 205
Pro Asn Pro Lys Val Glu Ala Lys Asn Asp Asp His Gln Pro Asp
        210                 215                 220
Trp Pro Met Pro Asp Ala Ile Gly Asn Ile Gly Val Gly Pro Ser Gly
225                 230                 235                 240
Phe Gly His Leu Thr Val Gln Val Asp Glu Asp Glu Asp Tyr Asp Asn
                245                 250                 255
Glu Asp

<210> SEQ ID NO 33
<211> LENGTH: 1274
<212> TYPE: DNA
<213> ORGANISM: Glycine max

<400> SEQUENCE: 33
ctgaaatgag tttcttcgat ttcatcctgt tgatgatagg gtcgctctct ctgttcaaag    60
ctttcgattt tactttctgg gtctccttct tctgcttctt ttgattcccc caattcttca   120
gctttcaaaa ccctaatctg ctgccatgag gaagaagctc gataccgtt tccctgctgc   180
tcggataaag aagataatgc aagctgatga ggatgttgga agatagcac tcgctgtgcc   240
tgttttagtt tctaaagctc tagaactatt tttgcaagat ctttgtgacc gcacttatga   300
aataactctt caaagaggag caaagaccat gaattcattg catttaaaac attgtgtaca   360
aagctataat gtctttgact ttctgaggga cgttgttagc agggttcctg actacagcca   420
tggccatggc catgctgagg ctggtcctga tgatcgggcc attgcaaaaa gaaggaaagc   480
tgttggtgat gatggtaatg acagtgatga agaggctaag aggagcaaga tgcatgagtt   540
gggccacact ggcagtactg gtaggggaag aggccgaggt agaggaagag gccgtggccg   600
agggcgacca cctttaaata gagagatata tcatcaggat gctgaatctg agccttgcac   660
ttctgttcag ccaagcaacc cacaaaatac aaacacaagt gttgcaatgg atagtggttc   720
tgagtcaaag gaaataccaa aggagcagaa cattgcagtt cctgttgaaa gcactgattc   780
gctccggaac atcgatctga atgccattac gaatgaaaat gatgacaaaa aggctagcgc   840
agcagcggat gcctctgtgc ctgaacctga tgcctctgtg cctgaacctc aacagagag    900
caagcatgaa gaaattccag gtggtctct ttctgatgtg acaagatgg ccattgattc    960
gctgcagctt gcacaacttg gtaggccact agaagaggat gaagaagact atgatgaaga  1020
ggaggggtaa atattattag tctttggtga ttagattagt gaaaagctca tcatgataac  1080
tgtagaataa gtacatacta gtgttatgat tatgagtatc cactagctgt caatgcatgt  1140
```

```
accatgttgg ctgaagaaag gatctgaatg ccccttttca ttaatctgct ttgtatgtgt   1200
agctgatgta tcttttcctt gaccagtaat gttagtttcg tgtactttta ggcctaaaaa   1260
aaaaaaaaaa aaaa                                                    1274
```

<210> SEQ ID NO 34
<211> LENGTH: 294
<212> TYPE: PRT
<213> ORGANISM: Glycine max

<400> SEQUENCE: 34

```
Met Arg Lys Lys Leu Asp Thr Arg Phe Pro Ala Ala Arg Ile Lys Lys
 1               5                  10                  15

Ile Met Gln Ala Asp Glu Asp Val Gly Lys Ile Ala Leu Ala Val Pro
             20                  25                  30

Val Leu Val Ser Lys Ala Leu Glu Leu Phe Leu Gln Asp Leu Cys Asp
         35                  40                  45

Arg Thr Tyr Glu Ile Thr Leu Gln Arg Gly Ala Lys Thr Met Asn Ser
     50                  55                  60

Leu His Leu Lys His Cys Val Gln Ser Tyr Asn Val Phe Asp Phe Leu
 65                  70                  75                  80

Arg Asp Val Val Ser Arg Val Pro Asp Tyr Ser His Gly His Gly His
                 85                  90                  95

Ala Glu Ala Gly Pro Asp Asp Arg Ala Ile Ala Lys Arg Arg Lys Ala
            100                 105                 110

Val Gly Asp Asp Gly Asn Asp Ser Asp Glu Glu Ala Lys Arg Ser Lys
        115                 120                 125

Met His Glu Leu Gly His Thr Gly Ser Thr Gly Arg Gly Arg Gly Arg
    130                 135                 140

Gly Arg Gly Arg Gly Arg Gly Arg Gly Arg Pro Pro Leu Asn Arg Glu
145                 150                 155                 160

Ile Tyr His Gln Asp Ala Glu Ser Glu Pro Cys Thr Ser Val Gln Pro
                165                 170                 175

Ser Asn Pro Gln Asn Thr Asn Thr Ser Val Ala Met Asp Ser Gly Ser
            180                 185                 190

Glu Ser Lys Glu Ile Pro Lys Glu Gln Asn Ile Ala Val Pro Val Glu
        195                 200                 205

Ser Thr Asp Ser Leu Arg Asn Ile Asp Leu Asn Ala Ile Thr Asn Glu
    210                 215                 220

Asn Asp Asp Lys Lys Ala Ser Ala Ala Ala Asp Ala Ser Val Pro Glu
225                 230                 235                 240

Pro Asp Ala Ser Val Pro Glu Pro Pro Thr Glu Ser Lys His Glu Glu
                245                 250                 255

Ile Pro Gly Trp Ser Leu Ser Asp Val Asp Lys Met Ala Ile Asp Ser
            260                 265                 270

Leu Gln Leu Ala Gln Leu Gly Arg Pro Leu Glu Glu Asp Glu Glu Asp
        275                 280                 285

Tyr Asp Glu Glu Glu Gly
    290
```

<210> SEQ ID NO 35
<211> LENGTH: 534
<212> TYPE: DNA
<213> ORGANISM: Triticum sp.
<220> FEATURE:
<221> NAME/KEY: unsure

```
<222> LOCATION: (441)
<223> OTHER INFORMATION: n=a,c,g or t

<400> SEQUENCE: 35
gttccccgcg gcacggatca aaaagataat gcaagcagat gaggatgttg gcaaaattgc      60
actggctgtg cctgttttag tttcgagagc ccttgaattg tttctgcaag atttgatcga     120
ccactcatac aaaattactc ttcaaagtgg tgcaaagaca ctgaattcct tccacctaaa     180
gcaatgtgtg aagaggtaca gctcttttga cttcctaact gagattgtca acaaggtgcc     240
agatctcggt ggcggtgaat cttgtggaga tgaaagagga ttacccagaa gaaggaaatt     300
ttcaaatgga agcgacccag agaatgagga gccccgatct agcaaaatgc ccataagaag     360
cttgaacacc agtcccagag gacgaggcag aggtcgagga gagggcgag gcggcctcc      420 aaaccaagag aaaggaaatt ngttatgtac agtttgagga tgagagcagc atgtttgctg     480
aacaaagtga acccttgcca ggagattgag atagttccgg agaccaaccg tggc          534

<210> SEQ ID NO 36
<211> LENGTH: 151
<212> TYPE: PRT
<213> ORGANISM: Triticum sp.
<220> FEATURE:
<221> NAME/KEY: UNSURE
<222> LOCATION: (147)
<223> OTHER INFORMATION: Xaa=ANY AMINO ACID

<400> SEQUENCE: 36

Phe Pro Ala Ala Arg Ile Lys Lys Ile Met Gln Ala Asp Glu Asp Val
 1               5                  10                  15

Gly Lys Ile Ala Leu Ala Val Pro Val Leu Val Ser Arg Ala Leu Glu
                20                  25                  30

Leu Phe Leu Gln Asp Leu Ile Asp His Ser Tyr Lys Ile Thr Leu Gln
            35                  40                  45

Ser Gly Ala Lys Thr Leu Asn Ser Phe His Leu Lys Gln Cys Val Lys
        50                  55                  60

Arg Tyr Ser Ser Phe Asp Phe Leu Thr Glu Ile Val Asn Lys Val Pro
 65                  70                  75                  80

Asp Leu Gly Gly Gly Glu Ser Cys Gly Asp Glu Arg Gly Leu Pro Arg
                85                  90                  95

Arg Arg Lys Phe Ser Asn Gly Ser Asp Pro Glu Asn Glu Glu Pro Arg
            100                 105                 110

Ser Ser Lys Met Pro Ile Arg Ser Leu Asn Thr Ser Pro Arg Gly Arg
        115                 120                 125

Gly Arg Gly Arg Gly Arg Gly Arg Gly Pro Pro Asn Gln Glu Lys
    130                 135                 140

Gly Asn Xaa Leu Cys Thr Val
145                 150

<210> SEQ ID NO 37
<211> LENGTH: 458
<212> TYPE: DNA
<213> ORGANISM: Triticum sp.
<220> FEATURE:
<221> NAME/KEY: unsure
<222> LOCATION: (216)
<223> OTHER INFORMATION: n=a,c,g or t
<220> FEATURE:
<221> NAME/KEY: unsure
<222> LOCATION: (242)
<223> OTHER INFORMATION: n=a,c,g or t
<220> FEATURE:
```

```
<221> NAME/KEY: unsure
<222> LOCATION: (256)
<223> OTHER INFORMATION: n=a,c,g or t
<220> FEATURE:
<221> NAME/KEY: unsure
<222> LOCATION: (266)
<223> OTHER INFORMATION: n=a,c,g or t
<220> FEATURE:
<221> NAME/KEY: unsure
<222> LOCATION: (275)
<223> OTHER INFORMATION: n=a,c,g or t
<220> FEATURE:
<221> NAME/KEY: unsure
<222> LOCATION: (295)
<223> OTHER INFORMATION: n=a,c,g or t
<220> FEATURE:
<221> NAME/KEY: unsure
<222> LOCATION: (311)
<223> OTHER INFORMATION: n=a,c,g or t
<220> FEATURE:
<221> NAME/KEY: unsure
<222> LOCATION: (314)
<223> OTHER INFORMATION: n=a,c,g or t
<220> FEATURE:
<221> NAME/KEY: unsure
<222> LOCATION: (335)
<223> OTHER INFORMATION: n=a,c,g or t
<220> FEATURE:
<221> NAME/KEY: unsure
<222> LOCATION: (339)
<223> OTHER INFORMATION: n=a,c,g or t
<220> FEATURE:
<221> NAME/KEY: unsure
<222> LOCATION: (345)
<223> OTHER INFORMATION: n=a,c,g or t
<220> FEATURE:
<221> NAME/KEY: unsure
<222> LOCATION: (351)
<223> OTHER INFORMATION: n=a,c,g or t
<220> FEATURE:
<221> NAME/KEY: unsure
<222> LOCATION: (355)
<223> OTHER INFORMATION: n=a,c,g or t
<220> FEATURE:
<221> NAME/KEY: unsure
<222> LOCATION: (377)
<223> OTHER INFORMATION: n=a,c,g or t
<220> FEATURE:
<221> NAME/KEY: unsure
<222> LOCATION: (379)
<223> OTHER INFORMATION: n=a,c,g or t
<220> FEATURE:
<221> NAME/KEY: unsure
<222> LOCATION: (400)
<223> OTHER INFORMATION: n=a,c,g or t
<220> FEATURE:
<221> NAME/KEY: unsure
<222> LOCATION: (410)
<223> OTHER INFORMATION: n=a,c,g or t
<220> FEATURE:
<221> NAME/KEY: unsure
<222> LOCATION: (434)
<223> OTHER INFORMATION: n=a,c,g or t
<220> FEATURE:
<221> NAME/KEY: unsure
<222> LOCATION: (447)
<223> OTHER INFORMATION: n=a,c,g or t
<220> FEATURE:
<221> NAME/KEY: unsure
<222> LOCATION: (448)
<223> OTHER INFORMATION: n=a,c,g or t
<220> FEATURE:
<221> NAME/KEY: unsure
<222> LOCATION: (449)
<223> OTHER INFORMATION: n=a,c,g or t

<400> SEQUENCE: 37
gaggaagaag ctgggcaccc ggttccccgc ggcacggatc aaaaagataa tgcaagcaga    60
```

-continued

```
tgaggatgtt ggcaaaattg cactggctgt gcctgtttta gtttcgagag cccttgaatt    120
gtttctgcaa gatttgatcg accactcata caaaattact cttcaaagtg gtgcaaagac    180
actgaattcc ttccacctaa agcaatgtgt gaagangtac agctcttttg acttcctaac    240
tnagattgtc aacaangtgc caaatntccg tggcnggtta atcttgttgg agatnaaaga    300
ggattaccca naanaaggaa attttaaatt ggaancganc caaanaatga nggancccga    360
tttaacaaaa tgccatnana aacttgaaca ccattccaan aggacaaggn aaaggtccag    420
gaaaaggcaa gggnggctcc aaccaannna aaggaatt                           458
```

<210> SEQ ID NO 38
<211> LENGTH: 91
<212> TYPE: PRT
<213> ORGANISM: Triticum sp.
<220> FEATURE:
<221> NAME/KEY: UNSURE
<222> LOCATION: (72)
<223> OTHER INFORMATION: Xaa=ANY AMINO ACID
<220> FEATURE:
<221> NAME/KEY: UNSURE
<222> LOCATION: (81)
<223> OTHER INFORMATION: Xaa=ANY AMINO ACID
<220> FEATURE:
<221> NAME/KEY: UNSURE
<222> LOCATION: (85)
<223> OTHER INFORMATION: Xaa=ANY AMINO ACID
<220> FEATURE:
<221> NAME/KEY: UNSURE
<222> LOCATION: (89)
<223> OTHER INFORMATION: Xaa=ANY AMINO ACID

<400> SEQUENCE: 38

```
Arg Lys Lys Leu Gly Thr Arg Phe Pro Ala Ala Arg Ile Lys Lys Ile
 1               5                  10                  15

Met Gln Ala Asp Glu Asp Val Gly Lys Ile Ala Leu Ala Val Pro Val
            20                  25                  30

Leu Val Ser Arg Ala Leu Glu Leu Phe Leu Gln Asp Leu Ile Asp His
        35                  40                  45

Ser Tyr Lys Ile Thr Leu Gln Ser Gly Ala Lys Thr Leu Asn Ser Phe
    50                  55                  60

His Leu Lys Gln Cys Val Lys Xaa Tyr Ser Ser Phe Asp Phe Leu Thr
65                  70                  75                  80

Xaa Ile Val Asn Xaa Val Pro Asn Xaa Arg Gly
                85                  90
```

<210> SEQ ID NO 39
<211> LENGTH: 950
<212> TYPE: DNA
<213> ORGANISM: Triticum aestivum

<400> SEQUENCE: 39

```
gcacgaggag gaagaagctg ggcacccggt tccccgcggc acggatcaaa aagataatgc     60
aagcagatga ggatgttggc aaaattgcac tggctgtgcc tgttttagtt tcgagagccc    120
ttgaattgtt tctgcaagat tgatcgacc actcatacaa aattactctt caaagtggtg     180
caaagacact gaattccttc cacctaaagc aatgtgtgaa gagtacagc tcttttgact      240 tcctaactga gattgtcaac aaggtgccag atctcggtgg cggtgaatct tgtggagatg    300
aaagaggatt acccagaaga aggaaatttt caaatggaag cgacccagag aatgaggagc    360
cccgatctag caaaatgccc ataagaagct tgaacaccag tcccagagga cgaggcagag    420
```

-continued

```
gtcgaggaag agggcgaggg cggcctccaa ccaagagaaa ggaaattggt tatgtacagt      480
ttgaggatga gagcagcatg tttgctgaac aaagtgaacc cttgccagga gatgagatag      540
ttccggagac caaccgtggc aatgagagta ttccccaaag ctcacatcct ctagtggagg      600
ctccatcagc catgacgcca gctgtgattt caaaggttga agaagctagc accaaccatc      660
agccagattg gcctatgcca gatgccattg gaggcattgg tgttggacca tccagttttg      720
gacatctgac agtgcaggtt gatgaggtag aggactacga caatgaggat taggcatagt      780
catcctctca ttcatcatat gctctaacag gacagttctc ctggtgttgt acattgtaaa      840
tattgtttca gtagttact gcagctatga tgtgtaacct atttctttt cccaataatt       900 ggttctgagt tgccgcattg ttgacctaaa aaaaaaaaaa aaaaaaaaa                  950
```

<210> SEQ ID NO 40
<211> LENGTH: 256
<212> TYPE: PRT
<213> ORGANISM: Triticum aestivum

<400> SEQUENCE: 40

```
Thr Arg Arg Lys Lys Leu Gly Thr Arg Phe Pro Ala Ala Arg Ile Lys
  1               5                  10                  15

Lys Ile Met Gln Ala Asp Glu Asp Val Gly Lys Ile Ala Leu Ala Val
                 20                  25                  30

Pro Val Leu Val Ser Arg Ala Leu Glu Leu Phe Leu Gln Asp Leu Ile
             35                  40                  45

Asp His Ser Tyr Lys Ile Thr Leu Gln Ser Gly Ala Lys Thr Leu Asn
         50                  55                  60

Ser Phe His Leu Lys Gln Cys Val Lys Arg Tyr Ser Ser Phe Asp Phe
 65                  70                  75                  80

Leu Thr Glu Ile Val Asn Lys Val Pro Asp Leu Gly Gly Gly Glu Ser
                 85                  90                  95

Cys Gly Asp Glu Arg Gly Leu Pro Arg Arg Lys Phe Ser Asn Gly
            100                 105                 110

Ser Asp Pro Glu Asn Glu Glu Pro Arg Ser Ser Lys Met Pro Ile Arg
        115                 120                 125

Ser Leu Asn Thr Ser Pro Arg Gly Arg Gly Arg Gly Arg Gly Arg Gly
    130                 135                 140

Arg Gly Arg Pro Pro Thr Lys Arg Lys Glu Ile Gly Tyr Val Gln Phe
145                 150                 155                 160

Glu Asp Glu Ser Ser Met Phe Ala Glu Gln Ser Glu Pro Leu Pro Gly
                165                 170                 175

Asp Glu Ile Val Pro Glu Thr Asn Arg Gly Asn Glu Ser Ile Pro Gln
            180                 185                 190

Ser Ser His Pro Leu Val Glu Ala Pro Ser Ala Met Thr Pro Ala Val
        195                 200                 205

Ile Ser Lys Val Glu Glu Ala Ser Thr Asn His Gln Pro Asp Trp Pro
    210                 215                 220

Met Pro Asp Ala Ile Gly Gly Ile Gly Val Gly Pro Ser Ser Phe Gly
225                 230                 235                 240

His Leu Thr Val Gln Val Asp Glu Val Glu Asp Tyr Asp Asn Glu Asp
                245                 250                 255
```

<210> SEQ ID NO 41
<211> LENGTH: 159
<212> TYPE: PRT
<213> ORGANISM: Arabidopsis thaliana

```
<400> SEQUENCE: 41

Met Asp Pro Met Asp Ile Val Gly Lys Ser Lys Glu Asp Ala Ser Leu
1               5                   10                  15

Pro Lys Ala Thr Met Thr Lys Ile Ile Lys Glu Met Leu Pro Pro Asp
                20                  25                  30

Val Arg Val Ala Arg Asp Ala Gln Asp Leu Leu Ile Glu Cys Cys Val
            35                  40                  45

Glu Phe Ile Asn Leu Val Ser Ser Glu Ser Asn Asp Val Cys Asn Lys
        50                  55                  60

Glu Asp Lys Arg Thr Ile Ala Pro Glu His Val Leu Lys Ala Leu Gln
65                  70                  75                  80

Val Leu Gly Phe Gly Glu Tyr Ile Glu Val Tyr Ala Ala Tyr Glu
                85                  90                  95

Gln His Lys Tyr Glu Thr Met Gln Asp Thr Gln Arg Ser Val Lys Trp
                100                 105                 110

Asn Pro Gly Ala Gln Met Thr Glu Glu Ala Ala Ala Glu Gln Gln
                115                 120                 125

Arg Met Phe Ala Glu Ala Arg Ala Arg Met Asn Gly Gly Val Ser Val
130                 135                 140

Pro Gln Pro Glu His Pro Glu Thr Asp Gln Arg Ser Pro Gln Ser
145                 150                 155

<210> SEQ ID NO 42
<211> LENGTH: 205
<212> TYPE: PRT
<213> ORGANISM: Homo sapiens

<400> SEQUENCE: 42

Met Pro Ser Lys Lys Lys Tyr Asn Ala Arg Phe Pro Pro Ala Arg
1               5                   10                  15

Ile Lys Lys Ile Met Gln Thr Asp Glu Glu Ile Gly Lys Val Ala Ala
                20                  25                  30

Ala Val Pro Val Ile Ile Ser Arg Ala Leu Glu Leu Phe Leu Glu Ser
            35                  40                  45

Leu Leu Lys Lys Ala Cys Gln Val Thr Gln Ser Arg Asn Ala Lys Thr
        50                  55                  60

Met Thr Thr Ser His Leu Lys Gln Cys Ile Glu Leu Glu Gln Gln Phe
65                  70                  75                  80

Asp Phe Leu Lys Asp Leu Val Ala Ser Val Pro Asp Met Gln Gly Asp
                85                  90                  95

Gly Glu Asp Asn His Met Asp Gly Asp Lys Gly Ala Arg Arg Gly Arg
                100                 105                 110

Lys Pro Gly Ser Gly Gly Arg Lys Asn Gly Gly Met Gly Thr Lys Ser
                115                 120                 125

Lys Asp Lys Lys Leu Ser Gly Thr Asp Ser Glu Gln Glu Asp Glu Ser
130                 135                 140

Glu Asp Thr Asp Thr Asp Gly Glu Glu Glu Thr Ser Gln Pro Pro
145                 150                 155                 160

Gln Ala Ser His Pro Ser Ala His Phe Gln Ser Pro Thr Pro Phe
                165                 170                 175

Leu Pro Phe Ala Ser Thr Leu Pro Leu Pro Ala Pro Pro Gly Pro
                180                 185                 190

Ser Ala Pro Asp Glu Glu Asp Glu Glu Asp Tyr Asp Ser
                195                 200                 205
```

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 43
gttgctcagc tacagcttgt tcc                                              23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 44
ttggagaatc cagggtatca tgc                                              23

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence:Synthetic
      Oligonucleotide
<220> FEATURE:
<221> NAME/KEY: modified_base
<222> LOCATION: (24)..(25)
<223> OTHER INFORMATION: i
<220> FEATURE:
<221> NAME/KEY: modified_base
<222> LOCATION: (29)..(30)
<223> OTHER INFORMATION: i
<220> FEATURE:
<221> NAME/KEY: modified_base
<222> LOCATION: (34)..(35)
<223> OTHER INFORMATION: i

<400> SEQUENCE: 45
ggccacgcgt cgactagtac gggnngggnn gggnng                                36

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 46
caagtcgacg gccgcttgaa cctcttc                                          27

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 47
cttatactga ggctacacaa c                                                21

```
<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 48
atacccgggt gaactgtcca agccatgttc                                      30

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 49
gttaggtgtc gcgcctggag a                                               21

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 50
taagaattca tggatccgat ggatatcgtg                                      30

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 51
cgggatccga tagtgggatt gtgcgtc                                         27

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 52
actggctcac gctaggaacc                                                 20

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 53
gcccagcttc ttccccatgg cttcgtcttc ctgc                                 34

<210> SEQ ID NO 54
```

```
<211> LENGTH: 36
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 54
gatggccgtg gctactcgag atcctcgttg tcgtag                              36

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 55
ggcaattgag gaagaagctg ggca                                           24

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 56
ccatcacagc tagctgcagc                                                20

<210> SEQ ID NO 57
<211> LENGTH: 38
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 57
ccagaacctg aagcgtggcc acagcaacaa acacaaca                            38

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 58
ggccatggaa gacgccaaaa ac                                             22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 59
ggggcccggt acccggggat cc                                             22

<210> SEQ ID NO 60
<211> LENGTH: 38
```

-continued

```
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 60
gcaaagacat tgaatcaatt gtccttccac ctaaagca                              38

<210> SEQ ID NO 61
<211> LENGTH: 37
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 61
agagggcgag gacgagatat cccacccacc aagcgga                               37

<210> SEQ ID NO 62
<211> LENGTH: 37
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 62
gaatctcgat caagcgatat caaaatggcc gtaagaa                               37

<210> SEQ ID NO 63
<211> LENGTH: 36
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 63
tgtgtgagga ggtacgatat cagttctttt gacttc                                36

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 64
aacaattgga ggagcggagg cgga                                             24

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 65
aaccatggaa tcctcgttgt cgtagtc                                          27

<210> SEQ ID NO 66
<211> LENGTH: 1073
<212> TYPE: DNA
```

<213> ORGANISM: Oryza sativa
<220> FEATURE:
<221> NAME/KEY: unsure
<222> LOCATION: (525)
<223> OTHER INFORMATION: n=a,c,g or t

<400> SEQUENCE: 66

```
agataaccct agcctccccc ttcctcttcc tctcctcctt ctcgatctct ataaaagacc    60
tcggatttcg aattcctccg ccccgcgcgc gcgcgccacc tccccacgc ccgtcgcgcc   120
cttttttttg ggggtgggat tcgcctggtc aagtgccatc gtcggatcat ggcggcggag   180
gcggcagcgg cgctggaggg gagcgagccc gtggacctgg ccaagcaccc ctccggcatc   240
atccccacgc tccaaaacat cgtatcgacg gtcaatttgg attgcaaatt agacctcaaa   300
gctatagctt tgcaagctcg caatgcagaa tataatccaa agcgttttgc tgcggttatc   360
atgagaataa gagaaccaaa aactacagct ctgatatttg catcgggtaa aatggtctgt   420
actgggcaa agagtgaaca acaatccaag cttgcagcaa gaaagtacgc tcgtattatc   480
cagaagcttg gctttcctgc taaattcaag gatttcaaga ttcanaacat tgttggctct   540
tgtgatgtta aatttccaat caggctggag ggacttgcat attctcatgg tgctttctca   600
agttatgagc cagaactctt tcctggtctg atatatcgga tgaagcaacc aaagattgtt   660
cttctgattt tgtttcagg caagattgtt ttgaccggag caaaggtgag ggatgagacg   720
tataccgcct ttgagaacat ataccctgtg ctaacggagt tcagaaaagt ccagcagtga   780
aaacttatgg aatacacaag tacaagcttc cttgagattt tgctgcctag tgactgctaa   840
tcttaactgt acatatggtc tggaggagcg tatagcatct tgtaatttat gtgagcccct   900
cgatgcacga gtgttgtaga cttgttgtag taggcttgta gcttgggtga ctgagagact   960
tgagtatcgc gttcagtcga acgaggtgga gacgtggagt tatcgtactt tagcccgtgc  1020
tgatttttttt cccttcacaa atagatctgt agcgaaacat tttattacag aaa         1073
```

<210> SEQ ID NO 67
<211> LENGTH: 203
<212> TYPE: PRT
<213> ORGANISM: Oryza sativa
<220> FEATURE:
<221> NAME/KEY: UNSURE
<222> LOCATION: (119)
<223> OTHER INFORMATION: Xaa=ANY AMINO ACID

<400> SEQUENCE: 67

```
Met Ala Ala Glu Ala Ala Ala Leu Glu Gly Ser Glu Pro Val Asp
  1               5                  10                  15

Leu Ala Lys His Pro Ser Gly Ile Ile Pro Thr Leu Gln Asn Ile Val
                 20                  25                  30

Ser Thr Val Asn Leu Asp Cys Lys Leu Asp Leu Lys Ala Ile Ala Leu
             35                  40                  45

Gln Ala Arg Asn Ala Glu Tyr Asn Pro Lys Arg Phe Ala Ala Val Ile
         50                  55                  60

Met Arg Ile Arg Glu Pro Lys Thr Thr Ala Leu Ile Phe Ala Ser Gly
 65                  70                  75                  80

Lys Met Val Cys Thr Gly Ala Lys Ser Glu Gln Gln Ser Lys Leu Ala
                     85                  90                  95

Ala Arg Lys Tyr Ala Arg Ile Ile Gln Lys Leu Gly Phe Pro Ala Lys
                100                 105                 110

Phe Lys Asp Phe Lys Ile Xaa Asn Ile Val Gly Ser Cys Asp Val Lys
            115                 120                 125
```

```
Phe Pro Ile Arg Leu Glu Gly Leu Ala Tyr Ser His Gly Ala Phe Ser
        130                 135                 140

Ser Tyr Glu Pro Glu Leu Phe Pro Gly Leu Ile Tyr Arg Met Lys Gln
145                 150                 155                 160

Pro Lys Ile Val Leu Leu Ile Phe Val Ser Gly Lys Ile Val Leu Thr
                165                 170                 175

Gly Ala Lys Val Arg Asp Glu Thr Tyr Thr Ala Phe Glu Asn Ile Tyr
                180                 185                 190

Pro Val Leu Thr Glu Phe Arg Lys Val Gln Gln
        195                 200

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 68
gccatcgtcg gatccatggc ggcggaggcg                                    30

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 69
ccataagttt tcactcgagc tgctggactt t                                  31
```